(12) United States Patent
Hellinga et al.

(10) Patent No.: US 11,352,657 B2
(45) Date of Patent: Jun. 7, 2022

(54) GLUCOSE/GALACTOSE BIOSENSORS AND METHODS OF USING SAME

(71) Applicant: Duke University, Durham, NC (US)

(72) Inventors: Homme W. Hellinga, Durham, NC (US); Malin Allert, Raleigh, NC (US)

(73) Assignee: Duke University, Durham, NC (US)

( * ) Notice: Subject to any disclaimer, the term of this patent is extended or adjusted under 35 U.S.C. 154(b) by 270 days.

(21) Appl. No.: 15/555,064

(22) PCT Filed: Mar. 4, 2016

(86) PCT No.: PCT/US2016/021073
§ 371 (c)(1),
(2) Date: Aug. 31, 2017

(87) PCT Pub. No.: WO2016/141363
PCT Pub. Date: Sep. 9, 2016

(65) Prior Publication Data
US 2018/0037928 A1     Feb. 8, 2018

Related U.S. Application Data

(60) Provisional application No. 62/128,592, filed on Mar. 5, 2015.

(51) Int. Cl.
| | | |
|---|---|---|
| *C12Q 1/54* | (2006.01) |
| *G01N 33/543* | (2006.01) |
| *G01N 33/58* | (2006.01) |
| *C07H 3/02* | (2006.01) |
| *C12N 15/66* | (2006.01) |

(52) U.S. Cl.
CPC ........... *C12Q 1/54* (2013.01); *G01N 33/5438* (2013.01); *G01N 33/582* (2013.01); *C07H 3/02* (2013.01); *C12N 15/66* (2013.01)

(58) Field of Classification Search
CPC .... C12Q 1/54; G01N 33/5438; G01N 33/582; C07H 3/02; C12N 15/66
See application file for complete search history.

(56) References Cited

U.S. PATENT DOCUMENTS

| | | |
|---|---|---|
| 4,554,101 A | 11/1985 | Hopp |
| 6,277,627 B1 | 8/2001 | Hellinga |
| 7,326,538 B2 | 2/2008 | Pitner et al. |
| 7,629,172 B2 | 12/2009 | Alarcon et al. |
| 8,608,310 B2 | 12/2013 | Otis et al. |
| 2002/0004217 A1 | 1/2002 | Hellinga |
| 2005/0274629 A1* | 12/2005 | Lin .................... G01N 33/5438 205/777.5 |
| 2011/0091919 A1* | 4/2011 | Ye ........................ C07K 14/245 435/14 |
| 2012/0232251 A1 | 9/2012 | Pickup et al. |

OTHER PUBLICATIONS

Zhao et al., Sci. Technol. Adv. Mater. 14:1-7, 054402, 2013.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
De Lorimier et al., Protein Science 11:2655-2675, 2002.*
DeLorimier et al., Construction of a fluorescent biosensor family. Prot. Sci. 2002;11:2655-75.
Diabetes Control and Complications Trial Research Group et al., The effect of intensive treatment of diabetes on the development and progression of long-term complications in insulin-dependent diabetes mellitus. N Engl J Med. Sep. 30, 1993;329(14):977-86.
Gough et al., Development of the implantable glucose sensor. What are the prospects and why is it taking so long? Diabetes. Sep. 1995;44(9):1005-9.
Heagerty et al., Time-dependent ROC curves for censored survival data and a diagnostic marker. Biometrics. Jun. 2000;56(2):337-44.
Judge et al., Continuous glucose monitoring using a novel glucose/galactose binding protein: results of a 12-hour feasibility study with the becton dickinson glucose/galactose binding protein sensor. Diabetes Technol Ther. Mar. 2011;13(3):309-17.
Kyte et al., A simple method for displaying the hydropathic character of a protein. J Mol Biol. May 5, 1982;157(1):105-32.
Lakowicz, Principles of Fluorescence Spectroscopy, 2nd Ed. Kluwer Academic Press, New York, (1999).
Layton et al., Thermodynamic analysis of ligand-induced changes in protein thermal unfolding applied to high-throughput determination of ligand affinities with extrinsic fluorescent dyes. Biochemistry. Dec. 28, 2010;49(51):10831-41.
Marvin et al., The rational design of allosteric interactions in a monomeric protein and its applications to the construction of biosensors. Proc Natl Acad Sci U S A. Apr. 29, 1997;94(9):4366-71.
Meyerhoff et al., Current Status of the Glucose Sensor. Endricon. 1966;6(1):51-8.
Mosbach et al., Formation of proinsulin by immobilized Bacillus subtilis. Nature. Apr. 7, 1983;302(5908):543-5.
Palva et al., Secretion of interferon by Bacillus subtilis. Gene. May-Jun. 1983;22(2-3):229-35.
Pickup, J. Developing glucose sensors for in vivo use. Trends Biotechnol. Jul. 1993;11(7):285-91.
Pool et al., Natural sweetening of food products by engineering Lactococcus lactis for glucose production. Metab Eng. Sep. 2006;8(5):456-64.
Riklin et al., Improving enzyme-electrode contacts by redox modification of cofactors. Nature. Aug. 24, 1995;376(6542):672-5.
Suleiman et al., In: Biosensor Design and Application: Mathewson and Finley Eds; American Chemical Society, Washington, DC 1992, vol. 511, chapter 3.
Vyas et al., A novel calcium binding site in the galactose-binding protein of bacterial transport and chemotaxis. Nature. Jun. 18-24, 1987;327(6123):635-8.

(Continued)

*Primary Examiner* — Delia M Ramirez
(74) *Attorney, Agent, or Firm* — Mintz Levin Cohn Ferris Glovsky and Popeo, P.C.; Ingrid A. Beattie

(57) ABSTRACT

Provided herein are glucose and galactose biosensors and methods of making and using the same.

25 Claims, 33 Drawing Sheets

Specification includes a Sequence Listing.

(56) References Cited

OTHER PUBLICATIONS

Vyas et al., Crystallographic analysis of the epimeric and anomeric specificity of the periplasmic transport/chemosensory protein receptor for D-glucose and D-galactose. Biochemistry. Apr. 26, 1994;33(16):4762-8.
Vyas et al., Sugar and signal-transducer binding sites of the *Escherichia coli* galactose chemoreceptor protein. Science. Dec. 2, 1988;242(4883):1290-5.
Wilkins et al., Glucose monitoring: state of the art and future possibilities. Med Eng Phys. Jun. 1996;18(4):273-88.
Willner et al., Electrical Wiring of Glucose Oxidase by Reconstitution of FAD-Modified Monolayers Assembled onto Au-Electrodes. J. Am. Chem. Soc., 1996;118(42):10321-2.
Vallée-Bélisle and Plaxco, Structure-switching biosensors: inspired by Nature. Current Opinion in Structural Biology, Jun. 2010, 20:518-526.
Matysik, Advances in Chemical Bioanalysis, Springer Cham, Switzerland (2014).

\* cited by examiner

```
GCACTGCAGCGGCGTAGAGGATCGAGATCTCGATCCCGCGAAATTAATACGACTCACTATAGGGGAATTGTGAGCGGATAACAATTCCCCTCTAGAAATA
CGTGACGTCGCCGCATCTCCTAGCTCTAGAGCTAGGGCGCTTTAATTATGCTGAGTGATATCCCCTTAACACTCGCCTATTGTTAAGGGGAGATCTTTAT
         10        20        30        40        50        60        70        80        90       100

10                             20
                                         M  A  D  T  R  I  G  V  T  I  Y  K  Y  D  D  N  F  M  S  V  V  R  K
ATTTTGTTTAACTTTAAGAAGGAGATATACCATGGCAGATACTCGTATTGGTGTAACTATTTATAAATACGATGATAATTTCATGAGCGTAGTACGTAAA
TAAAACAAATTGAAATTCTTCCTCTATATGGTACCGTCTATGAGCATAACCACATTGATAAATATTTATGCTACTATTAAAGTACTCGCATCATGCATTT
        110       120       130       140       150       160       170       180       190       200

30                                        40                                 50
 A  I  E  Q  D  A  K  A  A  P  D  V  Q  L  L  M  N  D  S  Q  N  D  Q  S  K  Q  N  D  Q  I  D  V  L  L
GCAATTGAACAAGATGCGAAAGCGGCCCCGGATGTTCAGCTGCTGATGAACGATAGCCAGAACGATCAGAGCAAACAGAACGATCAGATTGATGTGCTGC
CGTTAACTTGTTCTACGCTTTCGCCGGGGCCTACAAGTCGACGACTACTTGCTATCGGTCTTGCTAGTCTCGTTTGTCTTGCTAGTCTAACTACACGACG
        210       220       230       240       250       260       270       280       290       300

60                                70                                  80
 A  K  G  V  K  A  L  A  I  N  L  V  D  P  A  A  A  G  T  V  I  E  K  A  R  G  Q  N  V  P  V  V  F
TGGCCAAAGGCGTGAAAGCCCTGGCCATTAACCTGGTTGATCCGGCGGCGGCCGGTACCGTTATTGAAAAAGCCCGTGGCCAGAACGTGCCGGTGGTGTT
ACCGGTTTCCGCACTTTCGGGACCGGTAATTGGACCAACTAGGCCGCCGCCGGCCATGGCAATAACTTTTTCGGGCACCGGTCTTGCACGGCCACCACAA
        310       320       330       340       350       360       370       380       390       400

100                                 110                             120
 F  N  K  E  P  S  R  K  A  L  D  S  Y  D  K  A  Y  Y  V  G  T  D  S  K  E  S  G  I  I  Q  G  D  L
CTTCAACAAAGAACCGAGCCGCAAAGCGCTGGATAGCTACGATAAAGCGTACTATGTGGGCACCGATAGCAAAGAAAGCGGCATTATTCAGGGCGATCTG
GAAGTTGTTTCTTGGCTCGGCGTTTCGCGACCTATCGATGCTATTTCGCATGATACACCCGTGGCTATCGTTTCTTTCGCCGTAATAAGTCCCGCTAGAC
        410       420       430       440       450       460       470       480       490       500

130                                140                                 150
 I  A  K  H  W  A  A  N  Q  G  W  D  L  N  K  D  G  Q  I  Q  F  V  L  L  K  G  E  P  G  H  P  D  A  E
ATTGCGAAACATTGGGCGGCGAACCAGGGCTGGGATCTGAACAAAGATGGCCAGATTCAGTTCGTGCTGCTGAAAGGCGAACCGGGTCATCCGGATGCCG
TAACGCTTTGTAACCCGCCGCTTGGTCCCGACCCTAGACTTGTTTCTACCGGTCTAAGTCAAGCACGACGACTTTCCGCTTGGCCCAGTAGGCCTACGGC
        510       520       530       540       550       560       570       580       590       600

160                                 170                                180
 A  R  T  T  Y  V  I  K  E  L  N  D  K  G  I  K  T  E  Q  L  Q  L  D  T  A  M  W  D  T  A  Q  A  K
AAGCGCGTACCACCTATGTGATCAAAGAACTGAACGACAAAGGCATCAAAACCGAACAGCTGCAACTGGATACCGCGATGTGGGATACCGCGCAGGCGAA
TTCGCGCATGGTGGATACACTAGTTTCTTGACTTGCTGTTTCCGTAGTTTTGGCTTGTCGACGTTGACCTATGGCGCTACACCCTATGGCGCGTCCGCTT
        610       620       630       640       650       660       670       680       690       700

200                               210                              220
 D  K  M  D  A  W  L  S  G  P  N  A  N  K  I  E  V  V  I  A  N  N  D  A  M  A  M  G  A  V  E  A  L
AGATAAAATGGATGCGTGGCTGAGCGGTCCGAACGCGAACAAAATTGAAGTGGTGATTGCGAACAACGATGCGATGGCGATGGGCGCGGTGGAAGCGCTG
TCTATTTTACCTACGCACCGACTCGCCAGGCTTGCGCTTGTTTTAACTTCACCACTAACGCTTGTTGCTACGCTACCGCTACCCGCGCCACCTTCGCGAC
        710       720       730       740       750       760       770       780       790       800

230                                240                               250
 K  A  H  N  K  S  S  I  P  V  F  G  V  D  A  L  P  E  A  L  A  L  V  K  S  G  A  L  A  G  T  V  L  N
AAAGCCCATAACAAATCCAGCATTCCGGTGTTTGGCGTGGATGCCCTGCCGGAAGCGCTGGCGCTGGTTAAAAGCGGTGCGCTGGCGGGCACCGTTCTGA
TTTCGGGTATTGTTTAGGTCGTAAGGCCACAAACCGCACCTACGGGACGGCCTTCGCGACCGCGACCAATTTTCGCCACGCGACCGCCGTGGCAAGACT
        810       820       830       840       850       860       870       880       890       900

260                               270                                 280
 D  A  N  N  Q  A  K  A  T  F  D  L  A  K  N  L  A  D  G  K  G  A  A  D  G  T  N  W  K  I  D  N  K
ACGATGCCAACAACCAGGCGAAAGCCACCTTCGATCTGGCGAAAAACCTGGCGGATGGTAAAGGCGCGGCCGATGGCACCAACTGGAAAATTGATAACAA
TGCTACGGTTGTTGGTCCGCTTTCGGTGGAAGCTAGACCGCTTTTTGGACCGCCTACCATTTCCGCGCCGGCTACCGTGGTTGACCTTTTAACTATTGTT
        910       920       930       940       950       960       970       980       990      1000

300                                 310
 V  V  R  V  P  Y  V  G  V  D  K  D  N  L  A  E  F  G  G  S  H  H  H  H  H  H  *  *
AGTGGTGCGTGTGCCGTATGTGGGCGTGGATAAAGATAACCTGGCCGAATTTGGCGGCAGCCATCATCACCATCACCACTAATAAGAGATCCGGCTGCTA
TCACCACGCACACGGCATACACCCGCACCTATTTCTATTGGACCGGCTTAAACCGCCGTCGGTAGTAGTGGTAGTGGTGATTATTCTCTAGGCCGACGAT
       1010      1020      1030      1040      1050      1060      1070      1080      1090      1100

ACAAAGCCCGAAAGGAAGCTGAGTTGGCTGCTGCCACCGCTGAGCAATAACTAGCATAACCCCTTGGGGCCTCTAAACGGGTCTTGAGGGAATTCGTA (SEQ ID NO:
113)
TGTTTCGGGCTTTCCTTCGACTCAACCGACGACGGTGGCGACTCGTTATTGATCGTATTGGGGAACCCCGGAGATTTGCCCAGAACTCCCTTAAGCAT (SEQ ID NO:
114)
       1110      1120      1130      1140      1150      1160      1170      1180      119
The amino acid sequence with single underlining refers to SEQ ID NO: 55.
The amino acid sequence (GGSHHHHHH) with double underlining refers to SEQ ID NO: 111.
```

FIG. 23

GLUCOSE/GALACTOSE BIOSENSORS AND METHODS OF USING SAME

CROSS-REFERENCE TO RELATED APPLICATIONS

This application is a national stage application filed under 35 U.S.C. § 371, of International Patent Application No. PCT/US2016/021073, filed Mar. 4, 2016, which claims the benefit of and priority to U.S. Provisional Patent Application No. 62/128,592, filed Mar. 5, 2015, the contents of each of which are incorporated herein by reference in their entireties.

INCORPORATION BY REFERENCE OF SEQUENCE LISTING

The entire content of the text file named "035327-520N01US_UPDATED_SequenceListing.txt", which was created on Mar. 2, 2020 and is 225 KB in size, is hereby incorporated herein by reference for all purposes.

FIELD

This disclosure relates to compositions and methods for detecting and determining the concentration of glucose and/or galactose.

INTRODUCTION

Glucose monitoring is essential for the management of diabetes mellitus, a disease that affects at least 366 million people worldwide. Reagentless fluorescent sensors based on engineered bacterial periplasmic glucose-binding proteins into which a single, environmentally sensitive fluorophore has been introduced are emerging as promising next-generation glucose sensors. Unlike traditional enzyme-based glucose sensors, one key advantage of reagentless sensors is that their monitoring mechanism requires neither additional substrates for a signal to develop, nor measurement of substrate consumption or product generation rates to deduce glucose concentrations. Instead, the signal originates from the response of the attached fluorophore to a glucose-induced conformational change in the protein, which is in dynamic equilibrium with the environment within which the sensor has been placed. This mechanism therefore reports near-instantaneously on the sample glucose concentration and its fluctuations. Pathophysiological blood glucose concentrations range from ~3-30 mM, with euglycemia at ~6 mM and the hyperglycemic-hyperosmotic range at greater than about 30 mM. Improved glucose sensors and methods for monitoring glucose at physiological levels are desirable.

SUMMARY

Provided herein are biosensors. The biosensor may include a) a polypeptide comprising a ligand binding site and (i) one or more mutations as compared to SEQ ID NO:112 (wild-type E. coli GGBP) that alter the ligand binding affinity of the polypeptide; and b) a reporter conjugated to the polypeptide, wherein when the polypeptide consists of a single mutation, the single mutation is F16C, wherein the ligand-bound biosensor results in a reporter-generated signal that is different from the unbound biosensor, and wherein the ligand is selected from the group consisting of glucose, galactose, and a combination thereof.

In some embodiments, the reporter is conjugated to F16C. In some embodiments, the polypeptide further comprises (ii) at least one additional mutation that replaces an amino acid with a cysteine. In some embodiments, the reporter is conjugated to the cysteine. In some embodiments, the biosensor comprises a single reporter. In some embodiments, the reporter comprises a fluorophore and wherein the signal is a fluorescent signal. In some embodiments, the fluorophore is selected from the group consisting of acrylodan and badan. In some embodiments, the signal comprises an emission intensity of the fluorophore recorded at one or more wavelengths. In some embodiments, the change in signal comprises a shift in the one or more wavelengths. In some embodiments, the signal comprises a ratio of emission intensities recorded at two or more wavelengths. In some embodiments, the change in signal comprises a shift in two or more wavelengths. In some embodiments, the at least one additional mutation (ii) is W183C. In some embodiments, the reporter is conjugated to W183C. In some embodiments, each mutation (i) is a mutation to an amino acid selected from the group consisting of Y10, D14, F16, N91, K92, E149, H152, D154, A155, R158, M182, N211, D236, and N256, and combinations thereof. In some embodiments, each mutation (i) is selected from the group consisting of Y10A, D14A, D14Q, D14N, D14S, D14T, D14E, D14H, D14L, D14Y, D14F, F16L, F16A, N91A, K92A, E149K, E149Q, E149S, H152A, H152F, H152Q, H152N, D154A, D154N, A155S, A155H, A155L, A155F, A155Y, A155N, A155K, A155M, A155W, A155Q, R158A, R158K, M182W, N211F, N211W, N211K, N211Q, N211S, N211H, N211M, D236A, D236N, N256A, and N256D, and combinations thereof. In some embodiments, the mutation (i) affects the interaction of the polypeptide with bound glucose, wherein the interaction is with a portion of the glucose selected from the group consisting of 1-hydroxyl, 2-hydroxyl, 3-hydroxyl, 4-hydroxyl, 6-hydroxyl, pyranose ring, and combinations thereof. In some embodiments, the mutation (i) affects the interaction of the mutant polypeptide with the reporter group. In some embodiments, the mutation (i) affects the interaction of the mutant polypeptide with a water molecule. In some embodiments, the polypeptide has an affinity (KD) for glucose within the concentration range of glucose in vivo for a subject. In some embodiments, the polypeptide has an affinity (KD) for galactose within the concentration range of galactose in vivo for a subject. In some embodiments, the subject is a mammal. In some embodiments, the subject is a primate or non-primate. In some embodiments, the subject is a non-primate selected from a cow, pig, camel, llama, horse, goat, rabbit, sheep, hamsters, guinea pig, cat, dog, rat, and mouse. In some embodiments, the subject is a primate selected from a monkey, chimpanzee, and human. In some embodiments, the subject is a human.

In some embodiments, the polypeptide has an affinity (KD) for glucose in the range of about 0.2 mM to about 100 mM. In some embodiments, the polypeptide has an affinity (KD) for galactose in the range of about 0.8 mM to about 100 mM. In some embodiments, the biosensor is capable of detecting glucose in the hypoglycemic, hyperglycemic, and hyperglycemic-hyperosmotic ranges. In some embodiments, the biosensor is capable of detecting glucose in the range of about 0.1 mmol/L to about 120 mmol/L. In some embodiments, the biosensor is capable of detecting glucose in the range of about 4 mmol/L to about 33 mmol/L. In some embodiments, the biosensor is capable of detecting galactose in the range of about 0.2 mM to about 400 mM.

In some embodiments, the mutant polypeptide comprises an amino acid sequence selected from the group consisting of SEQ ID NOs: 1-54.

Further provided herein is a polypeptide comprising the amino acid sequence of SEQ ID NO: 1. Further provided herein is a polypeptide comprising the amino acid sequence of SEQ ID NO: 2. Further provided herein is a polypeptide comprising the amino acid sequence of SEQ ID NO: 3. Further provided herein is a polypeptide comprising the amino acid sequence of SEQ ID NO: 4. Further provided herein is a polypeptide comprising the amino acid sequence of SEQ ID NO: 5. Further provided herein is a polypeptide comprising the amino acid sequence of SEQ ID NO: 6. Further provided herein is a polypeptide comprising the amino acid sequence of SEQ ID NO: 7. Further provided herein is a polypeptide comprising the amino acid sequence of SEQ ID NO: 8. Further provided herein is a polypeptide comprising the amino acid sequence of SEQ ID NO: 9. Further provided herein is a polypeptide comprising the amino acid sequence of SEQ ID NO: 10. Further provided herein is a polypeptide comprising the amino acid sequence of SEQ ID NO: 11. Further provided herein is a polypeptide comprising the amino acid sequence of SEQ ID NO: 12. Further provided herein is a polypeptide comprising the amino acid sequence of SEQ ID NO: 13. Further provided herein is a polypeptide comprising the amino acid sequence of SEQ ID NO: 14. Further provided herein is a polypeptide comprising the amino acid sequence of SEQ ID NO: 15. Further provided herein is a polypeptide comprising the amino acid sequence of SEQ ID NO: 16. Further provided herein is a polypeptide comprising the amino acid sequence of SEQ ID NO: 17. Further provided herein is a polypeptide comprising the amino acid sequence of SEQ ID NO: 18. Further provided herein is a polypeptide comprising the amino acid sequence of SEQ ID NO: 19. Further provided herein is a polypeptide comprising the amino acid sequence of SEQ ID NO: 20. Further provided herein is a polypeptide comprising the amino acid sequence of SEQ ID NO: 21. Further provided herein is a polypeptide comprising the amino acid sequence of SEQ ID NO: 22. Further provided herein is a polypeptide comprising the amino acid sequence of SEQ ID NO: 23. Further provided herein is a polypeptide comprising the amino acid sequence of SEQ ID NO: 24. Further provided herein is a polypeptide comprising the amino acid sequence of SEQ ID NO: 25. Further provided herein is a polypeptide comprising the amino acid sequence of SEQ ID NO: 26. Further provided herein is a polypeptide comprising the amino acid sequence of SEQ ID NO: 27. Further provided herein is a polypeptide comprising the amino acid sequence of SEQ ID NO: 28. Further provided herein is a polypeptide comprising the amino acid sequence of SEQ ID NO: 29. Further provided herein is a polypeptide comprising the amino acid sequence of SEQ ID NO: 30. Further provided herein is a polypeptide comprising the amino acid sequence of SEQ ID NO: 31. Further provided herein is a polypeptide comprising the amino acid sequence of SEQ ID NO: 32. Further provided herein is a polypeptide comprising the amino acid sequence of SEQ ID NO: 33. Further provided herein is a polypeptide comprising the amino acid sequence of SEQ ID NO: 34. Further provided herein is a polypeptide comprising the amino acid sequence of SEQ ID NO: 35. Further provided herein is a polypeptide comprising the amino acid sequence of SEQ ID NO: 36. Further provided herein is a polypeptide comprising the amino acid sequence of SEQ ID NO: 37. Further provided herein is a polypeptide comprising the amino acid sequence of SEQ ID NO: 38. Further provided herein is a polypeptide comprising the amino acid sequence of SEQ ID NO: 39. Further provided herein is a polypeptide comprising the amino acid sequence of SEQ ID NO: 40. Further provided herein is a polypeptide comprising the amino acid sequence of SEQ ID NO: 41. Further provided herein is a polypeptide comprising the amino acid sequence of SEQ ID NO: 42. Further provided herein is a polypeptide comprising the amino acid sequence of SEQ ID NO: 43. Further provided herein is a polypeptide comprising the amino acid sequence of SEQ ID NO: 44. Further provided herein is a polypeptide comprising the amino acid sequence of SEQ ID NO: 45. Further provided herein is a polypeptide comprising the amino acid sequence of SEQ ID NO: 46. Further provided herein is a polypeptide comprising the amino acid sequence of SEQ ID NO: 47. Further provided herein is a polypeptide comprising the amino acid sequence of SEQ ID NO: 48. Further provided herein is a polypeptide comprising the amino acid sequence of SEQ ID NO: 49. Further provided herein is a polypeptide comprising the amino acid sequence of SEQ ID NO: 50. Further provided herein is a polypeptide comprising the amino acid sequence of SEQ ID NO: 51. Further provided herein is a polypeptide comprising the amino acid sequence of SEQ ID NO: 52. Further provided herein is a polypeptide comprising the amino acid sequence of SEQ ID NO: 53. Further provided herein is a polypeptide comprising the amino acid sequence of SEQ ID NO: 54. Further provided herein is a polynucleotide encoding the polypeptide as described herein. In some embodiments, the polynucleotide comprises at least one sequence selected from the group consisting of SEQ ID NOs: 56-109.

Further provided herein is a vector comprising a polynucleotide encoding a polypeptide comprising the amino acid sequence of any one of SEQ ID NOs: 1-54.

Further provided herein is a panel comprising a plurality of biosensors as described herein. In some embodiments, the panel comprises a composite sensor or an array. In some embodiments, the array is selected from a multichannel array or multiplexed array. In some embodiments, each biosensor comprises the same reporter group. In some embodiments, each biosensor comprises a different reporter group. In some embodiments, the array comprises a plurality of sensor elements, each sensor element comprising a biosensor different from or the same as those of the other sensor elements. In some embodiments, the composite sensor comprises a plurality of sensor elements, each sensor element comprising a mixture of different biosensors. In some embodiments, the composite sensor comprises a single sensor element, the single sensor element comprising a mixture of different biosensors.

Further provided herein is a method of determining the concentration of glucose, galactose, or a combination thereof, in a sample from a subject. The method may include applying the sample to a panel comprising a plurality of biosensors as described herein. In some embodiments, the sample is from a subject. In some embodiments, the sample comprises a biological fluid. In some embodiments, the biological fluid is selected from the group consisting of blood, urine, interstitial fluid, saliva, sweat, tears, gastric lavage, fecal matter, emesis, bile, or combinations thereof. In some embodiments, the sample comprises skin.

Further provided herein is a method of detecting the presence of a ligand in a sample. The method may include a) contacting the biosensor as described herein with the sample; b) measuring a signal from the biosensor; and c) comparing the signal to a ligand-free control, wherein a difference in signal indicates the presence of ligand in the sample, and wherein the ligand is selected from the group consisting of glucose, galactose, and a combination thereof.

Further provided herein is a method of determining the concentration of a ligand in a sample. The method may include a) contacting the biosensor as described herein with the sample; b) measuring a signal from the biosensor; and c) comparing the signal to a standard hyperbolic ligand binding curve to determine the concentration of ligand in the test sample, wherein the standard hyperbolic ligand binding curve is prepared by measuring the signal transduced by the biosensor when contacted with control samples containing known concentrations of ligand, and wherein the ligand is selected from the group consisting of glucose, galactose, and a combination thereof.

Further provided herein is a method of episodically or continuously monitoring the presence of a ligand in a reaction. The method may include a) contacting the biosensor as described herein with the reaction; b) maintaining the reaction under conditions such that the polypeptide is capable of binding ligand present in the reaction; and c) episodically or continuously monitoring the signal from the biosensor in the reaction, wherein the ligand is selected from the group consisting of glucose, galactose, and a combination thereof.

Further provided herein is a method of episodically or continuously monitoring the presence of a ligand in a reaction. The method may include a) contacting the biosensor as described herein with the reaction; b) maintaining the reaction under conditions such that the polypeptide is capable of binding ligand present in the reaction; c) episodically or continuously monitoring the signal from the biosensor in the reaction; and d) comparing the signal to a standard hyperbolic ligand binding curve to determine the concentration of ligand in the test sample, wherein the standard hyperbolic ligand binding curve is prepared by measuring the signal transduced by the biosensor when contacted with control samples containing known concentrations of ligand, wherein the ligand is selected from the group consisting of glucose, galactose, and a combination thereof.

In some embodiments, the biosensor is placed in contact with a subject's skin or mucosal surface. In some embodiments, the biosensor is implanted in a subject's body. In some embodiments, the biosensor is implanted in a subject's blood vessel, vein, eye, natural or artificial pancreas, alimentary canal, stomach, intestine, esophagus, or skin. In some embodiments, the biosensor is configured within or on the surface of a contact lens. In some embodiments, the biosensor is configured to be implanted in the skin. In some embodiments, the biosensor is implanted in a subject with an optode. In some embodiments, the biosensor is implanted in a subject with a microbead. In some embodiments, the biosensor generates the signal transdermally. In some embodiments, the method further includes d) comparing the signal to a ligand-free control, wherein a difference in signal indicates the presence of ligand in the reaction. In some embodiments, the method further includes d) comparing the signal to a standard hyperbolic ligand binding curve to determine the concentration of ligand in the test sample, wherein the standard hyperbolic ligand binding curve is prepared by measuring the signal transduced by the biosensor when contacted with control samples containing known concentrations of ligand. In some embodiments, the sample comprises a fermentation sample. In some embodiments, the sample comprises food or beverage. In some embodiments, the sample comprises a beverage selected from soft drink, fountain beverage, water, coffee, tea, milk, dairy-based beverage, soy-based beverage, almond-based beverage, vegetable juice, fruit juice, fruit juice flavored drink, energy drink, sport drink, and alcoholic product, and combinations thereof. In some embodiments, the sample comprises water selected from flavored water, mineral water, spring water, sparkling water, and tonic water, and combinations thereof. In some embodiments, the sample comprises an alcoholic product selected from beer, malt beverage, liqueur, whiskey, and wine, and combinations thereof. In some embodiments, the sample comprises food comprising a semi-solid or liquid form. In some embodiments, the sample comprises food selected from yogurt, soup, ice cream, broth, purees, shakes, smoothies, batter, condiments, and sauce, and combinations thereof. In some embodiments, the sample is from food engineering.

BRIEF DESCRIPTION OF THE DRAWINGS

FIG. 23 is a schematic map of the polynucleotide sequence (SEQ ID NO: 113 and SEQ ID NO: 114) of an expression vector comprising the polynucleotide sequence encoding the polypeptide sequence of wild-type *E. coli* GGBP (SEQ ID NO: 55) and including poly-histidine polypeptide of sequence GGSHHHHHH (SEQ ID NO: 111).

DETAILED DESCRIPTION

Figure 1:
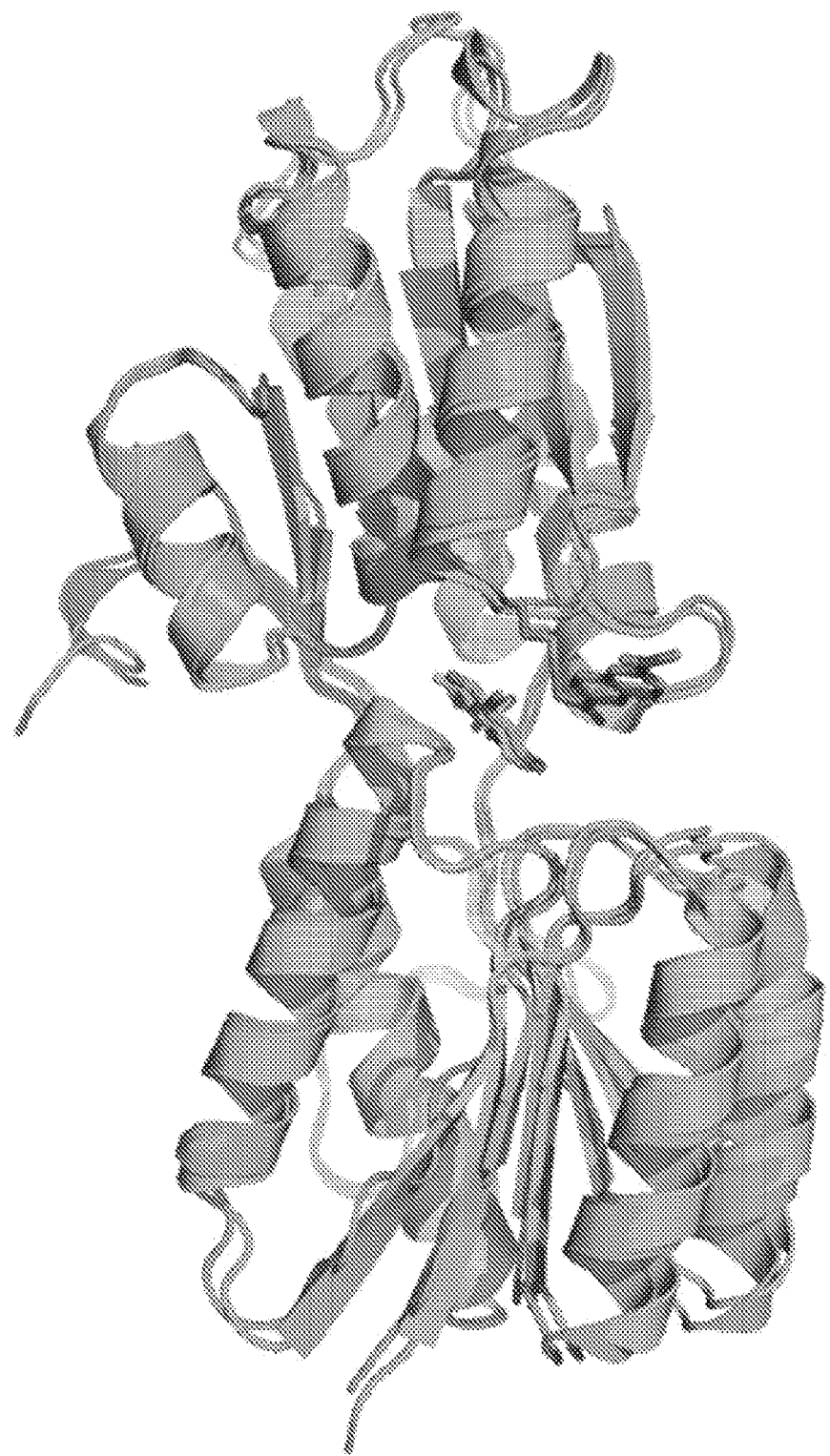
FIG. 1 is a drawing showing the overlay of the wild-type GGBP (turquoise) glucose complex with acrylodan (orange) conjugated to the W183C mutant (green). Calcium (magenta) binds to one of the two protein domains.

Described herein are novel engineered biosensors. These biosensors may have altered ligand-binding affinities, tailored ligand-binding specificities, and/or temperature dependencies of ligand binding or stability. For example, the herein described engineered glucose and galactose biosensors provide high-accuracy information related to extended glucose concentration ranges. The glucose concentration ranges expand over three orders of magnitude and may include the pathophysiological hypo- and hyper-glycemic range in humans. Methods of making these glucose/galactose biosensors, and methods of using these glucose/galactose biosensors are also described herein.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result. The predetermined level may be from a subject or a group or a composition of known ligand concentration. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (Time-dependent ROC curves for censored survival data and a diagnostic marker, Biometrics 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a ligand may be defined in accordance with standard practice.

The term "expression vector" indicates a plasmid, a virus or another medium, known in the art, into which a nucleic acid sequence for encoding a desired protein can be inserted or introduced.

"Food engineering" refers to the multidisciplinary field of applied physical sciences which combines science, microbiology, and engineering for food and related industries. Food engineering includes, but is not limited to, the application of agricultural engineering, mechanical engineering, and chemical engineering principles to food materials to allow for food processing, food machinery, packaging, ingredient manufacturing, instrumentation, and control. For example, food engineering may include the natural sweetening of food products by engineering *Lactococcus lactis* for glucose production, whereby the glucose/galactose biosensors provided herein may be used to intermittently and/or continuously monitor the level of glucose production (see, for example, Pool et al. Metabolic Engineering 2006, 8, 456-464).

The term "host cell" is a cell that is susceptible to transformation, transfection, transduction, conjugation, and the like with a nucleic acid construct or expression vector. Host cells can be derived from plants, bacteria, yeast, fungi, insects, animals, etc.

"Ligand" refers to the entity whose presence and/or concentration may be determined using the biosensor. Accordingly, a ligand may also be referred to as a substrate or analyte. As used herein, the ligand comprises glucose, galactose, or a combination thereof. In some embodiments, the ligand comprises glucose. In some embodiments, the ligand comprises galactose. In some embodiments, the ligand may be a modified glucose or galactose, such as, for example, glucose or galactose including a label such as a radioactive or fluorescent label.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of amino acids and can be natural, synthetic, or a modification or combination of natural and synthetic. Peptides and polypeptides include proteins such as binding proteins. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units.

"Sample" or "test sample" as used herein can mean any sample in which the presence and/or level of glucose and/or galactose is to be detected or determined. Samples may include liquids, solutions, emulsions, or suspensions. Samples may include a reaction for episodic or continuous monitoring. Samples may include industrial samples such as from food industry or food engineering. Samples may include fermentation samples, food, or beverages. Food and beverage may include any edible and/or potable liquid, solution, emulsion, or suspension. Food may comprise a semi-solid or liquid form. Food may include, for example, yogurt, soup, ice cream, broth, purees, shakes, smoothies, batter, condiments, sauce, and combinations thereof. Beverages may include, for example, soft drinks, fountain beverages, waters, coffee, tea, milk, dairy-based beverages, soy-based beverages, almond-based beverages, vegetable juice, fruit juice, fruit juice flavored drinks, energy drinks, sport drinks, or alcoholic products, and combinations thereof. Waters may include, for example, flavored water, mineral water, spring water, sparkling water, and tonic water, and combinations thereof. Alcoholic products may include, for example, beer, malt beverages, liqueurs, whiskeys, or wine, and combinations thereof. In some embodiments, the sample includes a glucose-containing beverage. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchioalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In some embodiments, the sample comprises skin (e.g., transdermal glucose monitoring). In other embodiments, the sample comprises a biological fluid. Samples can be obtained by any means known in the art.

By "specifically binds," it is generally meant that a polypeptide or biosensor, or derivative thereof, binds to a cognate ligand or analyte in preference to a random, unrelated ligand or interferent.

"Subject" as used herein refers to any subject, particularly a mammalian subject, who wants to or is in need of detecting ligand or determining the concentration of ligand with the herein described biosensors. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Variant" used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Biosensor

Biosensors are molecular recognition elements that transduce ligand-binding events into physical signals. Biosensors as detailed herein bind at least one ligand and emit a signal. A ligand-bound biosensor results in a signal that is different from the unbound biosensor. This difference facilitates detection of the at least one ligand and/or determination of ligand concentration. The biosensors may be used without the assistance of other reagents. The measuring or detecting process does not change the composition of the sensor, unlike enzyme-based or competitive displacement assays. The biosensor comprises a polypeptide and at least one reporter group. The polypeptide may have one or more mutations as compared to a corresponding wild-type polypeptide.

a. Polypeptide

According to the compositions and methods detailed herein, the polypeptide comprises a mutant glucose-galactose binding protein (GGBP) from *Escherichia coli*. GGBP is a member of the bacterial periplasmic binding protein (PBP) superfamily that mediates chemotaxis and uptake of a wide variety of chemical species, including sugars, amino acids, oligopeptides, and metals. PBPs include two domains connected by a hinge region, with a ligand binding site located at the interface between the two domains. The ligand binding site can adopt two different conformations: a ligand-free open form, and a ligand-bound closed form. The ligand-free open form and ligand-bound closed form interconvert through a bending motion around the hinge.

In some embodiments, the polypeptide comprises at least one mutation compared to a wild-type glucose-galactose binding protein from *Escherichia coli*. In some embodiments, the wild-type glucose-galactose binding protein from *Escherichia coli* is encoded by a polynucleotide of SEQ ID NO: 110 and comprises an amino acid sequence of SEQ ID NO: 55. In some embodiments, the wild-type glucose-galactose binding protein from *Escherichia coli* comprises an amino acid sequence of SEQ ID NO: 112. SEQ ID NO: 112 corresponds to SEQ ID NO: 55 without the starting methionine.

The polypeptide includes at least one binding site for at least one ligand. The polypeptide binds the at least one ligand. In some embodiments, the polypeptide binds a single ligand. In some embodiments, the polypeptide binds two ligands.

In some embodiments, the polypeptide may include a purification tag. The purification tag may comprise, for example, poly-histidine, glutathione-S-transferase (GST), poly-glutamate, calmodulin, FLAG, Xpress, and combinations thereof. The purification tag may be present at the C-terminus of the polypeptide, the N-terminus of the polypeptide, an internal location in the amino acid sequence of the polypeptide, or a combination thereof. In some embodiments, the polypeptide comprises a purification tag comprising a poly-histidine polypeptide of sequence GGSHHHHHH (SEQ ID NO: 111).

i. Mutations

The polypeptide comprises at least one mutation as compared to wild-type *E. coli* GGBP (SEQ ID NO: 112). SEQ ID NO: 112 corresponds to SEQ ID NO: 55 without the starting methionine. The numbering of the mutations corresponds to the numbering of the amino acids in SEQ ID NO: 112. In some embodiments, the polypeptide comprises one or more mutations as compared to wild-type *E. coli* GGBP (SEQ ID NO: 112). In some embodiments, the polypeptide comprises two or more mutations as compared to wild-type *E. coli* GGBP (SEQ ID NO: 112).

1) Affinity-Tuning

The polypeptides as detailed herein include at least one mutation that alters the ligand binding affinity of the polypeptide. In some embodiments, the affinity-altering mutations include changes to amino acids in the ligand binding site. The affinity-altering mutations may mutate an amino acid that interacts with a portion of the ligand. When the ligand is glucose, the interaction affected may be between the amino acid and a portion of the glucose molecule including, for example, 1-hydroxyl, 2-hydroxyl, 3-hydroxyl, 4-hydroxyl, 6-hydroxyl, pyranose ring, and combinations thereof. The affinity-altering mutations may mutate an amino acid that interacts with the reporter group. The affinity-altering mutations may mutate an amino acid that interacts with a water molecule.

Mutations that alter the GGBP glucose affinity while enabling the extension of high accuracy coverage in the hyperglycemic to hypoglycemic concentration ranges can be divided into three classes: (Class A) mutations that impact the direct interactions of the GGBP with the glucose hydroxyls and/or pyranose ring; (Class B) mutations that impact the interaction of the GGBP with the fluorophore; and/or (Class C) mutations that impact the interaction of the GGBP with the buried water molecule present in the fluorescent conjugate, but not the wild-type protein. These mutations can be constructed by site-directed mutagenesis, total gene synthesis or semi-synthesis, with specific residues being mutated.

Class A mutations include those of, for example, polypeptides GGBP183C (SEQ ID NO: 1), GGBP16C (SEQ ID NO: 2), GGBP183C14A (SEQ ID NO: 3), GGBP183C152N (SEQ ID NO: 4), GGBP183C152F (SEQ ID NO: 5), and GGBP183C152Q (SEQ ID NO: 6).

Class B mutations include those of, for example, polypeptides GGBP183C149Q (SEQ ID NO: 7), GGBP183C149S (SEQ ID NO: 8), and GGBP183C149K (SEQ ID NO: 9).

Class C mutations include those of, for example, polypeptides GGBP183C155N (SEQ ID NO: 10) and GGBP183C155H (SEQ ID NO: 11).

The affinity-altering mutation may result in a biosensor having an affinity ($K_D$) for ligand within the physiological range of the ligand in a subject. The physiological range of the ligand in a subject may include normal or healthy levels. When the ligand comprises glucose, the physiological range of the ligand in a subject may include normal ranges, hypoglycemic ranges hyperglycemic ranges, and hyperglycemic-hyperosmotic ranges of glucose.

The normal range of glucose concentration in blood for humans may be about 60 mg/dL to about 140 mg/dL, 100 mg/dL to about 140 mg/dL, or about 60 mg/dL to about 90 mg/dL. The hypoglycemic range for humans may be less than about 3.9 mM, less than about 3.3 mM, less than about 2.8 mM, less than about 2.2 mM, less than about 70 mg/dL, less than about 60 mg/dL, less than about 50 mg/dL, or less than about 40 mg/dL. The hyperglycemic range for humans may be greater than about 20 mM, greater than about 15 mM, greater than about 11.1 mM, greater than about 7 mM, greater than about 5.6 mM, greater than about 300 mg/dL, greater than about 250 mg/dL, greater than about 200 mg/dL, greater than about 126 mg/dL, or greater than about 100 mg/dL. The hyperosmolar-hypoglycemic range for humans may be greater than about 600 mg/dL. In some embodiments, the biosensor is able to detect glucose in a concentration range of about 2-4 mM (hypoglycemic) to about 10-33 mM (hyperglycemic) to greater than about 33 mM (hyperosmolar-hypoglycemic). The concentration of glucose in the blood may also be referred to as blood sugar level.

In some embodiments, the biosensor has an affinity ($K_D$) for glucose within the physiological range of the ligand in a subject. In some embodiments, the biosensor has an affinity ($K_D$) for glucose of about 0.2 mM to about 100 mM. In some embodiments, the biosensor is capable of detecting glucose in the range of about 0.1 mmol/L to about 120 mmol/L. In some embodiments, the biosensor is capable of detecting glucose in the range of about 4 mmol/L to about 33 mmol/L.

In some embodiments, the biosensor has an affinity ($K_D$) for galactose within the physiological range of the ligand in a subject. In some embodiments, the biosensor has an affinity ($K_D$) for galactose of about 0.8 mM to about 100 mM, or about 1 mM to about 90 mM. In some embodiments, the biosensor is capable of detecting galactose in the range of about 0.2 mmol/L to about 400 mmol/L or about 0.5 mmol/L to about 300 mmol/L.

In some embodiments, a single biosensor has an affinity ($K_D$) for glucose and/or galactose within the physiological range of the ligand in a subject. In some embodiments, a plurality of biosensors together has an affinity ($K_D$) for glucose and/or galactose within the physiological range of the ligand in a subject, wherein each biosensor has an affinity ($K_D$) for glucose and/or galactose within a portion of the physiological range of the ligand in a subject.

In some embodiments, the polypeptide includes a mutation to an amino acid selected from the group consisting of Y10, D14, F16, N91, K92, E149, H152, D154, A155, R158, M182, N211, D236, and N256, and combinations thereof. In some embodiments, the polypeptide includes a mutation selected from Y10A, D14A, D14Q, D14N, D14S, D14T, D14E, D14H, D14L, D14Y, D14F, F16L, F16A, N91A, K92A, E149K, E149Q, E149S, H152A, H152F, H152Q, H152N, D154A, D154N, A155S, A155H, A155L, A155F, A155Y, A155N, A155K, A155M, A155W, A155Q, R158A, R148K, M182W, N211F, N211W, N211K, N211Q, N211S, N211H, N211M, D236A, D236N, N256A, and N256D, and combinations thereof. In some embodiments, the polypeptide comprises an amino acid sequence of any one of SEQ ID NOs: 1-54. In some embodiments, the polypeptide is encoded by a polynucleotide sequence of any one of SEQ ID NOs: 56-109.

Affinity of the polypeptide for ligand may be determined by any means known by one of skill in the art. Affinity may be defined by $K_D$. Affinity may be determined as exemplified in Example 3. In some embodiments, biosensor function may be assessed using fluorescence emission biosensors recorded in the absence and presence of saturating ligand concentrations. Spectral changes may be characterized by four parameters: wavelength shift (the difference between the wavelengths of emission maximum in the unbound and ligand-saturated states), direction of intensity change (increase or decrease in intensity at the wavelengths of maximum emission in the two states), standard intensity change ($\Delta I_{std}$), and standard ratiometric change ($\Delta R$). $\Delta I_{std}$ is defined as the normalized intensity change relative to the average intensity, determined at the wavelength mid-point between the two emission maxima:

$$\Delta I_{std} = \left| \frac{2(I_1(\lambda_{std}) - I_2(\lambda_{std}))}{I_1(\lambda_{std}) + I_2(\lambda_{std})} \right| \qquad 35$$

where $\Delta I_{std} = (\lambda_{max,\ unbound} + \lambda_{max,\ saturated})/2$ and $I_1$, $I_2$ are the fluorescence intensities at $\lambda_{std}$ of each spectrum respectively. $\Delta R$ is defined in terms of two emission bands, $A_1([\lambda_1, \lambda_2])$ and $A_2[\lambda_3, \lambda_4]$:

$$\Delta R = \left| \frac{^0A_1}{^0A_2} - \frac{^\infty A_1}{^\infty A_2} \right| \qquad 36$$

where $^0A_1$, $^\infty A_2$ are the areas in the absence of ligand, and $^0A_1$, $^\infty A_2$ the areas in the presence of saturating ligand. A computer program may be used to enumerate $\Delta R$ for all possible pairs of wavelength bands in the two spectra, to identify the optimal sensing condition, defined as the maximum value of $\Delta R$. Adjustable parameters of the algorithm, and their values used for $\Delta R_{max}$ quantities reported may include: step size (2 nm), step width (10 nm), minimum integration area limit (fraction of total: 0.1), and maximum integration area limit (fraction of total: 1). Affinity of a biosensor for a ligand may be determined by fluorimetric titration. The emission wavelength monitored may be that of maximum difference in intensity between the ligand-free and bound states. For each biosensor, fluorescence intensiometric observations may be fit to a hyperbolic binding isotherm for a two-state model (Marvin et al., Proc. Natl. Acad. Sci. USA 1997, 94, 4366-4371):

$$F = \frac{K_d F_F + [S] F_B}{K_d + [S]} \qquad 37$$

where F is fluorescence at ligand concentration [S], $K_d$ is the dissociation constant, and $F_F$, $F_B$ are the fluorescence intensities of the ligand-free and ligand-saturated states, respectively. For ratiometric observations, equation 37 may be modified to account for differentially weighted contributions of the two emission bands (Lakowicz, Principles of Fluorescence Spectroscopy, $2^{nd}$ Ed. Kluwer Academic Press, New York, p. 698, 1999):

$$R = \frac{app K_d R_F + [S] R_B}{app K_d + [S]} \qquad 38$$

where R is ratio $A_1/A_2$, $R_B = {}^\infty A_1/{}^\infty A_2$, $R_F = {}^0A_1/{}^0A_2$, and $^{app}K_d$ is an apparent dissociation constant:

$$^{app}K_d = \frac{^0A_2}{^\infty A_2} K_d \qquad 39$$

2) Cysteine

In some embodiments, the polypeptides as detailed herein comprise at least one cysteine. As wild-type *E. coli* GGBP (SEQ ID NO: 55 or 112) does not include any cysteine residues, the polypeptides may include at least one mutation replacing an amino acid with a cysteine.

In some embodiments, phenylalanine-16 is mutated to or replaced with a cysteine (F16C). When the polypeptide consists of a single mutation relative to wild-type *E. coli*

GGBP (SEQ ID NO: 112), the single mutation is F16C. In some embodiments, tryptophan-183 is mutated to or replaced with a cysteine (W183C).

In some embodiments, the cysteine provides a thiol for conjugation of a reporter group.

b. Reporter Group

The biosenor comprises at least one reporter group conjugated to the polypeptide. "Reporter" and "reporter group" and "label" are used interchangeably herein. The reporter is capable of generating a detectable signal. A variety of reporter groups can be used, differing in the physical nature of signal transduction (e.g., fluorescence, electrochemical, nuclear magnetic resonance (NMR), and electron paramagnetic resonance (EPR)) and in the chemical nature of the reporter group. In some embodiments, the signal from the reporter is a fluorescent signal. Preferably, the reporter group used will form bonds (e.g., thioester bonds) that will remain stable under conditions required for biosensor manufacturing, distribution, and deployment.

The reporter may comprise a fluorophore. Examples of fluorophores include, but are not limited to, acrylodan, badan, rhodamine, naphthalene, danzyl aziridine, 4-[N-[(2-iodoacetoxy)ethyl]-N-methylamino]-7-nitrobenz-2-oxa-1,3-diazole ester (IANBDE), 4-[N-[(2-iodoacetoxy)ethyl]-N-methylamino-7-nitrobenz-2-oxa-1,3-diazole (IANBDA), fluorescein, dipyrrometheneboron difluoride (BODIPY), 4-nitrobenzo[c][1,2,5]oxadiazole (NBD), Alexa fluorescent dyes, and derivatives thereof. Fluorescein derivatives may include, for example, 5-fluorescein, 6-carboxyfluorescein, 3'6-carboxyfluorescein, 5(6)-carboxyfluorescein, 6-hexachlorofluorescein, 6-tetrachlorofluorescein, fluorescein, and isothiocyanate. In some embodiments, the reporter group comprises the thiol-reactive acrylodan (6-acryloyl-2-dimethylaminonaphthalene). In other embodiments, the reporter group comprises thiol-reactive badan (6-bromoacetyl-2-dimethylamino-naphthalene).

In some embodiments, the reporter is sensitive to its local environment and exhibits changes in spectral parameters such as intensity and/or emission wavelength depending on factors such as, for example, the degree of solvent exclusion, and the effective dielectric constant of the environment. The fluorescence emission peak and intensity of the acrylodan and badan conjugates are particularly sensitive to conformational changes or ligand binding, making these dyes some of the most useful thiol-reactive probes for reagentless fluorescent biosensor construction.

The reporter may be conjugated to a natural amino acid or a natural amino acid of the polypeptide. The reporter group(s) can be positioned in the glucose-binding pocket of the GGBP as defined by its three-dimensional structure (Vyas et al., *Nature* 1987, 327, 635-638; Vyas et al., *Science* 1988, 242, 1290-1295; Vyas et al., *Biochemistry* 1994, 33, 4762-4768), so that changes in reporter signal are a consequence of direct interactions with the bound glucose (endosteric positions), at the periphery of the binding site (peristeric positions) where localized changes in the protein structure in response to ligand binding are sensed, or at some distance way where the reporter group(s) senses glucose binding indirectly via an allosteric coupling mechanism (allosteric positions) (DeLorimier et al., *Prot. Sci.*, 2002, 2655-2675). In some embodiments, the reporter is conjugated to a cysteine of the polypeptide. In some embodiments, the reporter is covalently conjugated to the polypeptide via maleimide functional group bound to a cysteine (thiol) on the polypeptide. In some embodiments, the reporter group is attached to a cysteine residue at the endosteric position 183. In other embodiments, the reporter group is attached to a cysteine residue at the endosteric position 16. In some embodiments, the reporter is conjugated to F16C. In some embodiments, the reported is conjugated to W183C.

c. Signal

Binding of ligand mediates conformational changes in the biosensor, such as hinge-bending motions of the polypeptide. The conformational changes affect the environment of the reporter such that a change in the reporter-generated signal occurs. That is, without ligand bound, the biosensor results in signal generated from the reporter, and when ligand is bound, the signal generated from the reporter changes. The ligand-bound biosensor results in a reporter-generated signal that is different from the unbound biosensor.

1) Single Wavelength or Range

In some embodiments, the signal comprises the emission intensity of the fluorophore recorded at a single wavelength or range of wavelengths. The change in signal may be a shift in the single wavelength or range of wavelengths. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, or at least about 100 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 100 nm.

2) Two Wavelengths or Ranges

In certain embodiments, the signal comprises the ratio of the emission intensities recorded at two distinct wavelengths or ranges of wavelengths. The change in signal may be decreased emission intensity at one wavelength, and no change in emission intensity at the other wavelength. The change in signal may be increased emission intensity at one wavelength, and no change in emission intensity at the other wavelength. The change in signal may be increased emission intensity at one wavelength, and increased emission intensity at the other wavelength. The change in signal may be decreased emission intensity at one wavelength, and decreased emission intensity at the other wavelength. The change in signal may be increased emission intensity at one wavelength, and decreased emission intensity at the other wavelength. In some embodiments, the change in ratio of the emission intensities recorded at two distinct wavelengths or ranges of wavelengths may be at least about 1.1-fold, at least about 1.2-fold, at least about 1.4-fold, at least about 1.6-fold, at least about 1.8-fold, at least about 2.0-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 12-fold, at least about 14-fold, at least about 16-fold, at least about 18-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold.

The change in signal may be a change in the ratio of the two distinct wavelengths or ranges of wavelengths. The change in signal may be a shift in the two distinct wavelengths or ranges of wavelengths. In some embodiments, one wavelength shifts. In some embodiments, both wavelengths shift. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, or at least about 100 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 100 nm.

3. Polynucleotide

Further provided are polynucleotides encoding the polypeptides detailed herein. A vector may include the polynucleotide encoding the polypeptides detailed herein. To obtain expression of a polypeptide, one typically subclones the polynucleotide encoding the polypeptide into an expression vector that contains a promoter to direct transcription, a transcription/translation terminator, and if for a nucleic acid encoding a protein, a ribosome binding site for translational initiation. Suitable bacterial promoters are well known in the art and described (e.g., in Sambrook et al., and Ausubel et al., supra). Bacterial expression systems for expressing the protein are available in, e.g., *E. coli, Bacillus* sp., and *Salmonella* (Paiva et al., Gene 1983, 22, 229-235; Mosbach et al., Nature 1983, 302, 543-545). Kits for such expression systems are commercially available. Eukaryotic expression systems for mammalian cells, yeast, and insect cells are well known in the art and are also commercially available. Retroviral expression systems can be used in the present invention. An example of an expression vector encoding wild-type *E. coli* GGBP is shown in FIG. 23. In some embodiments, the polypeptide comprises an amino acid sequence of any one of SEQ ID NOs: 1-54. In some embodiments, the polypeptide is encoded by a polynucleotide sequence of any one of SEQ ID NOs: 56-109.

4. Single Biosensor

In some embodiments, the methods and compositions include a plurality of a single type of biosensor. The biosensors may be identical in structure and function. For example, the biosensors of a single type may have the same polypeptide, the same reporter, and the same ligand affinity.

5. Panel

In other embodiments, the methods and compositions include a plurality of different types of biosensors. A plurality of these different types of biosensors may be arranged or incorporated in a panel. As used herein, a "panel" refers to two or more biosensors. The two or more biosensors may be different from each other. The biosensors may differ in structure and/or function. Biosensors may differ in polypeptide sequence, reporter, ligand affinities, or a combination thereof. Accordingly, there may be different types of biosensors. In some embodiments, each biosensor in the panel comprises the same reporter group. In some embodiments, each biosensor in the panel comprises a different reporter group. The panel may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, or at least 100 biosensors.

The panel of biosensors includes at least one sensor element. "Sensor element" refers to a single spot, site, location, or well for the at least one biosensor, to which a sample or aliquot thereof may be applied. The panel may be a composite sensor or an array.

a. Composite Sensor

In some embodiments, the panel is a composite sensor. In a composite sensor, each sensor element includes a mixture of two or more different biosensors. In some embodiments, the composite sensor includes one sensor element. In some embodiments, the composite sensor includes two or more sensor elements. In some embodiments, signals are measured from a composite sensor in which the signals arise from one or more biosensors in the sensor element. For example, signals may be measured from a composite sensor in which the signals arise from a subset of the total number of biosensors in the sensor element. For example, signals may be measured from a composite sensor in which the signals arise from two of five biosensors in the sensor element.

b. Array

In some embodiments, the panel is an array. In an array, each sensor element includes a single type of biosensor. An array comprises a plurality of individually and spatially localized sensor elements. Each sensor element includes a biosensor that is different than or the same as the biosensor of a different sensor element. In some embodiments, signals are measured from an array in which the signals arise separately from two or more selected biosensors in separate sensor elements. An array may comprise a plurality of sensor elements of a variety of sizes and configurations. An array may comprise a plurality of sensor elements arranged linearly. For example, an array may comprise a plurality of micrometer-sized sensor elements arranged in a single row.

An array may comprise a plurality of sensor elements arranged in a grid. The grid may be two- or three-dimensional. In some embodiments, the grid is a spatially addressable grid. In some embodiments, the biosensors are incorporated into an array, such as a multichannel or multiplexed array.

6. Administration

The biosensors of the present disclosure can be used in any setting where glucose detection is required or desired, such a medical setting (e.g., determining the level of blood glucose in a subject), biological setting (e.g., determining the presence or amount of glucose in a reaction), or in process engineering, such as monitoring the amount of glucose in a fermentation reaction (e.g., beer/wine production, etc.). Other examples include, but are not limited to, uses in the food industry (Suleiman et al, In: Biosensor Design and Application: Mathewson and Finley Eds; American Chemical Society, Washington, D.C. 1992, vol. 511); in clinical chemistry (Wilkins et al., *Med. Eng. Phys.* 1996, 18, 273-288; Pickup, *Tr. Biotech.* 1993, 11, 285-291; Meyerhoff et al., *Endricon* 1966, 6, 51-58; Riklin et al., *Nature* 1995, 376, 672-675); Willner et al., *J. Am. Chem. Soc.* 1996, 118, 10321-10322); as the basis for the construction of a fluorescent flow cell containing immobilized GGBP-FAST conjugates (see, e.g., Wilkins et al., *Med. Eng. Phys.* 1966, 18, 273-288; Pickup, *Tr. Biotech.* 1993, 11, 285-291; Meyerhoff et al., *Endricon.* 1966, 6, 51; Group, *New Engl. J. Med.* 1993, 329, 977-986; Gough et al., *Diabetes* 1995, 44, 1005-1009); and in an implantable devices, such as those suitable for use as an artificial pancreas.

The biosensors as detailed herein may be administered in a variety of ways known by those of skill in the art, as appropriate for each application. Biosensors may be provided in a solution. The solution may be buffered. Biosensors may be provided in a solution and mixed directly with a sample. Biosensors may be immobilized within a disposable cartridge into which a sample may be introduced or applied. Biosensors may be implanted or incorporated in a wearable device. The biosensor may be provided as an optode.

a. Wearable Device

The biosensor may be attached to or incorporated in a wearable device. Wearable devices may include, for example, adhesive strips, patches, and contact lenses. The biosensor may be configured for placement in contact with a subject's skin or mucosal surface. In some embodiments, the biosensor is configured as an adhesive strip. In some embodiments, the biosensor is configured within or on the surface of a contact lens. In some embodiments, the contact lens is formed from a transparent substrate shaped to be worn directly over a subject's eye, as described in, for example, U.S. Pat. No. 8,608,310.

b. Implant

The biosensor may be implanted. The biosensor may be implanted in a subject's body. The biosensor may be implanted in a subject's blood vessel, vein, eye, natural or artificial pancreas, skin, or anywhere in the alimentary canal including the stomach, intestine and esophagus. The biosensor may be implanted in a subject with a microbead. In some embodiments, the biosensor is configured to be implanted in the skin. The biosensor may be implanted in a subject sub-dermally. The biosensor may generate the signal transdermally. In some embodiments, the biosensor may be implanted in a subject with transdermal microbeads, wherein the optical signals can be transmitted remotely between the biosensor and detecting device.

c. Optode

In some embodiments, the biosensor is administered as an optode. As used herein, "optode" refers to an optical fiber with a single biosensor, or a composite biosensor, immobilized at the surface or at the end. An "optode" may also be referred to as an "optrode." In some embodiments, the biosensor is implanted in a subject as an optode. The optode may be incorporated with or into a needle. The optode may be incorporated with a probe such as endoscopy or colonoscopy probes. The optode may be used in a tumor, near a tumor, or at the periphery of a tumor. In some embodiments, the biosensor may be implanted in a subject as an optode, wherein the optical signals can be transmitted between the biosensor and detecting device using physical links. In some embodiments, the biosensor is administered as an optode to a sample or reaction. The optode may be contacted with a sample or reaction. In some embodiments, an optode is used to continuously or episodically monitor a ligand in a sample or reaction.

7. Methods

Provided herein are methods of detecting the presence of a ligand, methods of determining the concentration of a ligand, methods of monitoring the presence of a ligand, and methods of making a biosensor. The biosensors and methods described herein may be used in conjunction with surgery. The biosensors and methods described herein may be used in conjunction with anesthesia. The biosensors and methods described herein may be used in conjunction with dialysis. The biosensors and methods described herein may be used in conjunction with in-line monitoring. In-line monitoring may include removing a sample from a patient, transporting the sample via tubing to a biosensor external to the subject's body to measure a signal from the biosensor, and returning the sample back to the subject via tubing.

a. Methods of Detecting the Presence of a Ligand

Provided herein is a method of detecting the presence of a ligand in a sample. The method may include contacting the biosensor with the sample; measuring a signal from the biosensor; and comparing the signal to a ligand-free control. A difference in signal indicates the presence of ligand in the sample.

Provided herein is a method of detecting the presence of glucose in a sample. The method may include (a) providing a glucose biosensor according to any of the previous claims in which the reporter group is attached the GGBP so that a signal transduced by the reporter group when the GGBP is bound to glucose differs from a signal transduced by the reporter group when the GGBP is not bound to glucose; (b) contacting the biosensor with the test sample under conditions such that the biosensor can bind to glucose present in the test sample; and (c) comparing the signal transduced by the reporter group when the biosensor is contacted with the test sample with the signal transduced by the reporter group when the biosensor is contacted with a glucose-free control sample, wherein a difference in the signal transduced by the reporter group when the biosensor is contacted with the test sample, as compared to when the biosensor is contacted with the control sample, indicates that the test sample contains glucose.

b. Methods of Determining the Concentration of a Ligand

Provided herein is a method of determining the concentration of a ligand in a sample. The method may include contacting the biosensor with the sample; measuring a signal from the biosensor; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of determining the concentration of glucose in a test sample comprising, consisting of, or consisting essentially of: (a) providing a glucose biosensor comprising a glucose biosensor as described herein in which the reporter group is attached the GGBP so that a signal transduced by the reporter group when the GGBP is bound to glucose differs from a signal transduced by the reporter group when the GGBP is not bound to glucose; (b) contacting the biosensor with the test sample under conditions such that the biosensor can bind to glucose present in the test sample; and (c) comparing the signal transduced by the reporter group when the biosensor is contacted with the test sample with a standard hyperbolic glucose binding curve prepared by measuring the signal transduced by the reporter group when the biosensor is contacted with control samples containing known quantities of glucose to determine the concentration of glucose in the test sample.

c. Methods of Monitoring the Presence of a Ligand

The present invention is directed to a method of episodically or continuously monitoring the presence of a ligand in a reaction. In certain embodiments, the biosensors may be used in the continuous monitoring of glucose in a reaction. In certain embodiments, the glucose sensors may be used in episodic monitoring of sample aliquots. For example, aliquots of physiological fluids can be analyzed point-of-care or in a laboratory setting.

The method of episodically or continuously monitoring the presence of a ligand in a reaction may include contacting the biosensor with the reaction; maintaining the reaction under conditions such that the polypeptide is capable of binding ligand present in the reaction; and episodically or continuously monitoring the signal from the biosensor in the reaction.

The method of episodically or continuously monitoring the presence of a ligand in a reaction may include contacting the biosensor with the reaction; maintaining the reaction under conditions such that the polypeptide is capable of binding ligand present in the reaction; episodically or continuously monitoring the signal from the biosensor in the reaction; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

In some embodiments, the method further includes comparing the signal to a ligand-free control, wherein a difference in signal indicates the presence of ligand in the reaction.

In some embodiments, the method further includes comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of continuously monitoring the presence of glucose in a reaction comprising, consisting of, or consisting essentially of: (a) providing a glucose biosensor as described herein in which the reporter group is attached the GGBP so that a signal transduced by the reporter group when the GGBP is bound to glucose differs from a signal transduced by the reporter group when the GGBP is not bound to glucose; (b) maintaining the biosensor within the reaction and under conditions such that the biosensor can bind to glucose present in the reaction; (c) continuously monitoring the signal transduced by the reporter group when the biosensor is contacted with the glucose present in the reaction; and optionally (d) comparing the signal transduced by the reporter group when the biosensor is contacted with the glucose present in the reaction with the signal transduced by the reporter group when the biosensor is contacted with a glucose-free control sample, wherein a difference in the signal transduced by the reporter group when the biosensor is contacted with the glucose present in the reaction, as compared to when the biosensor is contacted with the control sample, indicates glucose is present in the reaction.

Yet another aspect of the present disclosure provides a method of continuously monitoring the concentration of glucose in a reaction comprising, consisting of, or consisting essentially of: (a) providing a glucose biosensor comprising a glucose biosensor as described herein in which the reporter group is attached the GGBP so that a signal transduced by the reporter group when the GGBP is bound to glucose differs from a signal transduced by the reporter group when the GGBP is not bound to glucose; (b) maintaining the biosensor within the reaction under conditions such that the biosensor can bind to glucose present in the reaction; and (c) continuously monitoring the signal transduced by the reporter group when the biosensor is contacted with the glucose present in the reaction; and (d) comparing the signal transduced by the reporter group when the biosensor is contacted with the glucose present in the reaction with a standard hyperbolic glucose binding curve prepared by measuring the signal transduced by the reporter group when the biosensor is contacted with control samples containing known quantities of glucose to determine the concentration of glucose in the reaction.

d. Method of Making a Biosensor

Further provided herein is a method of making a biosensor comprising a binding protein and a fluorophore to form a binding protein-conjugate, the method comprising, consisting of, or consisting essentially of: (1) determining the structure of the binding protein; (2) characterizing the thermodynamic properties of the binding protein-conjugate bound to the ligand; (3) generating engineered binding proteins comprising at least one mutation by performing mutagenesis studies to alter the interactions between the protein and one or more of the fluorophore, direct contacts with the bound ligand, indirect contacts with the bound ligand, and inter-domain contacts that change upon ligand binding; (4) repeating or successively iterating steps (1) and/or (2) and/or (3); and (5) selecting those binding proteins comprising at least one mutation that exhibit the desired properties for use as a biosensor.

Further provided herein is a method of making a glucose biosensor from a glucose-galactose binding protein comprising, consisting of, or consisting essentially of: (1) determining the structure of a glucose-galactose binding protein (GGBP); (2) characterizing the thermodynamic properties of the GGBP by determining the fluorescent response as a function of glucose concentration, calcium concentration, and temperature; (3) generating GGPBs comprising at least one mutation by performing mutagenesis studies to alter the direct interactions between the protein and fluorophore, direct contacts with bound glucose, indirect contacts with bound glucose, and inter-domain contacts that are present in the ligand-bound, but not the ligand-free protein; (4) repeating or successively iterating steps (1) and/or (2) and/or (3); and (5) selecting those glucose binding proteins comprising at least one mutation that exhibit the desired properties for use as a glucose biosensor.

In some embodiments, the structure of the binding protein may already be known. In such cases, one may then begin characterizing the thermodynamic properties of the binding protein immediately. In other embodiments, the structure of the binding protein, e.g., GGBP protein, is determined through any means known to those skilled in the art, such as X-ray crystallography or Nuclear Magnetic Resonance. In such embodiments, a three-dimensional coordinate set representing the atomic or near-atomic structure of the fluorescent protein conjugate bound to ligand is generated. For example, using such a method, the structural analysis of the GGBP183C-acrylodan conjugate glucose biosensor revealed four essential findings: (1) the structure of amino acid backbone of the GGBP183C-acrylodan in the closed formation is largely indistinguishable from that of the wild-type protein bound to glucose; (2) the conjugated acrylodan points out of the glucose-binding site, vacating the position that was occupied by tryptophan 183 in the wild-type protein; (3) in the conjugate, a buried water molecule replaces the tryptophan 183 indole ring; (4) acrylodan interacts with protein residues outside the glucose binding site (5) the salt bridge between residues E149 and K92 in the wild-type protein is broken, resulting in a potentially unfavorable interaction between the carboxylate of E149 and a carbonyl moiety in the acrylodan conjugate.

For a fluorescent conjugate, a thermodynamic model is developed that describes the dependence of the fluorescence response of the glucose biosensor to glucose, galactose, calcium, and temperature. The thermodynamic model is developed to (i) provide a quantitative, precise and accurate description of the fluorescence landscape (response) as a function of glucose concentration, calcium concentration, and temperature; and (ii) provide an accurate description of any potential systematic errors in the glucose-dependent signal arising from variations in temperature or calcium concentration on pathophysiological ranges. Development of such a model comprises a means for fluorescent landscape data collection, such as a Tecan Genesis liquid handling robot, that allows for the precise titration series that finely sampled in a geometric (logarithmic) progression, and computer algorithms for analyzing the data. The data collection means further allows for the measurement of fluorescence emission intensities of the GGBP-conjugate in the presence of glucose, calcium, etc. and combinations thereof as a function of temperature.

For example, using such a model on GGBP183C-acrylodan, the model revealed several mechanistic features that are relevant to the utilization of some of the glucose biosensors described herein in a continuous glucose monitoring optrode: (1) the glucose affinity exhibits significant temperature dependence; (2) the temperature dependence varies the glucose concentration relative to that measured at 37° C. at a given signal level by ±3.7% in the diurnal temperature range (36-38° C.) and −7.4% to +18.5% over the pathophysiological range of 35-42° C.; (3) quantitative description of this behavior combined with measurement of the temperature enables high-accuracy sensing; and (4) binding of Ca+2 and glucose are thermodynamically coupled, wherein this effect introduces a variance in the glucose concentration of ±~2% at a given signal and temperature in the 0.8-2.0 mM [Ca+2] concentration range.

Next, the selected glucose biosensors are then affinity tuned by mutagenesis to (i) verify that the wild-type interacts between the protein and glucose persist in the GGBP conjugate; (ii) establish which interactions encode the glucose affinity of the GGBP conjugate; and (iii) identify variants that raise or lower the glucose affinity at a desired temperature to provide the desired characteristics for biosensor functionality. Engineered proteins of the present disclosure can be produced by site-specifically introducing a reporter group(s) by total synthesis, ·semi-synthesis, gene fusions, or reaction of a mutant containing a single cysteine with a thiol-reactive reporter group. Introduction of site-specific mutations can be done using methods known to those skilled in the art. Purification of the glucose biosensors may be accomplished using numerous means, including fusion with affinity tags placed at the N or C terminal ends, or both. Such methods are well known in the art and can be readily determined by one skilled in the art.

EXAMPLES

Example 1

Biophysical Analysis and Performance Optimization of *E. coli* Glucose-Galactose Binding Protein for Continuous Glucose Monitoring Executive Summary An engineered, fluorescently labeled version of glucose-galactose binding protein, developed originally at Duke University, has been incorporated successfully into an optrode by Becton-Dickinson Technologies; this sensor performs well in animal and human trials. The aims of this project are to gather biophysical information essential for sensor performance analysis, and to further engineer the protein for the development of next-generation sensors:
(a) To understand the mechanism by which glucose binding is transduced into a fluorescent signal.
(b) To determine the variation in signal response in pathophysiological temperature ranges (35-42° C.) in order to understand potential temperature-dependent systematic errors, which is essential for engineering high-accuracy sensors.
(c) To determine the variation in signal response in pathophysiological calcium concentration ranges (0.8-1.5 mM), which also is a potentially important element in determining sensor accuracy.
(d) To discover variants that enable the construction of second-generation sensors that provide a near-linear response over a wider range of pathophysiological glucose concentrations than is possible with the current generation sensor based on a single protein.

These aims were all achieved. The high-resolution X-ray structure of the fluorescent acrylodan conjugate with bound glucose revealed interactions between the fluorophore and the protein, and changes in the interactions between the protein and bound glucose. These insights could not have been deduced from knowledge of the wild-type structure alone.

Systematic mutagenesis of the glucose-binding site and the interactions unique to the engineered sensor protein uncovered seven mutations that tune the sensor affinity into the hypo- and hyperglycemic regions. Four of these mutations involve alterations to interactions that are present only in the fluorescent conjugate protein; the structural information obtained in this effort was therefore useful for their discovery. These mutants enable the construction of next-generation, composite sensors with extended, high-accuracy detection ranges.

A thermodynamic model was developed that accurately describes the fluorescent response of the sensor as a function of glucose and calcium concentrations and temperature. This analysis clearly reveals that in the absence of temperature corrections, the error in the glucose concentration varies −7.4% to +18.5% over the pathophysiological 35-42° C. temperature range if the sensor were calibrated at 37° C. Determination of the temperature at the sensing tip of the current-generation optrode will eliminate systematic error due to this effect. Furthermore, a preliminary analysis of the tuning mutants suggests that it may be possible to exploit the differences in their thermodynamic properties to provide the necessary temperature corrections in a composite sensor obviating extrinsic thermometry in next-generation, wide range, high accuracy optrodes.

The thermodynamic models also reveal that variation in calcium concentration influences glucose binding. The systematic error in the glucose concentration uncorrected for calcium concentration is <2% in the pathophysiological glucose and calcium concentration ranges. This finding establishes that it is not necessary to include an error correction mechanism for calcium concentration in the current generation optrode. Nevertheless, in next-generation, composite sensor correction mechanisms to eliminate systematic error due to calcium concentration fluctuations could be included.

The study reported here therefore has provided critical information for understanding and improving current-generation sensor performance. Furthermore, it has provided a route for the development of next-generation continuous glucose monitors that incorporate composite sensors to extend coverage in the hypo- and hyperglycemic ranges and function with superlative accuracy.

Summary of the Finding

Project Aims: (1) Determine high-resolution structures by X-ray crystallography of the fluorescently labeled glucose-galactose binding protein (GGBP) in the presence and absence of glucose and galactose; (2) Construct a detailed thermodynamic characterization of glucose and galactose affinities as a function of temperature (Gibbs-Helmholtz surface) and free calcium; (3) Construct variants with affinities in the hyperglycemic glucose concentration range (10-33 mM).

Summary of Achievements

Structure Determination: The structure of the GGBP183C·acrylodan conjugate glucose complex was determined to 1.5 Å resolution, revealing four essential findings: (1) The structure of the GGBP183C·acrylodan closed conformation is indistinguishable from wild-type; (2) The conjugated acrylodan points out of active site, vacating the position that was occupied by tryptophan 183 in the wild-type protein; (3) A buried water molecule replaces the tryptophan 183 indole ring; (4) Acrylodan interacts with protein residues outside the glucose-binding site. These unanticipated interactions can be manipulated by mutagenesis for tuning glucose affinity.

Thermodynamic Characterization: A thermodynamic model was developed that accurately describes the dependence of the fluorescence response of GGBP183C·acrylodan to glucose, galactose, calcium, and temperature. This model revealed several mechanistic features that are relevant to the utilization of GGBP183C·acrylodan in a continuous glucose monitoring optrode: (1) The glucose affinity exhibits significant temperature dependence, as expected for any chemical equilibrium; (2) This temperature dependence varies the glucose concentration relative to that measured at 37° C. at a given signal level by ±3.7% in the diurnal temperature range (36-38° C.) and −7.4% to +18.5% over the pathophysiological range 35-42° C.; (3) Quantitative description of this behavior combined with measurement of the temperature enables high-accuracy sensing; (4) Binding of $Ca^{2+}$ and glucose are thermodynamically coupled. This effect introduces a variance in the glucose concentration of ±~2% at a given signal and temperature in the 0.8-2.0 mM $[Ca^{2+}]$ concentration range.

Tuning of Glucose Affinity: Of the 52 mutants examined, seven mutations were identified that alter the GGBP183C·acrylodan glucose affinity, enabling extension of high-accuracy coverage in the hyperglycemic and hypoglycemic concentration ranges by use of a sensor array. Knowledge of the three-dimensional structure of GGBP183C·acrylodan conjugate was essential for this effort. The seven mutations divide into three classes (glucose $K_d$ values at 37° C. are shown): (1) Interactions with the glucose 6-hydroxyl: N152, $K_d$ ~14 mM; F152, $K_d$ ~17 mM; Q152, $K_d$ ~36 mM; (2) Interactions with acrylodan: Q149, S149, K149 all have $K_d$ ~0.5 mM; (3) Interactions with the buried water molecule: N155, $K_d$~13 mM.

Materials

Two sets of proteins were studied: the original GGBP183C·acrylodan conjugate and its variants (all prepared in this laboratory), and the BD_SM4 variant originally isolated by Becton-Dickinson Technologies, (BDT) and provided to us by BDT as purified, fluorescently labeled protein.

Fluorescently labeled protein conjugates prepared in this laboratory were produced by over-expression of a C-terminal hexahistidine-tagged fusion protein, and purified by immobilized metal affinity chromatography and reacted with acrylodan, as described (DeLorimier et al. Prof. Sci. 2002, 11, 2655-2675). Conjugated proteins were stored at 4° C. and used for experiments within one month. Point mutants used in this study were constructed by oligonucleotide-directed mutagenesis, and verified by DNA sequencing.

Structure of GGBP183C·Acrylodan Bound to Glucose

Structure Determination: Crystallization conditions for the GGBP183C·acrylodan conjugate were determined using 0.5 μL sitting drops (0.1 mM protein, 125 mM glucose, 1 mM $CaCl_2$, 10 mM KCl, 10 mM MOPS, pH 7.4) in five 96-well sparse-matrix screens stored at 4° C. and 17° C., using a Mosquito liquid-handling robot. The most promising hits were refined in focused screens set up by hand, exploring PEG lengths and concentrations, and pH; a 96-well additive screen was also explored with automation, but yielded no improvements.

Diffraction-quality crystals were grown in 5 μL sitting drops at 4° C. two weeks (26% PEG 4,000, pH 7.75). A similar screen using BD_SM4 did not yield any crystals. We postulate that the additional purification and immobilization tags present in this protein inhibited crystallization. We were also unable to obtain crystals of GGBP183C·acrylodan in the absence of glucose.

After transfer to a cryoprotectant solution containing ~2.5 M glucose, crystals were flash-frozen in liquid nitrogen. Diffraction data was collected at 100K at the Advanced Photon Source, Beamline 22-BM (Argonne National Laboratory). The structure was solved to 1.5Å resolution by molecular replacement using 2GBP as the search model. Structure refinement is currently being finished in preparation for publication.

Figure 2:
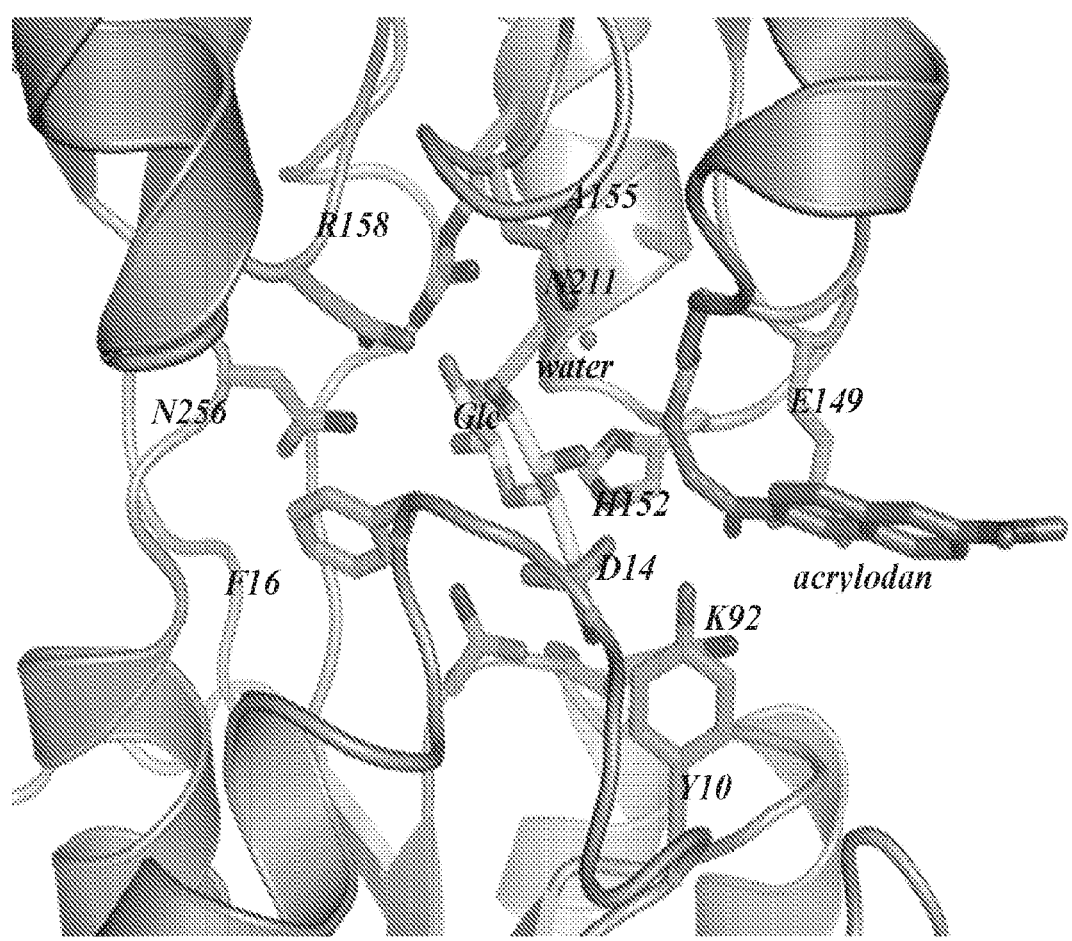
FIG. 2 is a drawing showing the interaction between the protein and bound glucose in the 183C-acrylodan conjugate.

Analysis: The overall structure of the GGBP183C·acrylodan glucose complex is almost indistinguishable from the wild-type closed form conformation (FIG. 1). Acrylodan is attached covalently to the W183C mutation, which is located adjacent to the bound glucose in the interior of the closed conformation. The conjugated acrylodan ring system has vacated the position occupied by the tryptophan indole ring in the wild-type protein, and has swung out of the binding pocket, pointing into the solvent. The vacated ring position is replaced by a water molecule buried adjacent to the bound glucose (FIG. 2). This water is contacted by alanine 155, which in the wild-type protein is located adjacent to the W183 indole ring. The protein backbone barely adjusts to accommodate the acrylodan position. However, glutamate 149 and lysine 92 move, opening an aperture to the surface through which the acrylodan fits. This motion breaks a wild-type, inter-domain salt bridge between E149 and K92, and places the carboxylate of E149 in close proximity to the acrylodan carbonyl, which may represent an unfavorable contact. Other than the replacement W183C indole ring with water, the interactions between the protein and the bound glucose have not changed.

These findings establish that the effects of introducing the acrylodan conjugate are remarkably localized. The ~10,000-fold decrease in the affinity of the GGBP183C·acrylodan for glucose compared to the wild-type protein is therefore a consequence of the loss of the interaction with the W183 indole ring, the loss of the inter-domain salt bridge, unfavorable interactions between the surface residues contacting the acrylodan, or a combination of these effects. These structural hypotheses were tested by mutagenesis (see below).

Thermodynamic Characterization

A detailed thermodynamic model of the sensor response was developed to (i) provide a quantitative, accurate description of the fluorescence landscape (response) as a function of glucose concentration, calcium concentration, and temperature; and (ii) provide an accurate description of any potential systematic errors in the glucose-dependent signal arising from variations in temperature or calcium concentration in pathophysiological ranges.

Fluorescent Landscape Data Collection

Figure 3:
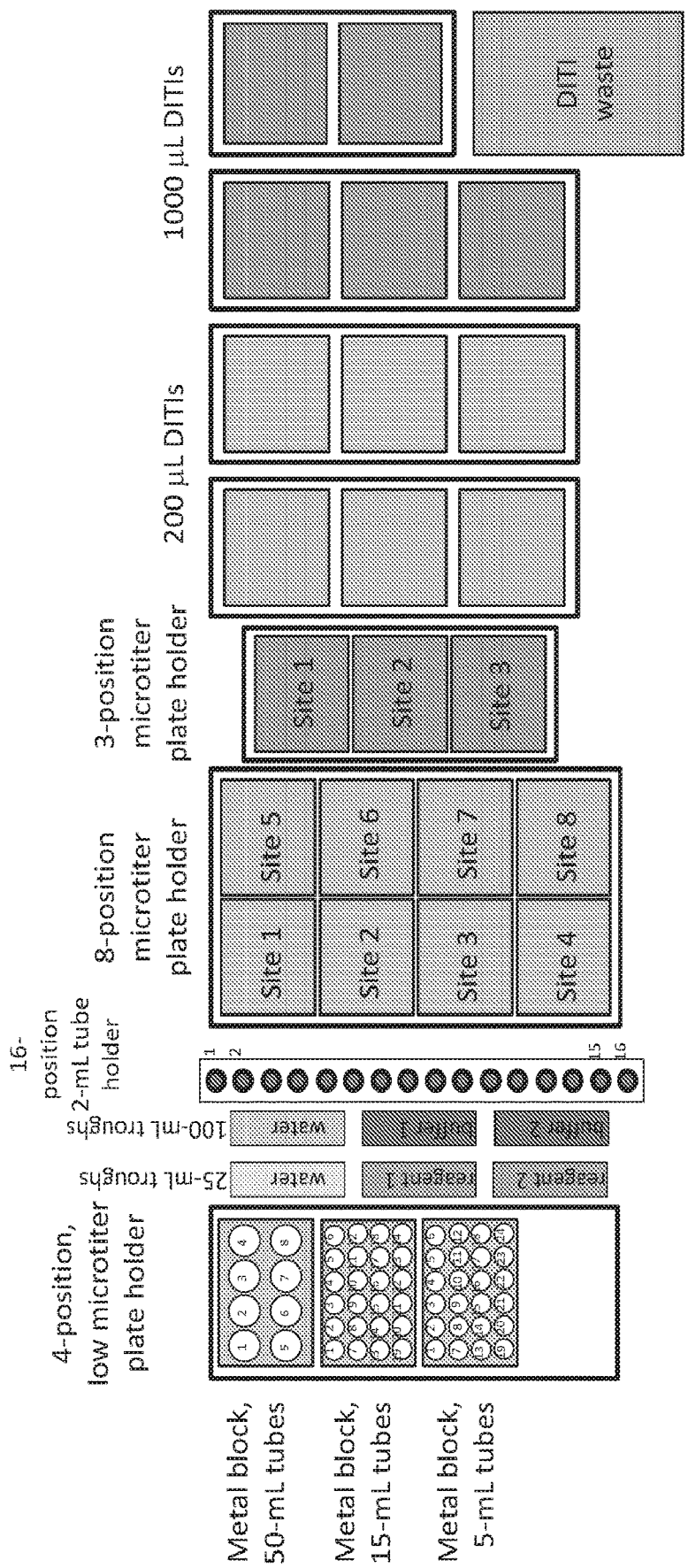
FIG. 3 is a layout of a Tecan Genesis liquid-handling robot for setting up complex high-precision titration series in accordance with one embodiment of the present disclosure.
Figure 4:
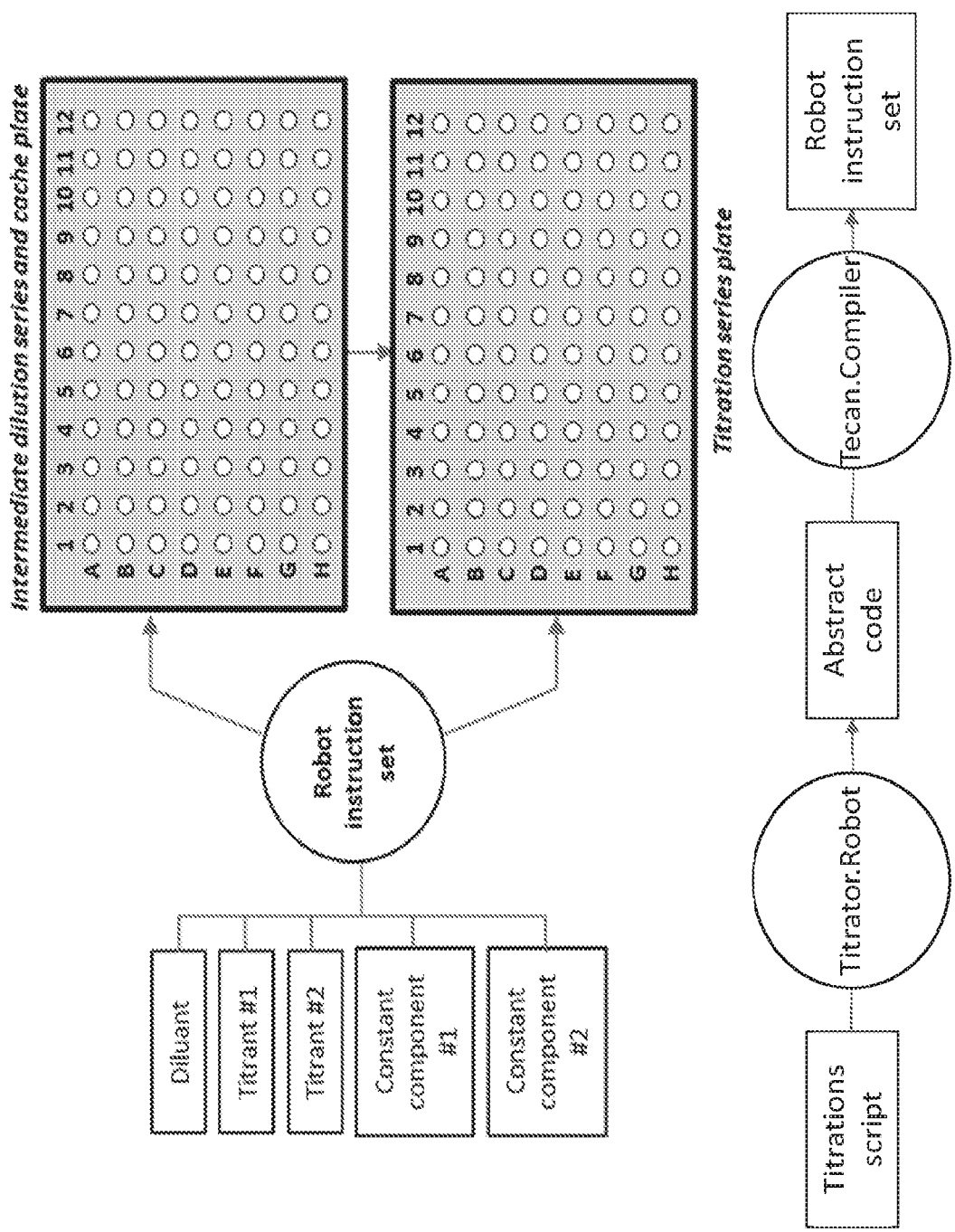
FIG. 4 is a schematic of a liquid-handling software environment according to one embodiment of the present disclosure. Multi-component titrations involve the addition of several constant components, and logarithmic titration series of one or multiple titrants. The titrations are set up in scripts or graphical user interfaces, and translated into machine instructions in a two-stage manner.
Figure 5A:
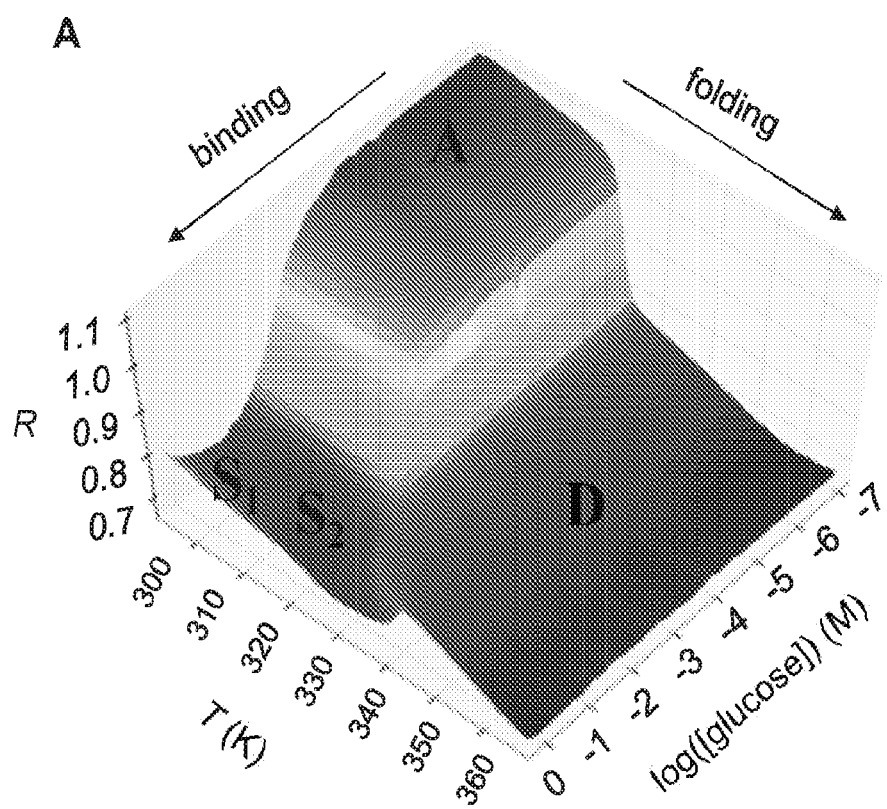
FIG. 5 are graphs showing different landscapes of 183C-acrylodan [(A)-(C)] and BD_SM4-acrylodan [(D)-(F)] fluorescence signals (R, ratio of emission intensities at 440 nm and 510 nm) as a function of glucose concentration and temperature (the data comprises 3840 observations: 48 glucose concentrations, 80 temperatures). The changes in fluorescence arise as the system exchanges between three major states: A, folded apoprotein; S, folded saturated glucose complex; D, denatured apo-protein. The denatured state undergoes a further temperature-dependent two-state conformational change, splitting into sub-states D1 and D2. In 183C-Acrylodan the saturated glucose complex undergoes a temperature-dependent conformation change, splitting into S1 and S2 sub-states. Dotted lines indicate approximate mid-points of unfolding, ligand binding, and conformational changes.
Figure 5B:
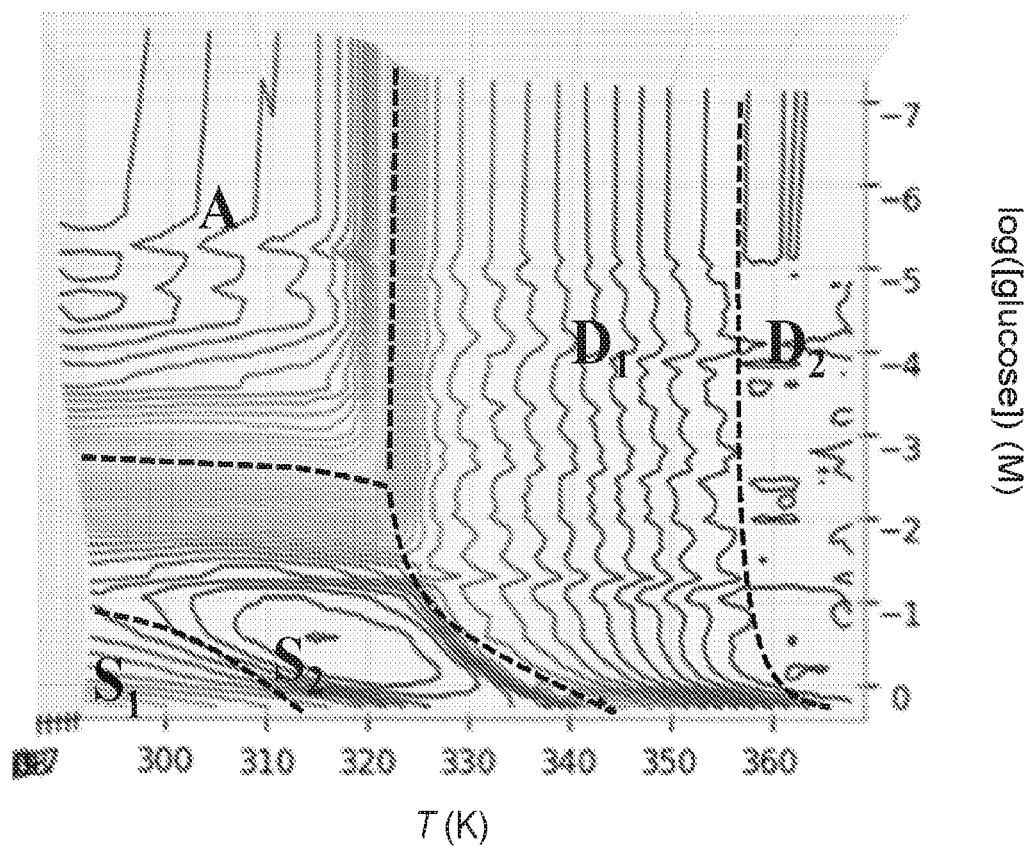
Figure 5C:
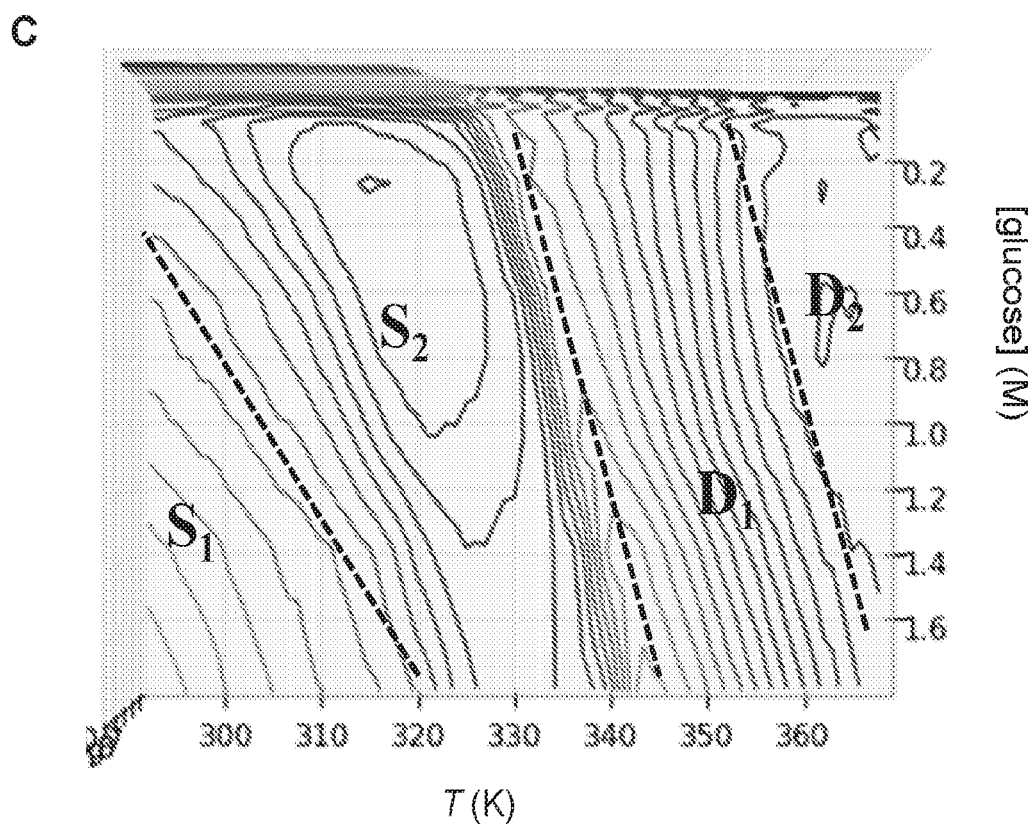
Figure 5D:
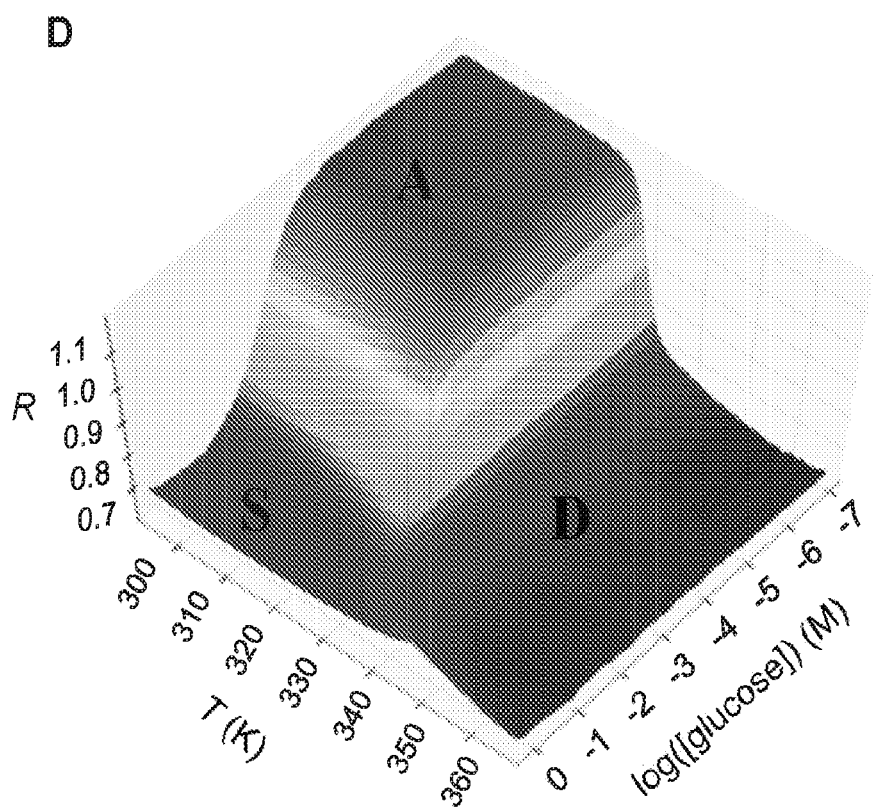
Figure 5E:
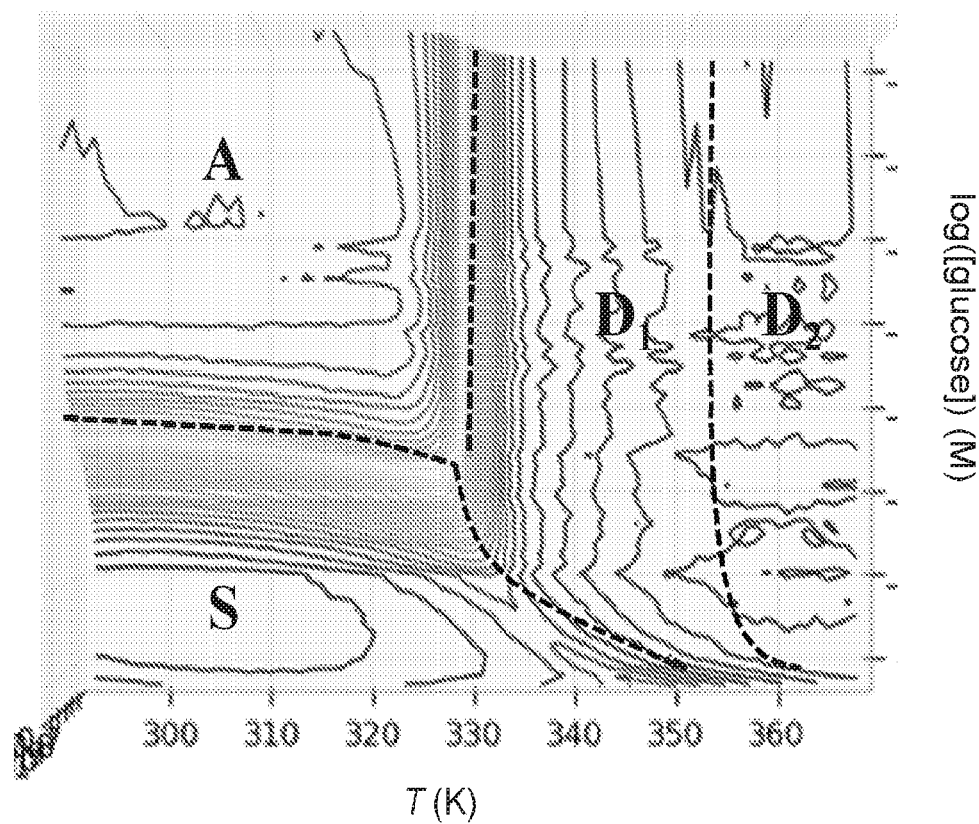
Figure 5F:
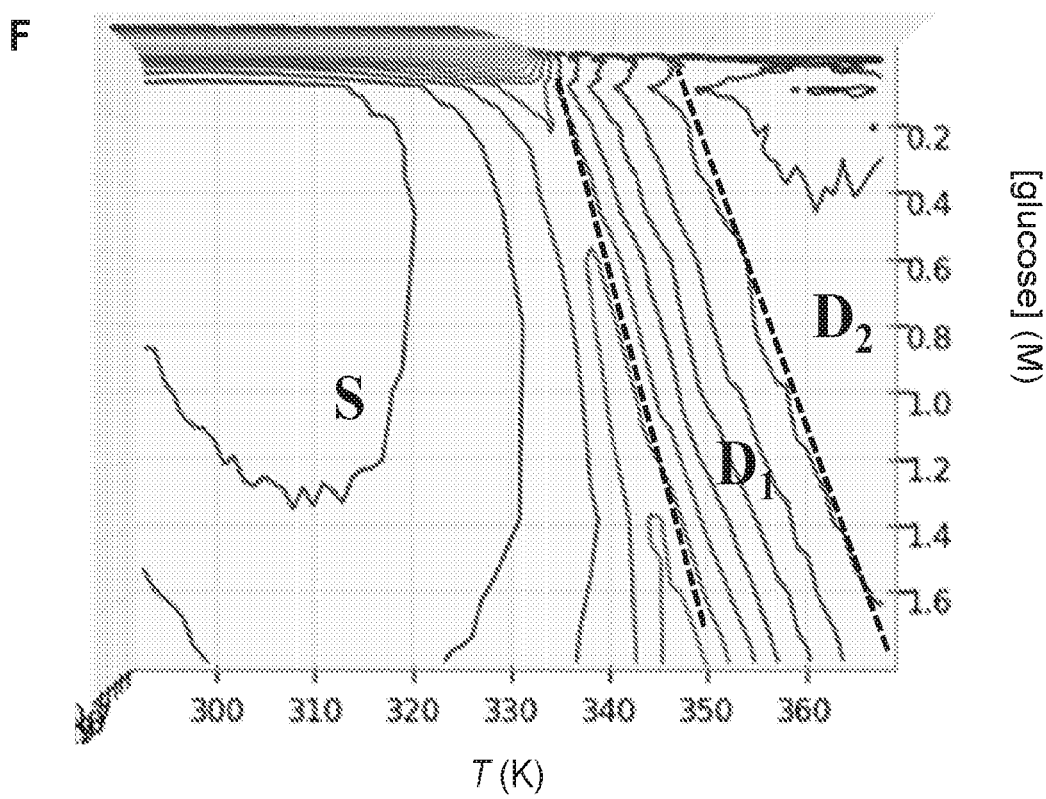

As a first step, we developed automated liquid-handling methods to construct precise, titration series that are finely sampled in a geometric (logarithmic) progression. This required designing the appropriate configuration of a programmable liquid-handling robot (FIG. 3), and writing a software environment that translates an abstract, multi-component titration series into machine instructions to operate the robot (FIG. 4).

The titration series were mixed with GGBP183C·acrylodan or BD_SM4·acrylodan conjugates in 384-well microtiter plates. The temperature dependence of the titrations was measured in a real-time PCR machine (Roche LightCycler 480) by determining the ratio of fluorescence emission intensities at 488, 510, and 580 nm (excitation at 440 nm) as a function of temperature (290-370K). Temperatures were advanced in 1K steps. At each temperature data was collected for at 1-second intervals for 60 seconds at which point the signal had relaxed to a steady value associated with the new temperature. Collection times were adjusted to minimize photobleaching (which was not detectable under these experimental conditions). Data reduction software was developed to convert these observations into time-independent datasets that record fluorescence as a function of temperature for each well and associate wells with their concentration of titrant and additive. Management tools were developed to maintain a database of titrations and their analyses.

Three-dimensional landscapes of fluorescence recorded as a function of glucose concentration and temperature were collected at eight different calcium concentrations. In addition, we collected the fluorescent landscape in a calcium titration determined in the absence of glucose.

Thermodynamic Models of the Fluorescent Landscapes

FIG. 5 shows the dependence of the fluorescent signal on glucose concentration and temperature at 1 mM $Ca^{2+}$ for the GGBP183C·acrylodan and BD _SM4·Acrylodan conjugates. Considerable effort was expended in developing the software necessary for quantitative modeling of the fluorescence response.

Extensive analysis of a variety of quantitative model revealed that the changes in fluorescence arise from temperature- and ligand-dependent changes between various states of the system, each of which is associated with a fluorescence base plane. The total fluorescence signal (i.e., the landscape) as a function of temperature T and ligand concentration L, s(T,L), is then given by $$s(T, L) = \sum_i \beta(T, L)_i f(T, L)_i \qquad 1$$

where $\beta_i$, is the fluorescence base plane associated with the fraction of the ith state fi. Each base plane is defined by its linear temperature dependence on temperature and ligand concentration:

$$\beta_i = S_{0,i} + \left(\frac{\partial S}{\partial T}\right)_i + \sum_j \left(\frac{\partial S}{\partial T}\right)_i \qquad 2$$

where $S_{0,i}$ is the signal at 0 K in the absence of ligand, $$\left(\frac{\partial S}{\partial T}\right)_i \text{ and } \left(\frac{\partial S}{\partial L_j}\right)_i$$

the partial derivatives with respect to temperature and the $j^{th}$ ligand species respectively.

Figure 6:
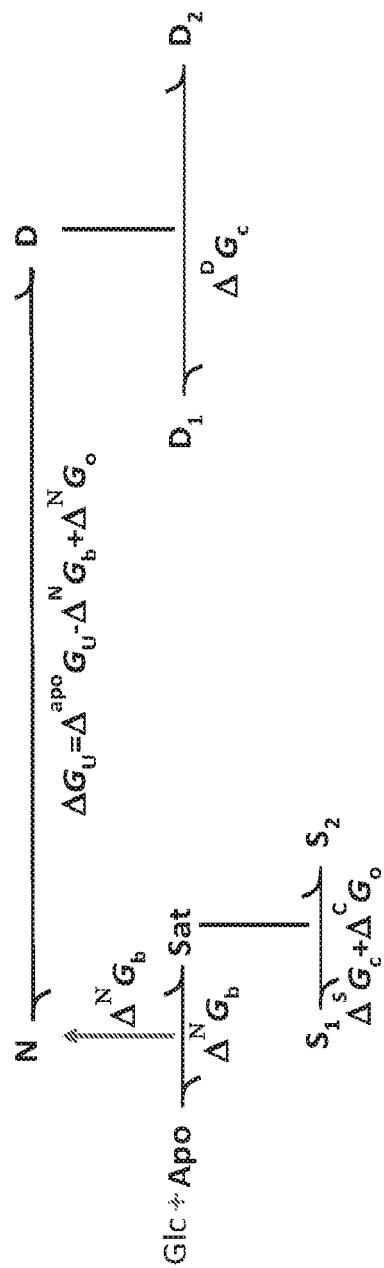
FIG. 6 is a schematic representation of the binding, confirmation change, and unfolding equilibria in GGBP and their sensitivity to glucose binding at constant calcium. The leaves of the tree correspond to experimentally observable states of the protein; the nodes are the equilibria between these individual states, or ensembles composed of these states. All equilibria are temperature sensitive. Binding equilibria put energy into the system, which propagates upward into the various ensembles (red arrows). Symbols are defined in the specification.

The two landscapes shown in FIG. 5 can be described in terms of three major states: the folded apo protein (A), the folded saturated glucose complex (S), and the denatured state (D). The signal decreases both in response to glucose binding, and thermal denaturation. In both proteins, the denatured state is split into two sub-states, $D_1$ and $D_2$, by a conformational transition that occurs at high temperatures (~360 K). In GGBP183C·acrylodan the glucose complex undergoes a conformational change at ~300 K, splitting into sub-states S1 and S2. The signal "ridge" that separates S and D at high glucose concentrations and elevated temperatures (320-340 K) is the consequence of two effects. First, as the temperature increases, the affinity for glucose is lowered, and apo-protein forms, which has a higher signal than the complex: the ridge rises. Second, as the temperature increases further, the protein thermally denatures, and the baseplane of the denatured state predominates: the ridge drops. It is also readily apparent that the stability of the protein increases significantly in this region: the mid-point of the ridge moves to higher temperatures with increased glucose concentration. This is the consequence of two other effects. First, ligand binding stabilizes the folded state. Second, glucose is a stabilizing osmolyte. Such reagents alter protein stability by changing the water activity, typically at high concentrations. Their effect on free energy is linear with osmolyte concentration. The glucose osmolyte effect dominates in this region (see the linear dependence on the ridge mid-point in FIG. 5C and FIG. 5F). These relationships are depicted in FIG. 6.

(1) Thermal unfolding converts the folded state(s), N, into the unfolded state(s), D.
The free energy of unfolding $\Delta G_U(T,L)$ is dependent on
  a. The temperature dependence of thermal stability in the absence of any ligand, $\Delta^{apo}G_U(T)$.
  b. Free energy of binding of glucose to the folded state, $\Delta G_{b,glc}(T,L)$.
  c. Free energy of binding $Ca^{2+}$ to both the folded, $\Delta^N G_{b,Ca}(T,L)$, and denatured states, $\Delta^D G_{b,Ca}(T,L)$.
  d. The free energy of the osmolyte effect of glucose on the free energy of the folded apo-protein $\Delta^N G_O$.

(2) In both proteins, the unfolded state undergoes a conformational change, splitting it into two sub-states, $D_1$ and $D_2$. This free energy, $\Delta^D G_C(T)$ is dependent on temperature.

(3) In both proteins glucose binds to the folded state, converting between the apo state, A, and saturated ligand complex, S. This free energy, $\Delta G_{b,glc}(T,L)$, is dependent on glucose concentration and temperature.

(4) In GGBP183C·acrylodan the saturated glucose complex undergoes a conformational transition that further splits it into two states, $S_1$ and $S_2$. The free energy of this process $\Delta^S Gc(T)$, is dependent on temperature and the osmolyte effect of glucose on conformational transitions $\Delta^C G_O$.

This system is described by the following set of nested equations.

$$\Delta G_U(T, L) = \qquad\qquad 3$$
$$\Delta^{apo}G_U(T) - \Delta G_{b,glc}(T, L) + \Delta^D G_{b,Ca}(T, L) - \Delta^N G_{b,Ca}(T, L) + \Delta^N G_O$$

$$\Delta^{apo}G_U(T) = \Delta H'_U + \Delta C_{p,u}(T - T_m) - T\left(\frac{\Delta H'_U}{T_m} + \Delta C_{p,u}\ln\frac{T}{T_m}\right) \qquad 4$$

is the Gibbs-Helmholtz description of the temperature dependence of unfolding, where $T_m$ is the mid-point of the thermal transition where $\Delta^{apo}G_U(T)=0$, $\Delta H_U$, the enthalpy at the $T_m$, and $\Delta C_{p,u}$ the heat capacity.

$$\Delta G_{b,X}(T,L) = -RT\ln Q_{b,X}(T,L) \qquad 5$$

is the binding energy of the binding polynomial for ligand X (glucose or $Ca^{2+}$).

$$Q_{b,X}(T, L) = 1 + \frac{L}{K_{L,X}(T)} \qquad 6$$

is the binding polynomial for a single ligand-binding site, where $K_{d,X}(T)$ is the temperature-dependent dissociation constant for ligand X.

$$K_{d,X} = \left(e^{-\Delta G'_{b,X}/RT} - 1\right)^{-1} \qquad 7$$

$$\Delta G'_{b,X} = \Delta H'_{b,X} + \Delta C_{p,b,X}(T - T') - T\left(\frac{\Delta H'_{b,X}}{T'} + \Delta C_{p,b,X}\ln\frac{T}{T'}\right) \qquad 8$$

is the Gibbs-Helmholtz description of the free energy of binding ligand X under standard state conditions ([X]=1 M), where T* is the temperature at which $\Delta G_{b,X}=0$, $\Delta H_{b,X}$ the standard binding enthalpy at T*, and $\Delta C_{p,b,X}$ the ligand-binding reaction heat capacity.

$$\Delta^N G_O = m_N[\text{glucose}]$$

is the linear free energy relationship that arises from the osmolyte effect due to glucose.

$$\Delta G_C(T) = \Delta H'_C + \Delta C_{p,c}(T - T_c) - T\left(\frac{\Delta H'_C}{T_C} + \Delta C_{p,c}\ln\frac{T}{T_C}\right) + \Delta^C G_O \qquad (9)$$

is the Gibbs-Helmholtz description of the temperature dependence of a two-state conformational change (in the denatured state of the saturated glucose complex).

$$\Delta^C G_O = m_C[\text{glucose}]$$

Landscape equation 1 expands as $$S(T,L) = f_N(1 - \bar{y}_{glc})\beta_A + f_N \bar{y}_{glc}\beta_S + (1 - f_N)f_{D1}\beta_{D1} + (1 - f_N)(1 - f_{D1})\beta_{D2} \qquad 10$$

For BD_SM4-acrylodan, and $$S(T,L) = f_N(1 - \bar{y}_{glc})\beta_A + f_N \bar{y}_{glc} f_{S1}\beta_{S1} + f_N \bar{y}_{glc}(1 - f_{S1})\beta_{S1} + (1 - f_N)f_{D1}\beta_{D1} + (1 - f_N)(1 - f_{D1})\beta_{D2} \qquad 11$$

For GBP183C-Acrylodan. To get the fractions of each state:

$$f_N = \frac{1}{1 + K_U(T, L)} \text{ and } K_U\left(T, L = e\frac{\Delta G_U(T, L)}{RT}\right) \qquad 12$$

$$f_{D1} = \frac{1}{1 + {}^D K_C(T)} \text{ and } {}^D K_C(T) = e\frac{\Delta^D G_C(T)}{RT} \qquad 13$$

$$f_{S1} = \frac{1}{1 + {}^S K_C(T)} \text{ and } {}^S K_C(T) = e\frac{\Delta^S G_C(T)}{RT} \qquad 14$$

$$\bar{y}_{glc} = \frac{1}{1 + \frac{[glc]}{K_{d,glc}(T)}} \qquad 15$$

Fits of these equation systems to experimental observations such as shown in FIG. 5 require good initial estimates of the parameters. These can then be refined using multi-dimensional conjugate gradient methods. To obtain local fits for protein thermostability in the absence of ligand we solve $$s(T) = f_N \beta_A + (1 - f_N)\beta_D \qquad 16$$

using 12, with the van't Hoff approximation:

$$K_U(T) = e\frac{\Delta H'_U\left(\frac{1}{T} - \frac{1}{T_m}\right)}{R} \qquad 17$$

Figure 7A:
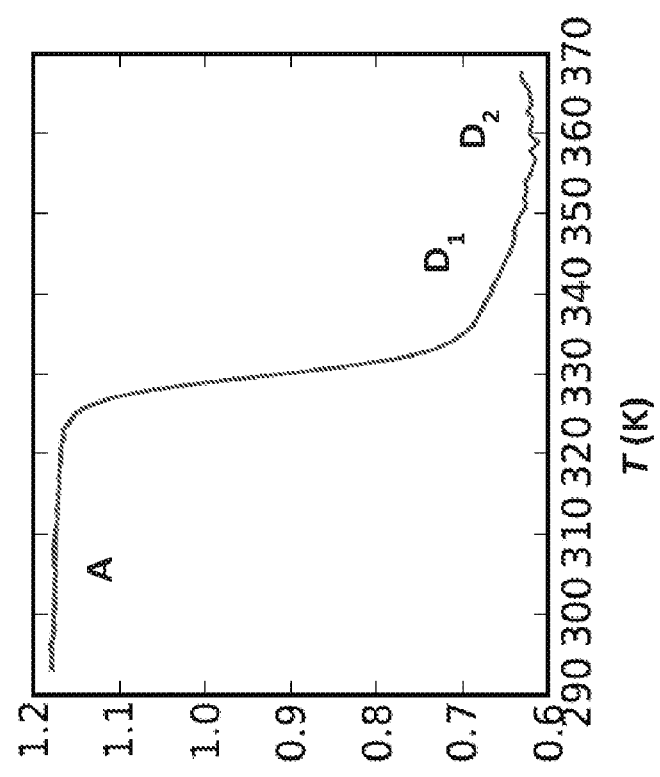
FIG. 7 are graphs showing the estimation of apo-protein stability. The experimental dependence of the fluorescence signal, R, is fit to a two-state model over the temperature range where the thermal denaturation between A and D1 dominates. (A) GBP183C Acrylodan (RMSD; apoTm, 322.2 K; Δapo Hu, 197.3 kcal/mol). (B) BD_SM4 Acrylodan (apoTm, 329.7 K; ΔapoHu, 156.6 kcal/mol).
Figure 7B:
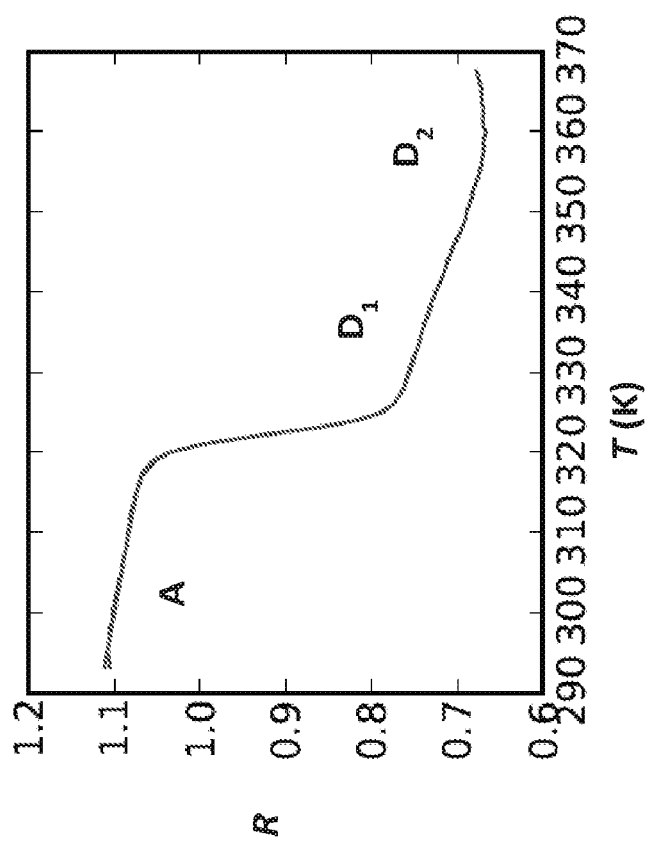

This gives excellent fits (FIG. 7).

Figure 8:
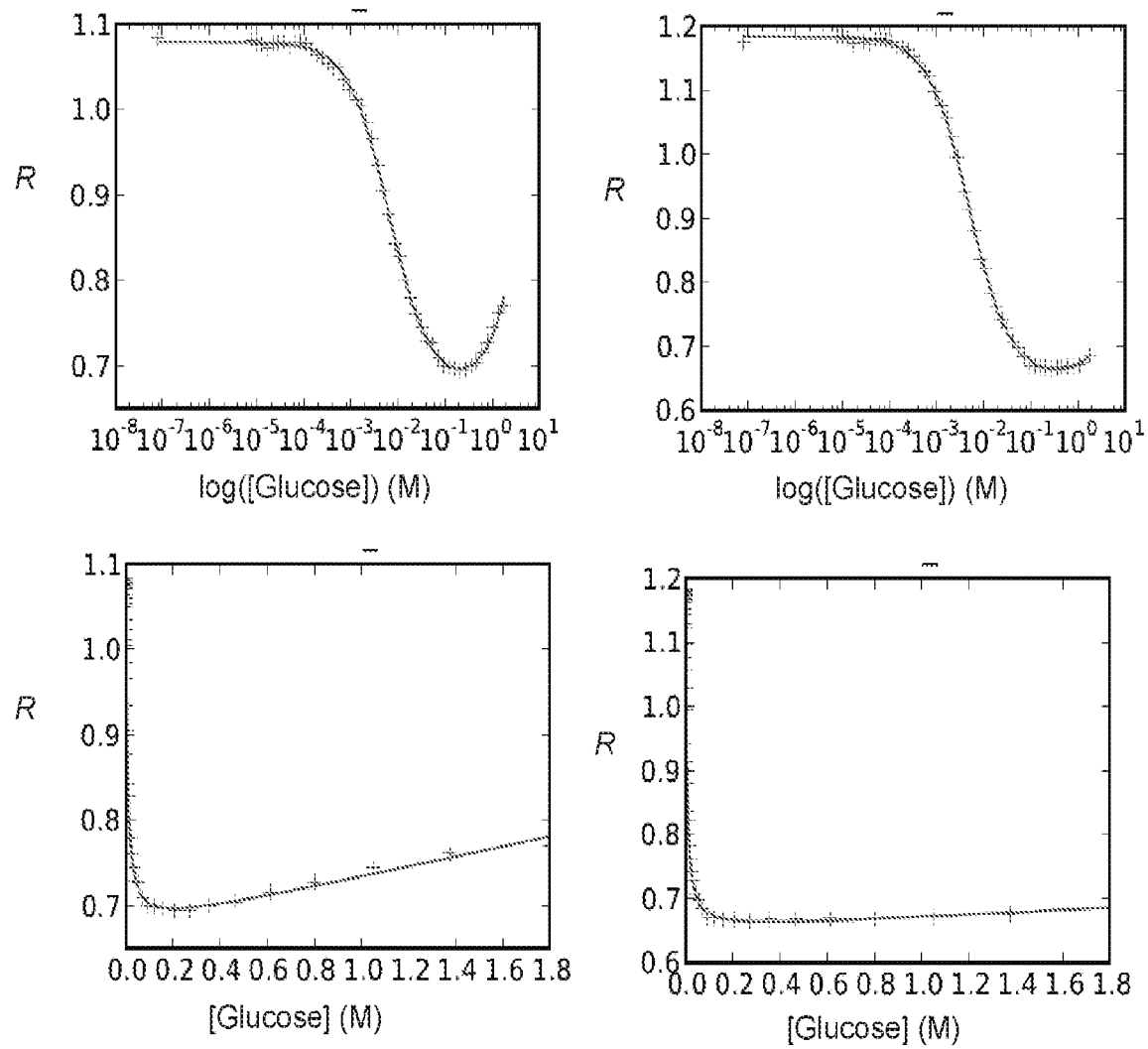
FIG. 8 are graphs showing glucose binding isotherm at 37° C. (310K). Left column: GBP183C·Acrylodan; right column: BD_SM4·Acrylodan. Green line, fit of equation 18 to the data: Kd values of 6.58±0.03 mM and 4.89±0.02 mM for GBP183C·Acrylodan and BD_SM4·Acrylodan respectively. The RMSD values of 0.00418 and 0.0044 correspond to estimated errors of 0.48% (GBP183C·Acrylodan) and 0.48% (BD_SM4·Acrylodan) at [glucose]=Kd·Top: the signal with respect to the logarithm of glucose concentration shows even sampling of the binding isotherm (the zero ligand point is placed at 10-7 M for visualization). Bottom: the linear dependence of the signal on glucose concentration emphasizes the effect of high glucose concentrations on the fluorescence baseline.
Figure 9:
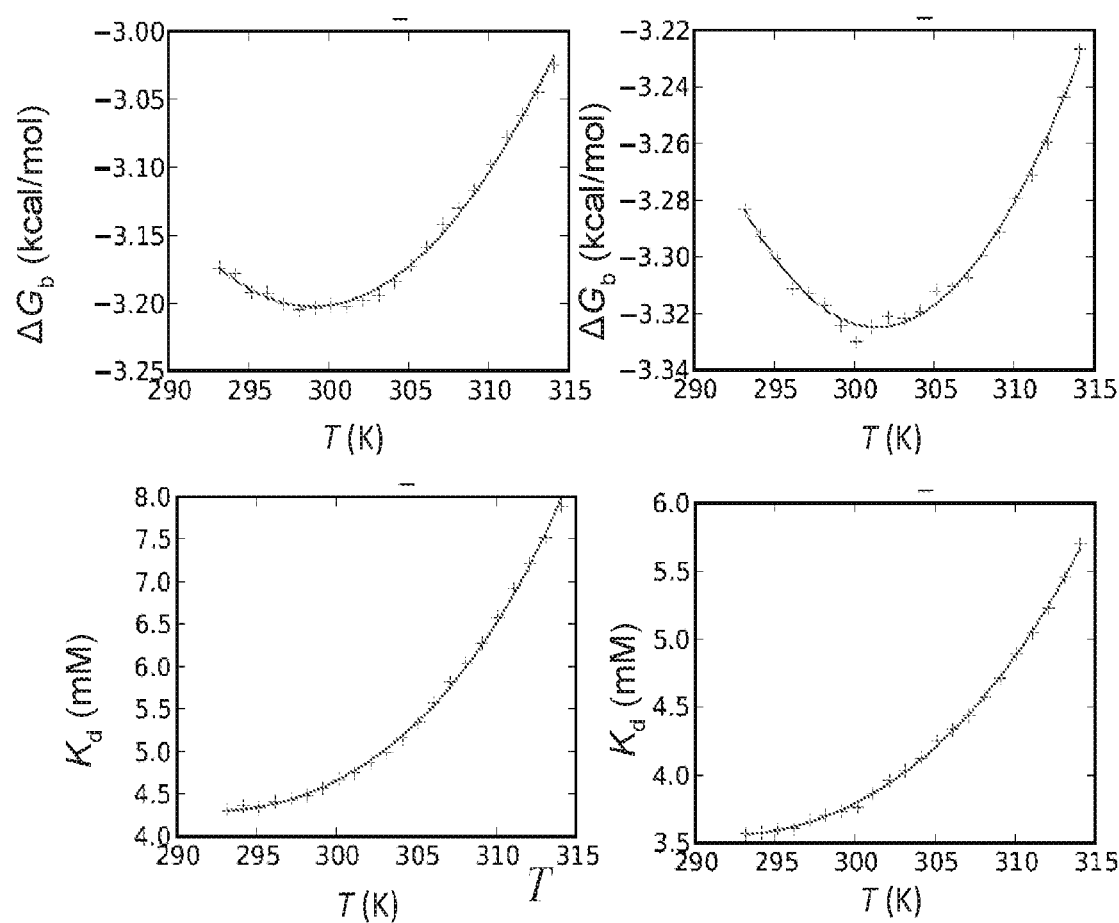
FIG. 9 are graphs showing the temperature dependence of glucose binding. Left column, GBP183C·Acrylodan; right column, BD_SM4·Acrylodan. Top row: temperature dependence of glucose binding free energy (green, fit to Gibbs-Helmholtz equation 8). Bottom row: temperature dependence of the glucose dissociation constant (green, transform of the fit Gibbs-Helmholtz curve).

The response of acrylodan to glucose binding was separated from the effects of thermal denaturation by extracting binding isotherms within the temperature range where the apo-protein remains >99% folded (T<320 K; FIG. 7). Within this temperature range, binding isotherms were constructed by extracting fluorescence values across different wells, each containing different glucose concentrations, at a given temperature, and fit individually with high accuracy to isotherms (FIG. 8):

$$S_T(L) = \bar{y}_T^S \beta_T + (1 - \bar{y}_T)^A \beta_T \qquad 18$$

using linear baselines which vary individually in accordance with the tilt of the S, $S_1$, and $S_2$ baseplanes that correspond the saturated glucose complex. The individually fit $K_d(T)$ values were converted into $\Delta G_b(T)$ and fit to the Gibbs-Helmholtz equation 9 (FIG. 9).

Figure 10A:
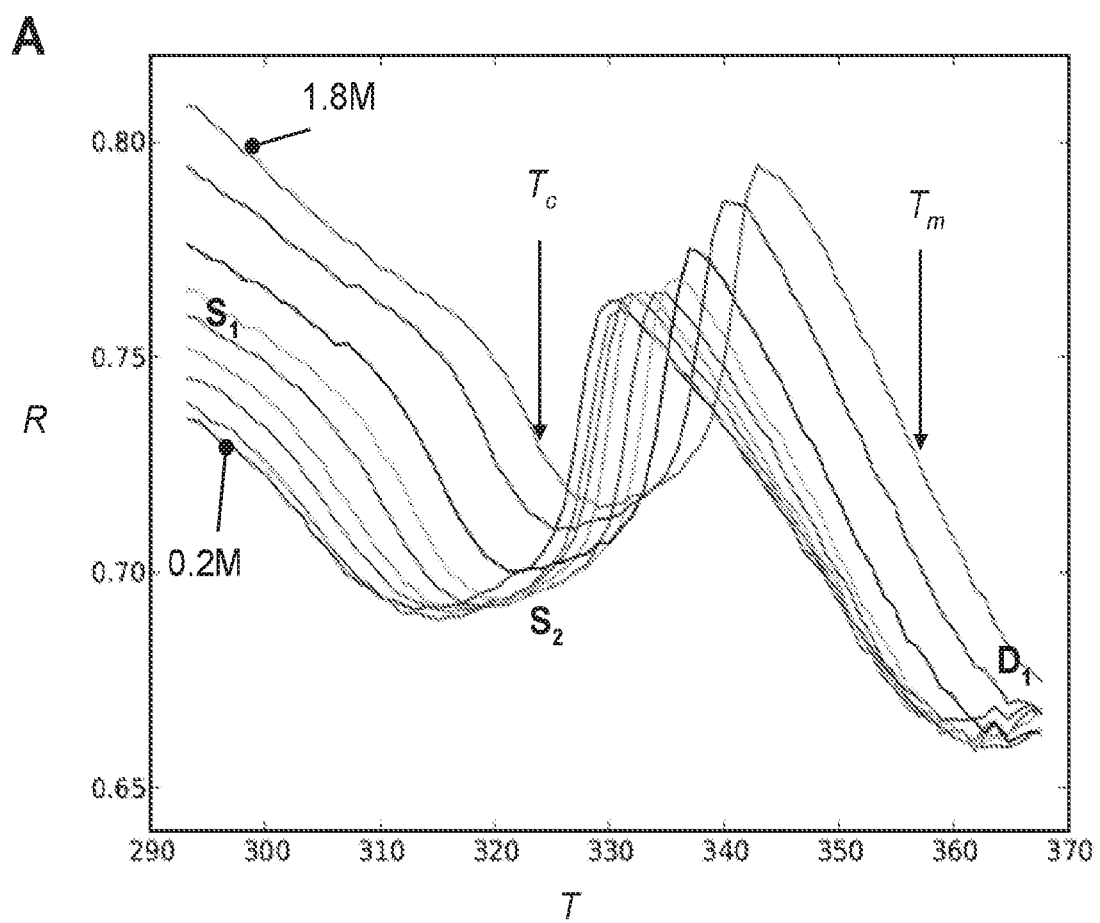
FIG. 10 are graphs showing the conformational changes in the folded protein-glucose complex of GBP183C·acrylodan. (A) Thermal melts are shown for the subset of individual wells containing 0.2-1.8 M glucose, corresponding to saturated protein-ligand complexes. The saturated complex undergoes a thermal conformational change, separating its baseplane into two components, S1 and S2. (B) The glucose osmolyte effect on this conformation. Tc values calculated by individual fits (+) fit to a linear dependence on glucose concentrations (blue line). (C) ΔHc values calculated by individual fits (+) fit to a linear dependence on glucose concentrations (blue line).
Figure 10B:
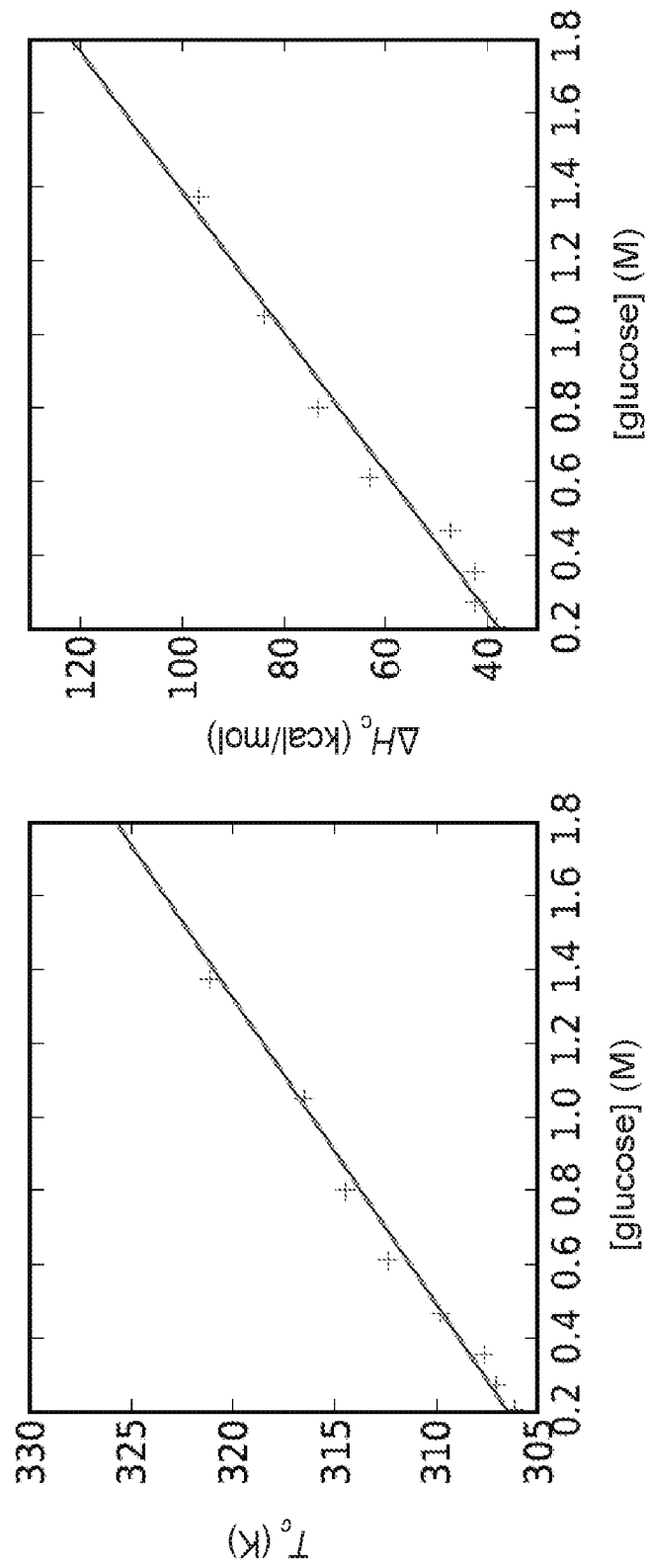
Figure 11A:
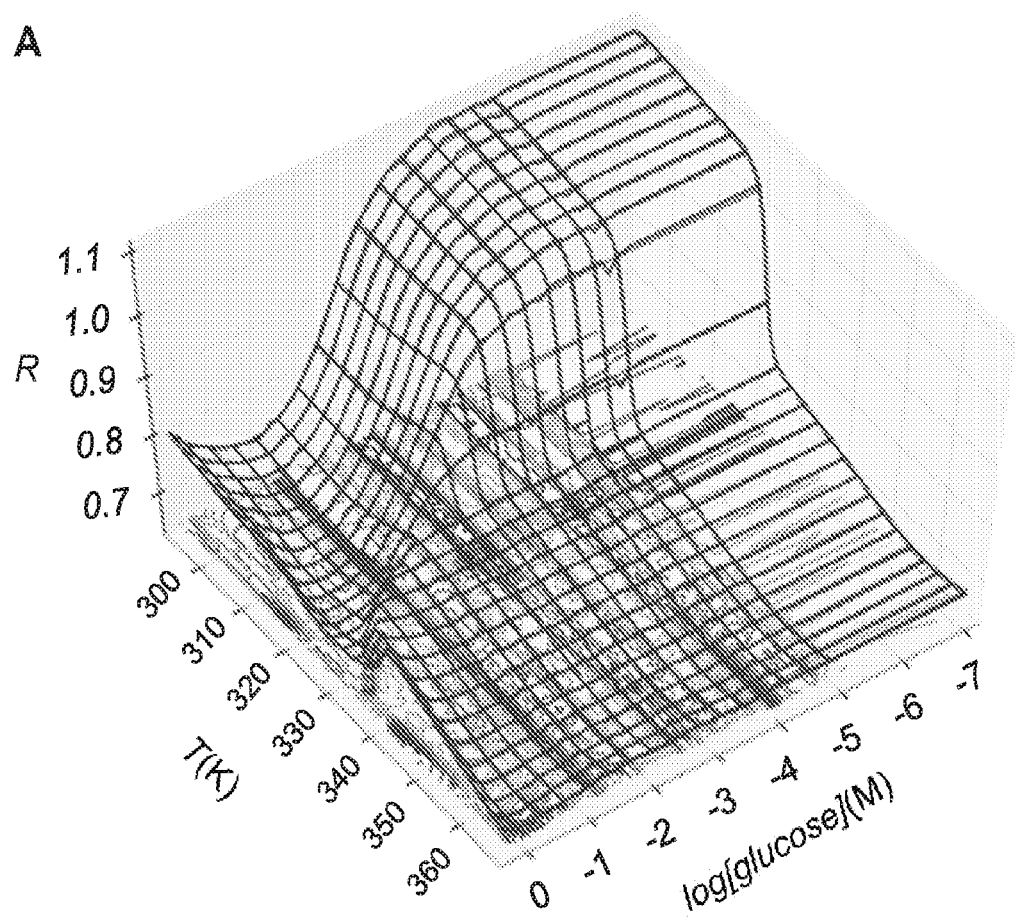
FIG. 11 are graphs showing global fits of the thermodynamic model to the fluorescence ratio (R) dependence on glucose and temperature at 1 mM $CaCl_2$ for GBP183C·Acrylodan (A) and BD _SM4·Acrylodan (C): blue, observations; red, model; contours, residuals. Bootstrap analysis (B and D) shows the average model (orange), and range of deviation in the values (contours).
Figure 11B:
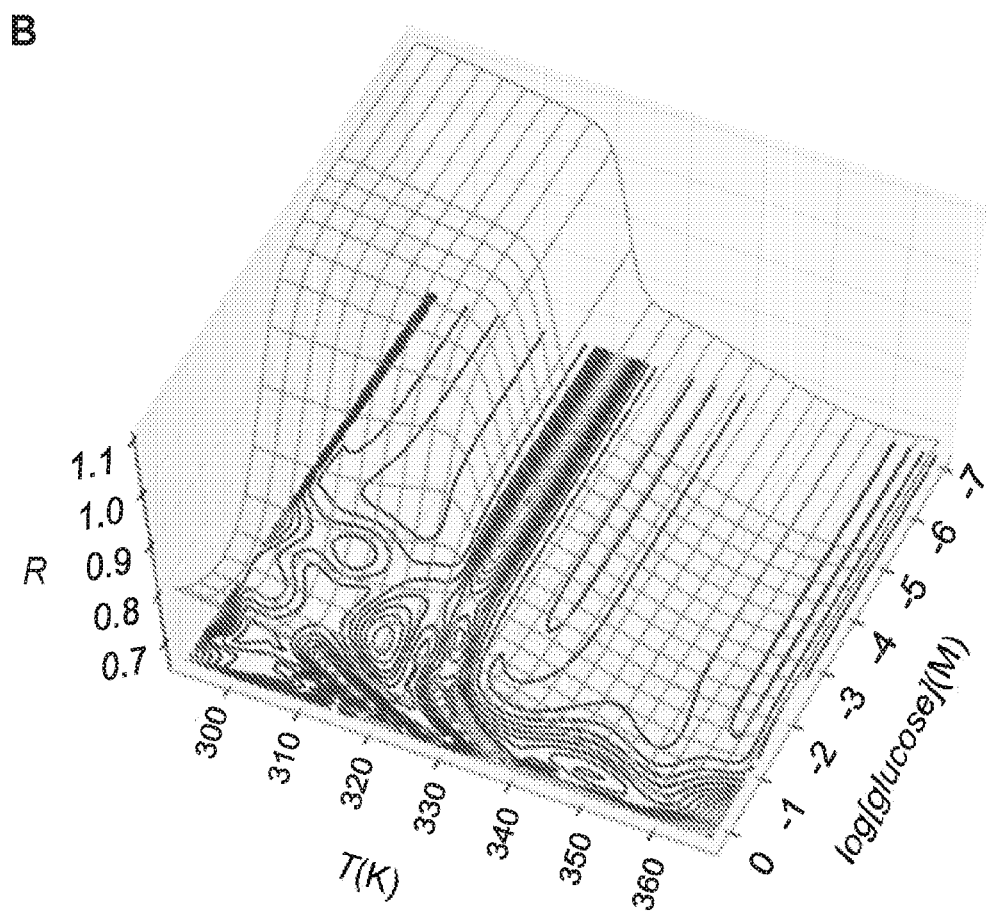
Figure 11C:
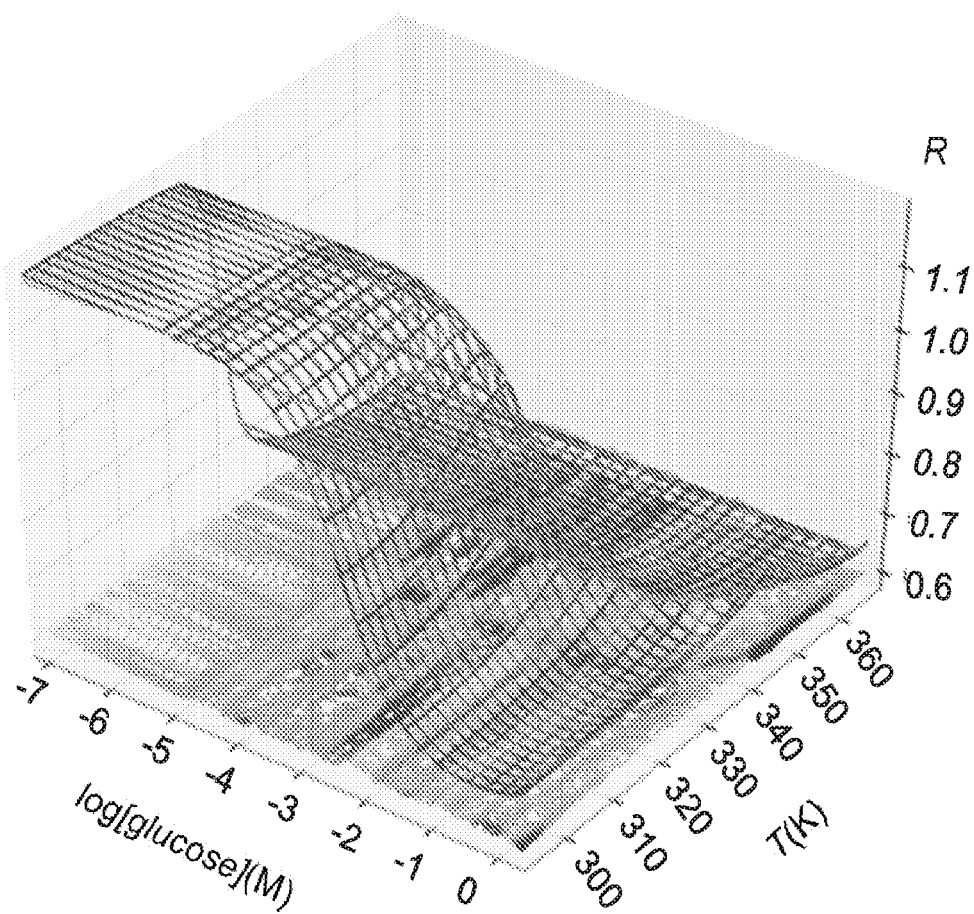
Figure 11D:
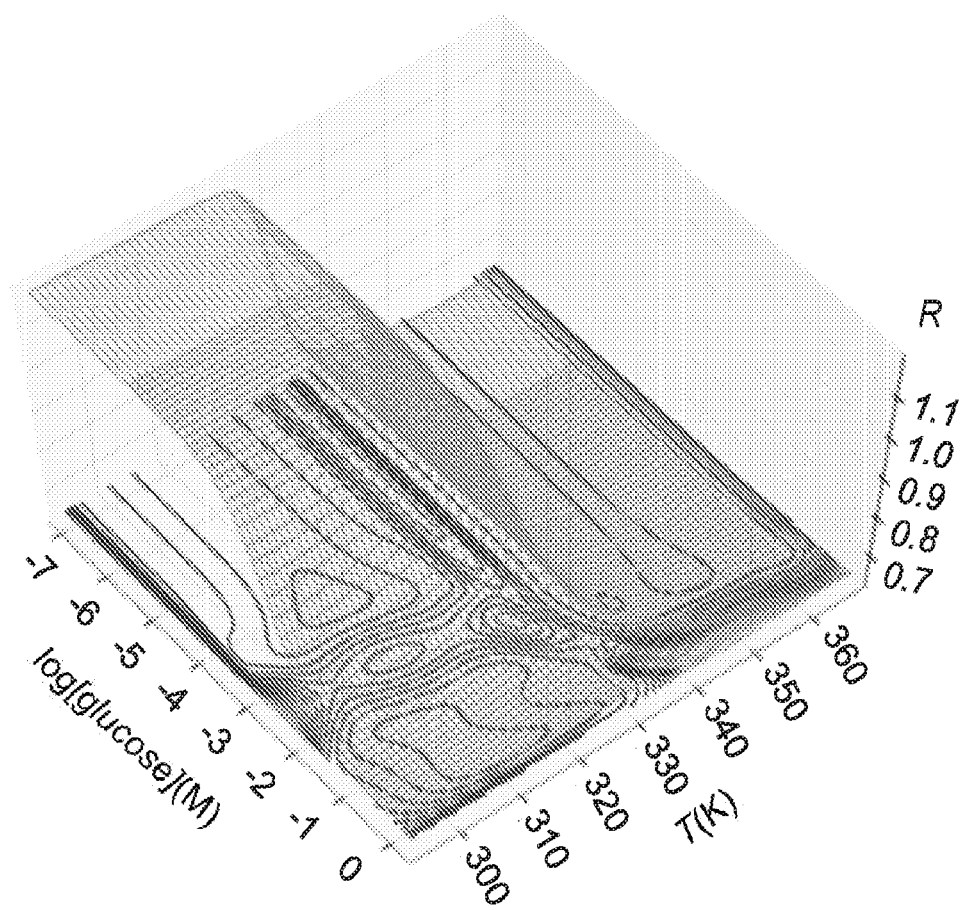

The thermally-driven conformational change in the saturated glucose complex of GBP183C·Acrylodan (FIG. 10) was fit to a two-state model with linear baselines using equations 16 and 17 within temperature ranges where the fluorescence signal is expected to be dominated by this effect (FIG. 10A). These thermal transitions were fit individually for wells containing glucose concentrations in excess of 0.2 M. The resulting values for transition mid-point temperatures, $T_c$, and conformational enthalpy, $\Delta H_c$, fit to a linear dependence on glucose concentration (FIG. 10B), consistent with an osmolyte effect.

The initial values obtained by the local fits were used to obtain a global fit of the dependence of the fluorescent signal on glucose concentration and temperature at 1 mM $CaCl_2$ using conjugate gradient minimization of least squares difference between the object function described by equations 1-15 and the experimental observations (FIG. 11). Bootstrap analysis (randomly duplicating 25% of the experimental datapoints and resolving from the initial conditions) indicated that the solution is stable.

Figure 12:
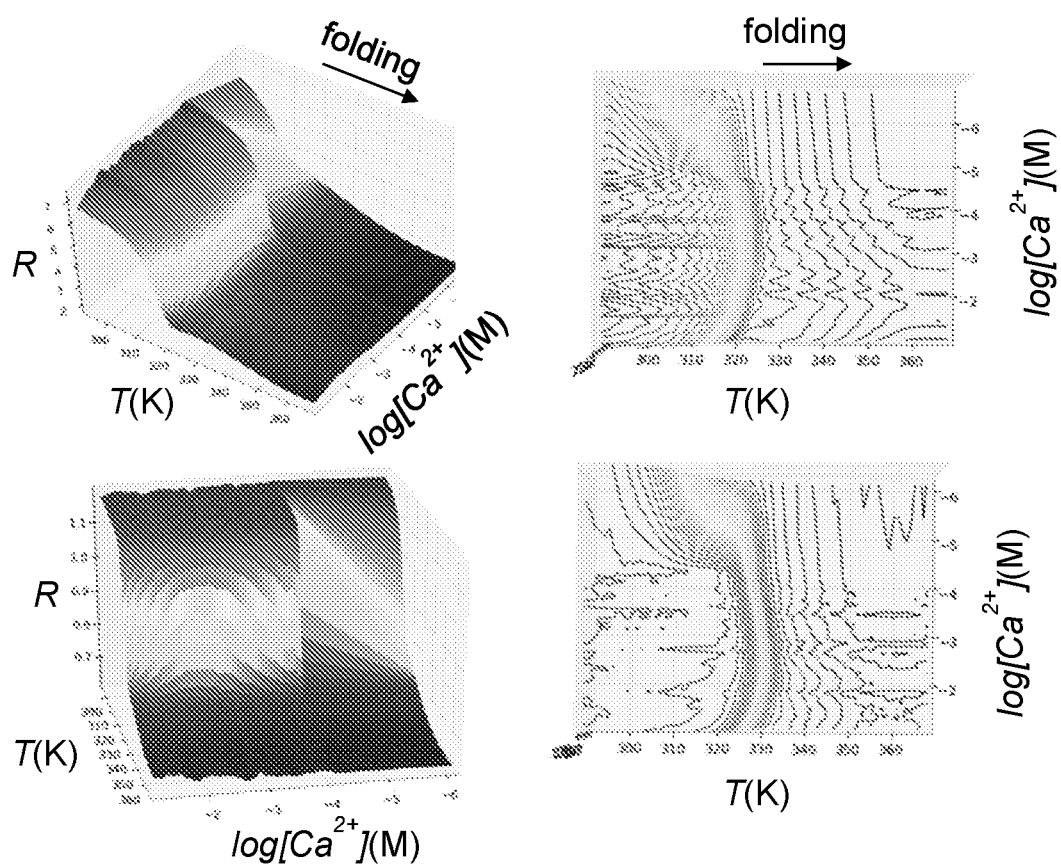
FIG. 12 are graphs showing the fluorescence response of GGBP183C·acrylodan (top) and BD_SM4·acrylodan (bottom) to Ca2+. Although there is no direct response to binding Ca2+, the stability of protein shifts in response.
Figure 13:
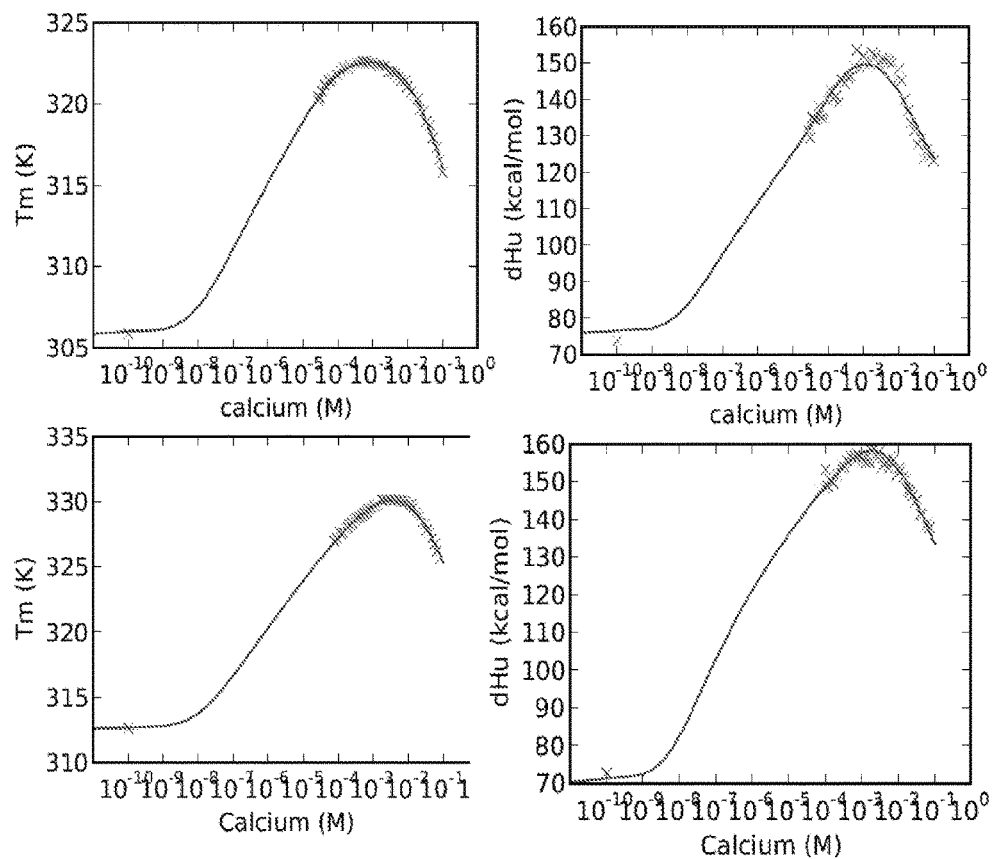
FIG. 13 are graphs showing the thermal stability shifts upon addition of Ca2+ to GGBP183C·acrylodan (top) and BD_SM4·acrylodan (bottom) in the absence of glucose. Green crosses, Tm (left) and ΔHu (right) values extracted from the experimental data; blue lines, calculated values. The calculated Kd values at 37° C. for GGBP183C·acrylodan are: single folded state site, 10.8 nM; single, medium-affinity denatured state, 0.37 mM; two, low-affinity denatured states 8.8 mM. The corresponding values for BD_SM4·acrylodan are 12.2 nM, 4.3 mM, and 11.9 mM.

GGBP binds $Ca^{2+}$ at a location remote from glucose (FIG. 1). The binding of $Ca^{2+}$ was investigated in the absence of glucose (FIG. 12). The fluorescence of acrylodan does not respond directly to $Ca^{2+}$ binding, unlike glucose. Nevertheless, $Ca^{2+}$ binding can be followed through its effect on protein stability (FIG. 13). Low $Ca^{2+}$ concentrations raise the stability of the protein significantly, indicating the presence of a high-affinity site in the native state, consistent with the protein structure. However, at elevated concentrations, this stabilization effect levels off and addition of $Ca^{2+}$ becomes destabilizing. This behavior indicates that the denatured state has multiple, low-affinity $Ca^{2+}$ binding sites.

These effects can be modeled accurately by a fit of the ligand- and temperature-dependent free energy of stability for $Ca^{2+}$ (Judge et al. Diabetes Technol. Thera. 2011, 13, 309-317; Layton et al. Biochemistry 2010, 49, 10831-10841).

$$\Delta G_U(T,L) = \Delta^{apo} G_U(T) + \Delta^D G_{b,Ca}(T,L) - \Delta^N G_{b,Ca}(T,L) + \Delta^{apo} G_O \qquad 19$$

The individual terms are cast in terms of T and $[Ca^{2+}]$ using equations 4-9. However, rather than fitting fluorescent landscape data directly using 1, $T_m$ and $\Delta H_u$ values are extracted at each $Ca^{2+}$ concentration using 16 and 17, and fit to the equation system by determining the root of 19 to obtain the calculated $T_m$ value. The relationship $$\Delta H_U(T,L) = \Delta^{apo} H_U + \Delta^D H_b(T,L) - \Delta^N H_b(T,L) \qquad 20$$

was used to obtain the calculated enthalpy at a given $Ca^{2+}$ concentration, where $$\Delta H_b(T,L) = \bar{y}(\Delta H_b + \Delta C_{p,b}(T-T)) \qquad 21$$

This analysis reveals that in the absence of glucose both GGBP183C·acrylodan and BD_SM4·acrylodan conjugates bind $Ca^{2+}$ at 37° C. with ~10 nM affinity in the native state at a single site, consistent with the protein structure, and have three low-affinity (ranging 0.4-12 mM) $Ca^{2+}$-binding sites in the denatured state.

Figure 14:
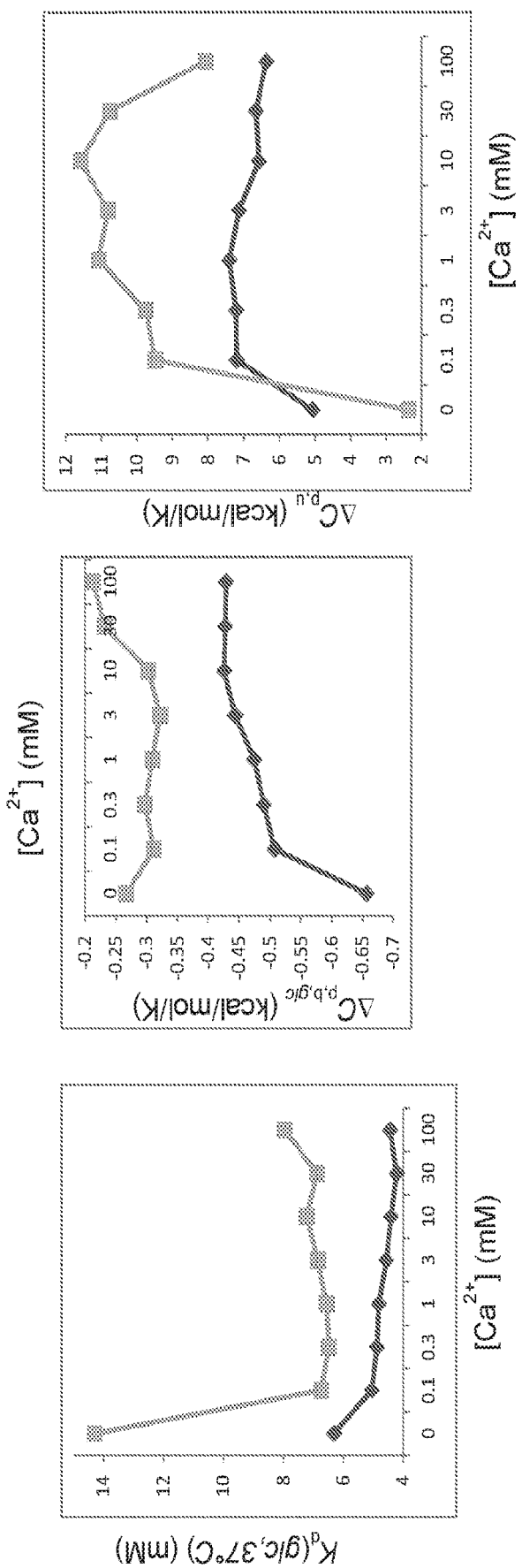
FIG. 14 are graphs showing the parameters extracted from landscapes that record the dependence of fluorescence on glucose concentrations and temperature at a given calcium concentration for GGBP183C·acrylodan (red) and BD_SM4·acrylodan (blue). Lines are drawn as a guide to trends only.

To investigate whether the glucose- and $Ca^{2+}$-binding sites interact in the folded state, fluorescent landscapes of glucose titrations were collected at eight different calcium concentrations. Each of these landscapes was fit individually to equation 1. From these fits the dependence of glucose binding on calcium could be determined (FIG. 14). Glucose affinity and binding and folding heat capacities are linked to calcium binding.

Figure 15:
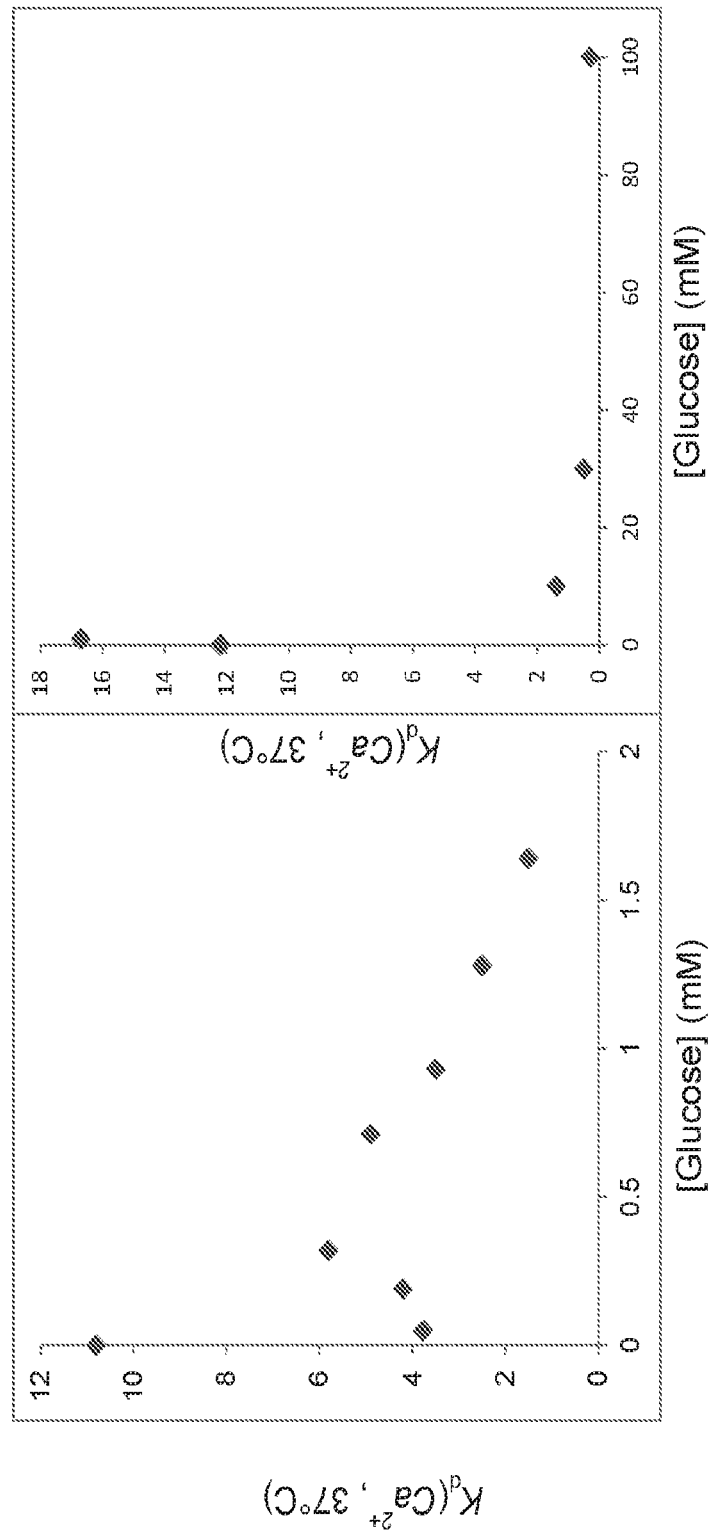
FIG. 15 are graphs showing the dependence of Ca2+ affinity on glucose for GGBP183C·acrylodan (left) and BD_SM4·acrylodan (right). Extraction of Tm and ΔHu values from the GGBP183C·acrylodan at non-zero glucose concentrations is confounded by effects on baselines by the conformational change in the glucose-saturated complex.

The dependence of calcium binding on glucose concentration also can be extracted from these landscapes, by fitting equation 19 to thermal melts at obtained at a particular glucose concentration (FIG. 15). This analysis reveals that $Ca^{2+}$ binding to the native state also is linked to the glucose binding, as would be expected.

Figure 16:
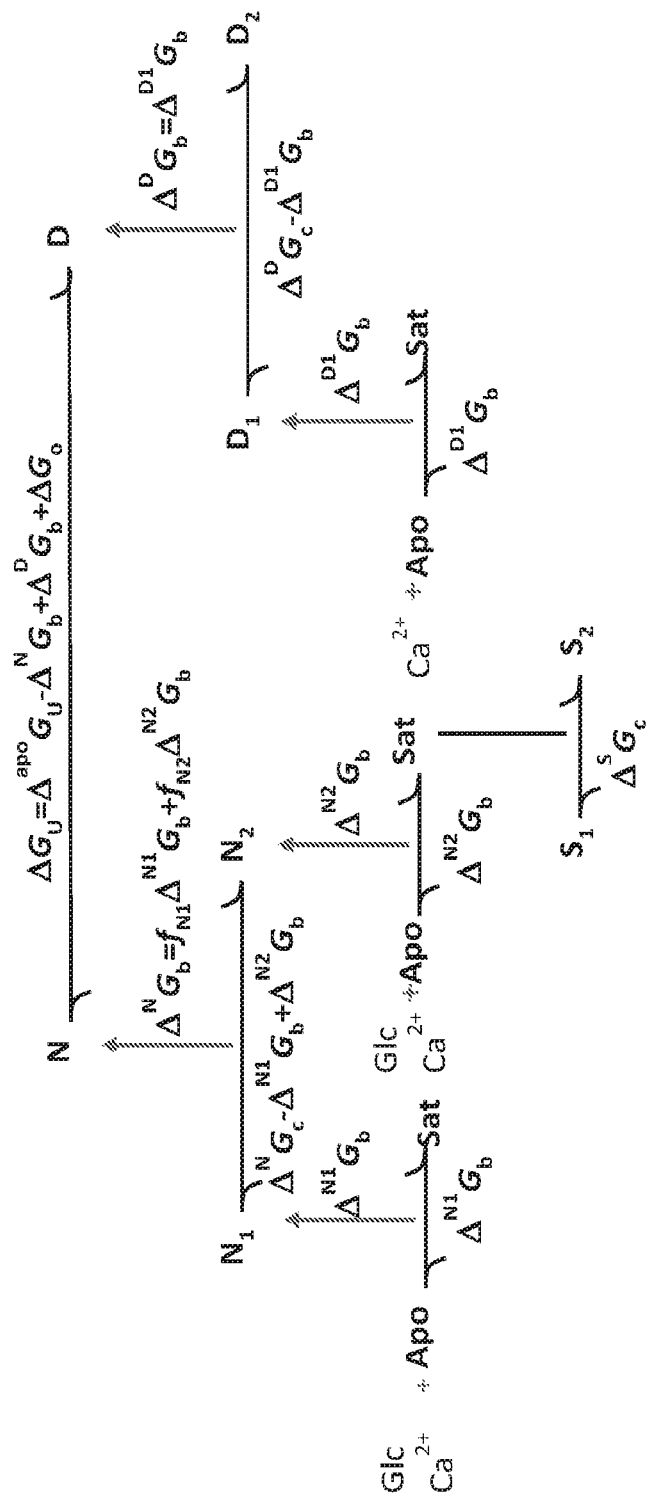
FIG. 16 is a schematic showing the representation of the binding, conformational change, and unfolding equilibria in GGBP and their sensitivity to glucose and calcium binding (also see FIG. 6).

Taken together, the landscapes reveal a complex set of interactions linking the binding of the two ligands to each other and to protein stability, summarized in FIG. 16. In this model, the folded state has two conformations, $N_1$ and $N_2$, which differ in their affinities for glucose and $Ca^{2+}$ and in their folding properties. Compared to $N_2$, the $N_1$ state has lower affinity for glucose and $Ca^{2+}$ and a lower $\Delta C_{p,u}$. This is consistent with the domain containing the $Ca^{2+}$ site being partially unfolded in the absence of ligand. $\Delta C_{p,u}$ is proportional to the difference in the solvent-accessible surface are in the unfolded and folded states. Accordingly, a form that has a partially unfolded state has a smaller heat capacity compared to a protein that adopts more structure. A partially unfolded state has been observed for GGBP by circular dichroism. In the absence of ligand $N_1$ is favored over $N_2$. As either ligand binds, the equilibrium shifts towards $N_2$, thereby increasing the affinity for the other ligand (this is a classic heterotropic cooperative binding effect), and altering the apparent thermal denaturation behavior. The equilibrium between $N_1$ and $N_2$ is different in GBP183C·acrylodan and BD_SM4·acrylodan: in the latter, $N_1$ is more favored, requiring higher concentrations of $Ca^{2+}$ or glucose to shift to $N_2$. In GGBP183C·acrylodan, the glucose-bound state of $N_1$, undergoes a further thermally driven conformational transition, associated with a change in fluorescence.

The unfolded state has three $Ca^{2+}$ binding sites that differ in affinity, but no glucose-binding site. The effect of $Ca^{2+}$ binding to the unfolded state is seen at elevated concentrations. This effect destabilizes the protein above ~3 mM calcium. The effect of $Ca^{2+}$ binding on $\Delta C_{p,u}$ is consistent with this model: at low concentrations, it organizes the partially unfolded state, increasing $\Delta C_{p,u}$ at elevated concentrations, it organizes the unfolded state, decreasing $\Delta C_{p,u}$ These effects can be combined into one unified thermodynamic model that describes the four-dimensional surface $s(T,[glucose],[Ca^{2+}])$. This model is currently being worked on.

Analysis of Systematic Errors

Figure 17:
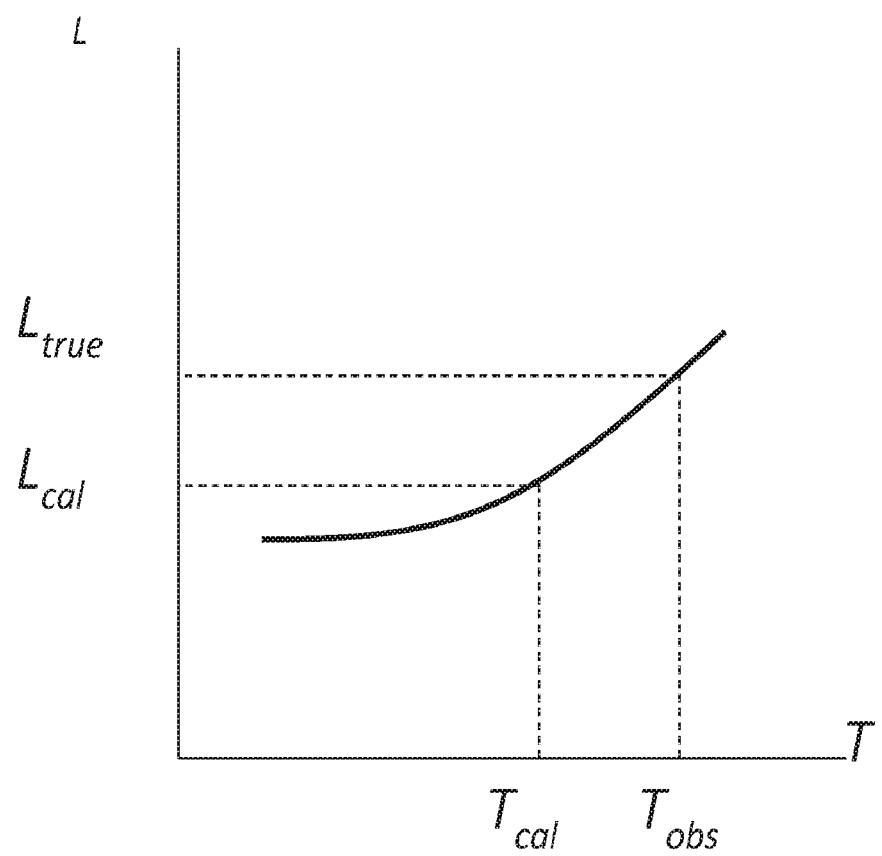
FIG. 17 is a graph showing the systematic calibration error due to the temperature dependence of glucose binding. Depicted is the variation of glucose concentration corresponding to a constant signal (isochrome) as a function of temperature. Tcal is the calibration temperature. Tobs, the actual temperature; Lcal and Ltrue the associated glucose concentrations.

At a given glucose concentration, the signal is sensitive to temperature and calcium concentration. Consequently a systematic error can be introduced in glucose measurements, if these factors are not taken into account. The thermodynamic model described above can be used to provide a quantitative analysis of such potential systematic errors by determining how the glucose concentration varies with temperature at constant signal: i.e., the error is determined by the temperature dependence of the isochrome (FIG. 17). The temperature dependent error for the variation shown in the figure is:

$$\varepsilon(T) = \frac{L_{true} - L_{cal}}{L_{cal}} \qquad 22$$

Figure 18:
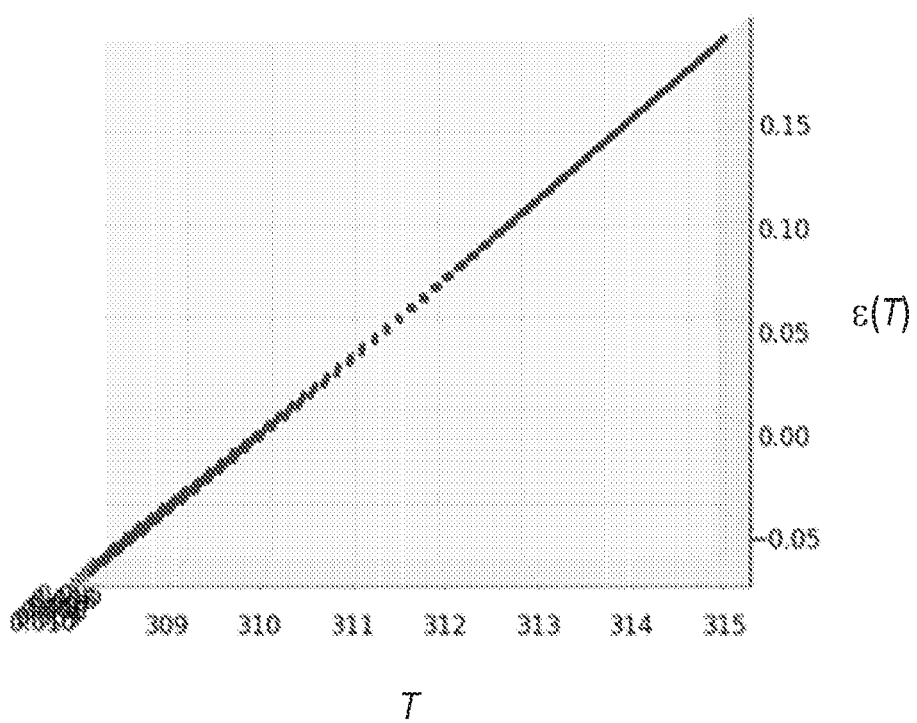
FIG. 18 is a graph showing the systematic temperature-dependent error in glucose concentration, ε(T), was calculated for BD_SM4·acrylodan in the 4-10 mM interval. The projection of this surface is shown, indicating that dε(T)/dT ~3.7% K−1.

This error function can be calculated from the thermodynamic models (FIG. 18). As can be seen, this systematic error is quite significant ε(T) ~3.7% for each degree away from the calibration temperature for BD_SM4·acrylodan. This means that in the diurnal range of 36° C.-37° C., the error is ±3.7% (7.4% range), whereas in the full pathophysiological range of 35° C.-42° C. it ranges from −7.4% to +18.5% (25.9% range).

The linkage between glucose and $Ca^{2+}$ binding also introduces a systematic error in a sensor calibrated at a given calcium concentration. However, in the 0.8-1.5 mM pathophysiological calcium concentration range, this effect is relatively small. The full-scale thermodynamic model is not yet complete, so we cannot calculate this error precisely. However, the variation of the isothermal $K_d$ for glucose at 37° C. is approximately 4.7±0.1 mM (FIG. 14), corresponding to a 2% error.

Affinity Tuning

Mutagenesis studies were carried out to (i) verify that the wild-type interactions between the protein and glucose persist in the GGBP183C·acrylodan conjugate; (ii) establish which interactions encode the dramatic lowering of glucose affinity of the GGBP183C·acrylodan conjugate; and (iii) identify variants that raise the glucose affinity at 37° C. to provide improved coverage of the response in the hyperglycemic region (10-33 mM), and lower it to improve coverage the hypoglycemic region (2-4 mM).

Analysis of Mutant Affinity Values: Isothermal glucose titrations were extracted from the fluorescent landscape or emission datasets as described above. Monochromatic emission intensities $I_\lambda$. (these intensities correspond to a band-pass intensity recorded with a physical filter in the case of the Roche LightCycler) were fit to $$I_\lambda = {}^{apo}\beta_\lambda (1-\bar{y}_{true}) + {}^{sat}\beta_\lambda \bar{y}_{true} \qquad 23$$

Where ${}^{apo}\beta_\lambda$ and ${}^{sat}\beta_\lambda$ are the fluorescence baselines associated with the ligand-free and ligand-bound states of the protein, respectively, and $\bar{y}_{true}$ the fractional saturation of the protein. Baseline functions can be constant, linear, or a second-order polynomial. For the ligand- and temperature-dependent fluorescence landscapes, we use a constant value for ${}^{apo}\beta_\lambda$, but ${}^{sat}\beta_\lambda$ is described by a linear dependence on glucose concentration, [L]:

$$^{apo}\beta_\lambda = a_x + b_x[L] \qquad 24$$

For a single glucose-binding site, the fractional saturation is given by $$\bar{y} = \frac{[L]}{[L]+K_d} \qquad 25$$

where [L] is the ligand (glucose) concentration and $K_d$ the dissociation constant, ${}^{true}K_d$ for $\bar{y}_{true}$ A dichromatic ratiometric signal is defined as the ratio of the intensities at two independent wavelengths, $\lambda_1$ and $\lambda_2$ $$R_{1,2} = I_{\lambda 1}/I_{\lambda 2} \qquad 26$$

This signal removes systematic error due to variations in conjugate concentration, and fluctuations in excitation source intensities, and detector-dependent changes in emission intensities. It is a key aspect for high-precision sensing using the reagentless fluorescently-responsive sensors described here. The ratiometric signal also can be fit to a binding isotherm:

$$R_{1,2} = {}^{apo}\beta_R(1-\bar{y}_R) + {}^{sat}\beta_R \bar{y}_R \qquad 27$$

where ${}^{apo}\beta_R$ and ${}^{sat}\beta_R$ are the baselines, and $\bar{y}_R$ the apparent fractional saturation of the protein (with ${}^{app}K_d$). In general, ${}^{true}K_d \neq {}^{app}K_d$; if both baselines are constant, a simple relationship can be derived relating ${}^{app}K_d$ to ${}^{true}K_d$:

$$^{app}K_d = {}^{true}K_d \frac{{}^{apo}I_{\lambda 2}}{{}^{sat}I_{\lambda 2}} \qquad 28$$

where ${}^{apo}I_{\lambda 2}$ and ${}^{sat}I_{\lambda 2}$ are the emission intensities of the monochromatic signal at wavelength $\lambda_2$ of the ligand-free and ligand-bound protein, respectively. Equation 28 illustrates that the ${}^{app}K_d$ values obtained by fits of 25 to ratiometric signals are wavelength dependent. To obtain wavelength-independent values needed for comparison of mutant proteins, it is necessary to simultaneously fit ${}^{app}K_d$ to the ratiometric signal and ${}^{true}K_d$ to the two monochromatic signals. For a given isothermal titration, values for ${}^{app}K_d$ and ${}^{true}K_d$ were obtained using a non-linear fitting algorithm in which these two parameters were simultaneously fit to the three experimental binding isotherms using equations 23 and 27, with the two monochromatic isotherms sharing the same ${}^{true}K_d$ value. Three separate pairs of linear ${}^{apo}\beta$ and ${}^{sat}\beta$ baselines were fit in this procedure. TABLES 1-5 record the ${}^{true}K_d$ values at 25° C., obtained by analysis of Roche LightCycler data in 488 nm and 510 nm channels. The uncertainty of the fit ('error') was obtained using a boot-strapping technique in which 37% of the data was replicated. In all cases, no binding was recorded if one of ${}^{app}K_d$ or ${}^{true}K_d$ exceeded 200 mM. The glucose constant of GGBP183 C-acrylodan is 4.21±0.08 mM at 25° C.

Alanine-Scanning Mutagenesis: The major, direct interactions between bound glucose and the protein (FIG. 2) were probed by alanine-scanning mutagenesis (TABLE 1). Loss of these interactions individually leads to significant loss in affinity, consistent with their hydrogen bond formation to the glucose hydroxyls, and van der Waals interactions with its pyranose ring.

TABLE 1

Alanine scanning mutagenesis.

| Mutation | $K_d^{298K}$(glucose)/mM | $T_m$/K | Description of wild-type residue position |
|---|---|---|---|
| Y10A | No binding | 326 | Interacts with D14 across the mouth of the binding site. Also makes contact with Acrylodan. |
| D14A | 174 ± 96 | 317 | Hydrogen bond with glucose-OH4. Also makes this contact with galactose. |
| F16A | No binding | 319 | Part of the aromatic sandwich. |
| N91A | No binding | 326 | Hydrogen bond to glucose-O6 hydroxyl. Weak contact with glucose-O5 (pyranose ring oxygen). |

TABLE 1-continued

Alanine scanning mutagenesis.

| Mutation | $K_d^{298K}$(glucose)/mM | $T_m$/K | Description of wild-type residue position |
|---|---|---|---|
| K92A | No binding | 323 | In the wild-type protein it interacts with Glu149 across the mouth of the protein. |
| H152A | No binding | 316 | Hydrogen bond to glucose·O6 hydroxyl. May make contact with the Acrylodan. |
| D154A | No binding | 320 | Hydrogen bond to glucose-O1. |
| R158A | No binding | 322 | Hydrogen bonds to glucose-O1 and -O2. |
| N211A | No binding | 317 | Hydrogen bond to glucose-O3. |
| D236A | No binding | 320 | Hydrogen bonds to glucose-O2 and -O3. |
| N256A | No binding | 324 | Weak hydrogen bonds to glucose-O1 and -O2. |

Affinity Tuning

Figure 19:
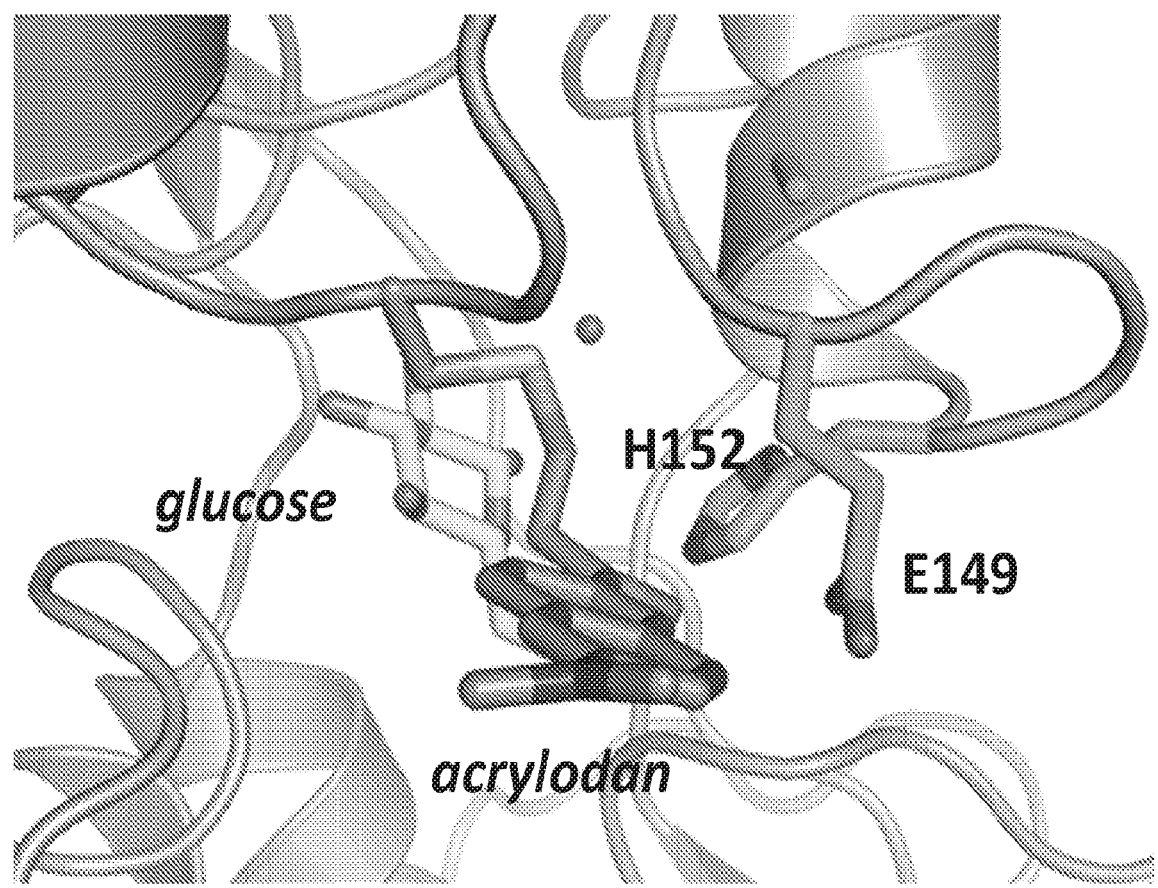
FIG. 19 is a drawing showing mutations at positions 149 (unfavorable interaction with acrylodan), 152 (hydrogen bond to glucose 6-OH), and 155 (interaction with water) tune the glucose affinity.

Interactions with the Buried Water Molecule that Replaces W183:A155 Mutants: The methyl group of alanine 155 points towards a buried water molecule that replaces the W183 indole ring in the GGBP183C·acrylodan conjugate (FIG. 19). In the wild-type protein, A155 is adjacent to the face of the W183 indole ring that does not touch the bound glucose (FIG. 19). We constructed a series of mutations to test whether it is possible for amino acid side-chains placed at position 155 to form a van der Waals contact between the protein and the glucose pyranose ring without interfering with the acrylodan conjugate attached to 183C (TABLE 2).

We also identified a variant at this position, A155N, which has the interesting property that glucose binding has the opposite effect on fluorescence: it increases the 488/580 ratio. Binding of glucose therefore shifts the emission wavelength maximum to the blue instead of the red.

TABLE 2

Mutations at position 155.

| Mutation | $K_d^{298K}$(glucose)/mM | $T_m$/K |
|---|---|---|
| A155S | No binding | 321 |
| A155H | 13.5 ± 2.5 | 314 |
| A155L | No binding | 320 |
| A155F | No binding | 321 |
| A155Y | No binding | 321 |
| A155N | 5.9 ± 1.0 | 320 |
| A155K | No binding | 318 |
| A155M | No binding | 321 |
| A155W | No binding | 322 |
| A155Q | No binding | 321 |

The Effect of Potentially Unfavorable Contacts with Acrylodan: E149 Mutants: The E149 carboxylate is in close proximity to the acrylodan carbonyl (FIG. 19). We constructed three variants to remove or reverse this charge (TABLE 3). All three variants improved the glucose affinity consistent with the removal of an unfavorable interaction. Furthermore, these higher affinity mutants extend the coverage into the hypoglycemic range—a desirable achievement that exceeds the specification in the original Aims.

TABLE 3

Mutations at position 149.

| Mutation | $K_d^{298K}$(glucose)/mM | $T_m$/K |
|---|---|---|
| E149Q | 0.46 ± 0.01 | 322 |
| E149S | 0.34 ± 0.01 | 320 |
| E149K | 1.44 ± 0.04 | 321 |

Tuning Affinity by Altering Direct Interactions with Glucose: Construction of variants with affinities in the 10-33 mM range requires that interactions are perturbed only minimally (2-5 fold loss in interaction strength). We explored whether it is possible to achieve such subtle changes through alteration of individual hydrogen bond or van der Waals contact strengths by mutagenesis at eight positions that form direct interactions with glucose (FIG. 2; TABLE 4). Three of the 34 mutants that were tried yielded the desired result (H152N, H152Q, and H152F). All three involve changes in histidine 152, which forms a hydrogen bond through N, with the glucose 6-hydroxyl (FIG. 19). These three mutants cover the range specified in the original Aims.

TABLE 4

Tuning affinity by altering interactions with glucose.

| Mutation | $K_d^{298K}$(glucose)/mM | $T_m$/K | Description |
|---|---|---|---|
| D14E | No binding | 318 | Hydrogen bonds with glucose-OH4. Also makes this contact with galactose. |
| D14Q | No binding | | |
| D14N | No binding | 317 | |
| D14S | No binding | | |
| D14T | No binding | 316 | |
| D14H | No binding | 317 | |
| D14L | No binding | 311 | |
| D14Y | No binding | | |
| D14F | No binding | | |
| F16L | No binding | 321 | Part of the aromatic sandwich. |
| D154N | No binding | 318 | Hydrogen bonds to glucose-O1. |
| R158K | No binding | 318 | Hydrogen bonds to glucose-O1 and -O2. |
| D236N | No binding | 320 | Hydrogen bonds to glucose-O2 and -O3. |
| N256D | No binding | 321 | Weak hydrogen bonds to glucose-O1 and -O2. |

TABLE 4-continued

Tuning affinity by altering interactions with glucose.

| Mutation | $K_d^{298K}$(glucose)/mM | $T_m$/K | Description |
|---|---|---|---|
| H152F | 21.1 ± 0.9. | 321 | Hydrogen bonds to glucose-O6 hydroxyl. May make contact with acrylodan. |
| H152Q | 25.8 ± 2.0 | 322 | |
| H152N | 18.8 ± 1.3 | 322 | |
| H152K | No binding | 319 | |
| N211Y | No binding | 316 | Hydrogen bonds to glucose-O3. |
| N211F | No binding | 323 | |
| N211W | No binding | 328 | |
| N211K | No binding | 315 | |
| N211Q | No binding | 317 | |
| N211S | No binding | 319 | |
| N211H | No binding | 320 | |
| N211M | No binding | 317 | |
| M182W | No binding | 322 | Adjacent to acrylodan. |

Specificity

The galactose affinities for those mutants that bind glucose were also determined.

TABLE 5

Galactose affinities.

| Mutation | $K_d^{298K}$(glucose)/mM | $K_d^{298K}$(galactose)/mM |
|---|---|---|
| D14A | 174 ± 96 | 90 ± 21 |
| E149Q | 0.46 ± 0.01 | 10.8 ± 0.4 |
| E149S | 0.34 ± 0.01 | 12.7 ± 15 |
| E149K | 1.44 ± 0.04 | 40.2 ± 1.3 |
| H152F | 21.1 ± 0.9 | No binding |
| H152N | 18.8 ± 1.3 | No binding |
| H152Q | 25.8 ± 2.0 | No binding |
| A155H | 13.5 ± 2.5 | 17.7 ± 2.1 |
| A155N | 5.9 ± 1.0 | 7.5 ± 1.0 |

Extending the Detection Range in a Composite Sensor

Figure 20A:
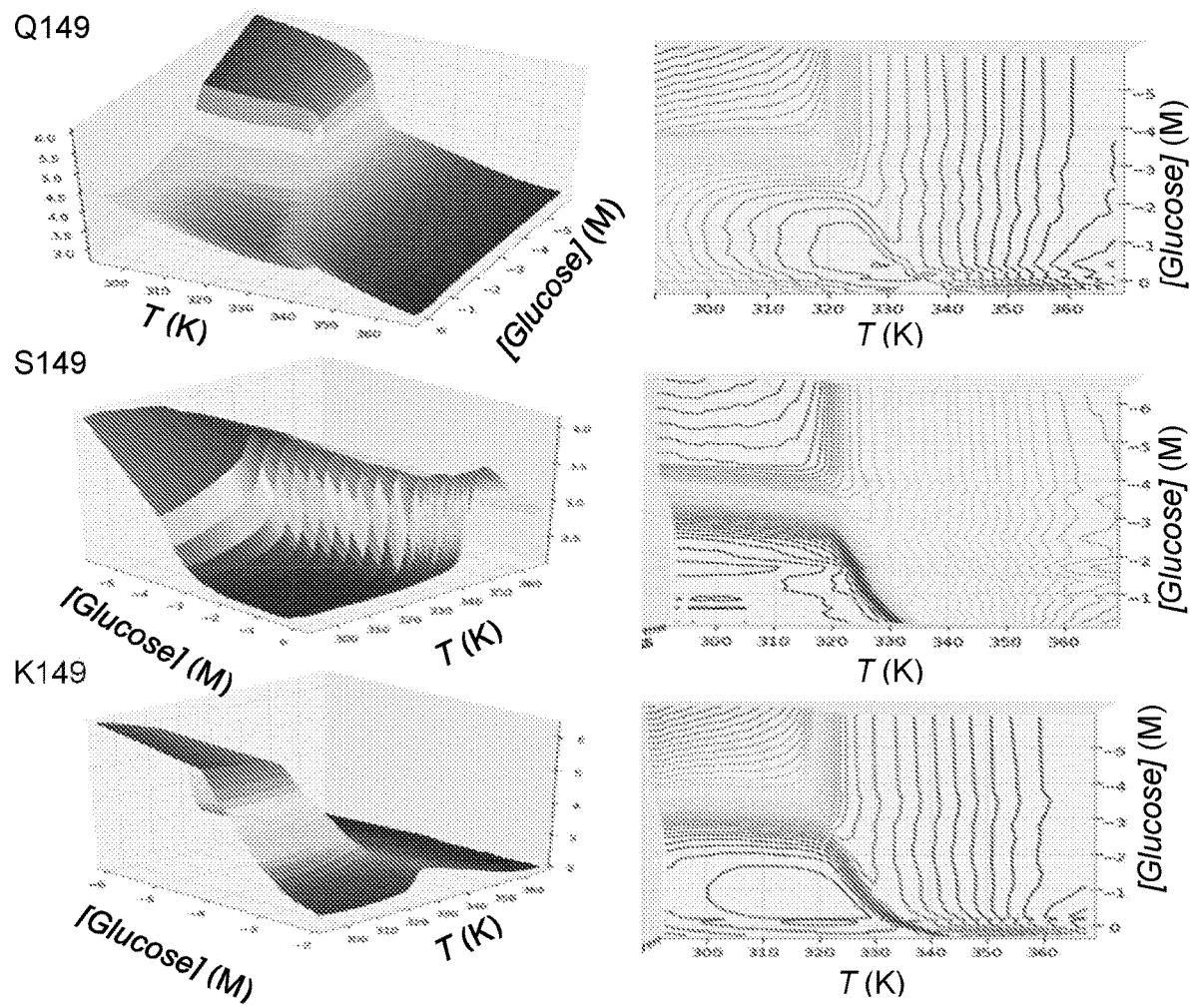
FIG. 20 is a drawing showing the ratioametric fluorescent signal responses with respect to temperature and glucose of the 183C-acrylodan conjugates of seven mutants that respond in the pathophysiological concentration range (see Tables 1-4 for details of their ligand-binding affinities). For each mutant, two different views are shown: a three-dimensional perspective to illustrate the qualitative character of the fluorescent landscape, and a projection to enable direct comparison between the landscapes.
Figure 20B:
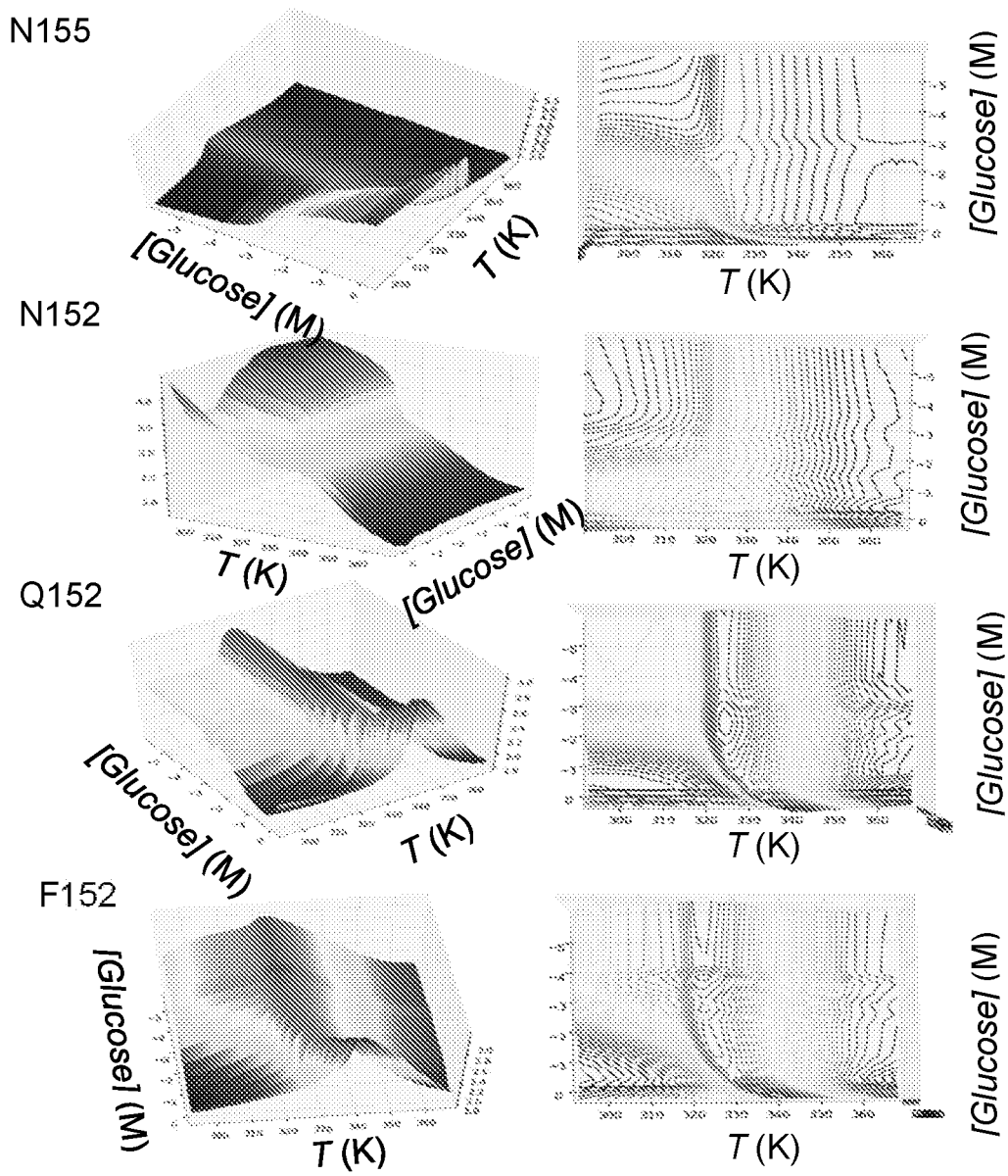

Seven proteins have been identified that extend the detection range into the hypo and hyperglycemic regions. Each of the sensors exhibits a distinct fluorescent landscape (FIG. 20). Their isochromes have unique temperature signatures that arise from individual temperature dependencies on glucose binding, conformational changes, and baseplanes. This means that, in principle, temperature correction can be achieved by analyzing the signals of several sensors in combination.

Figure 21:
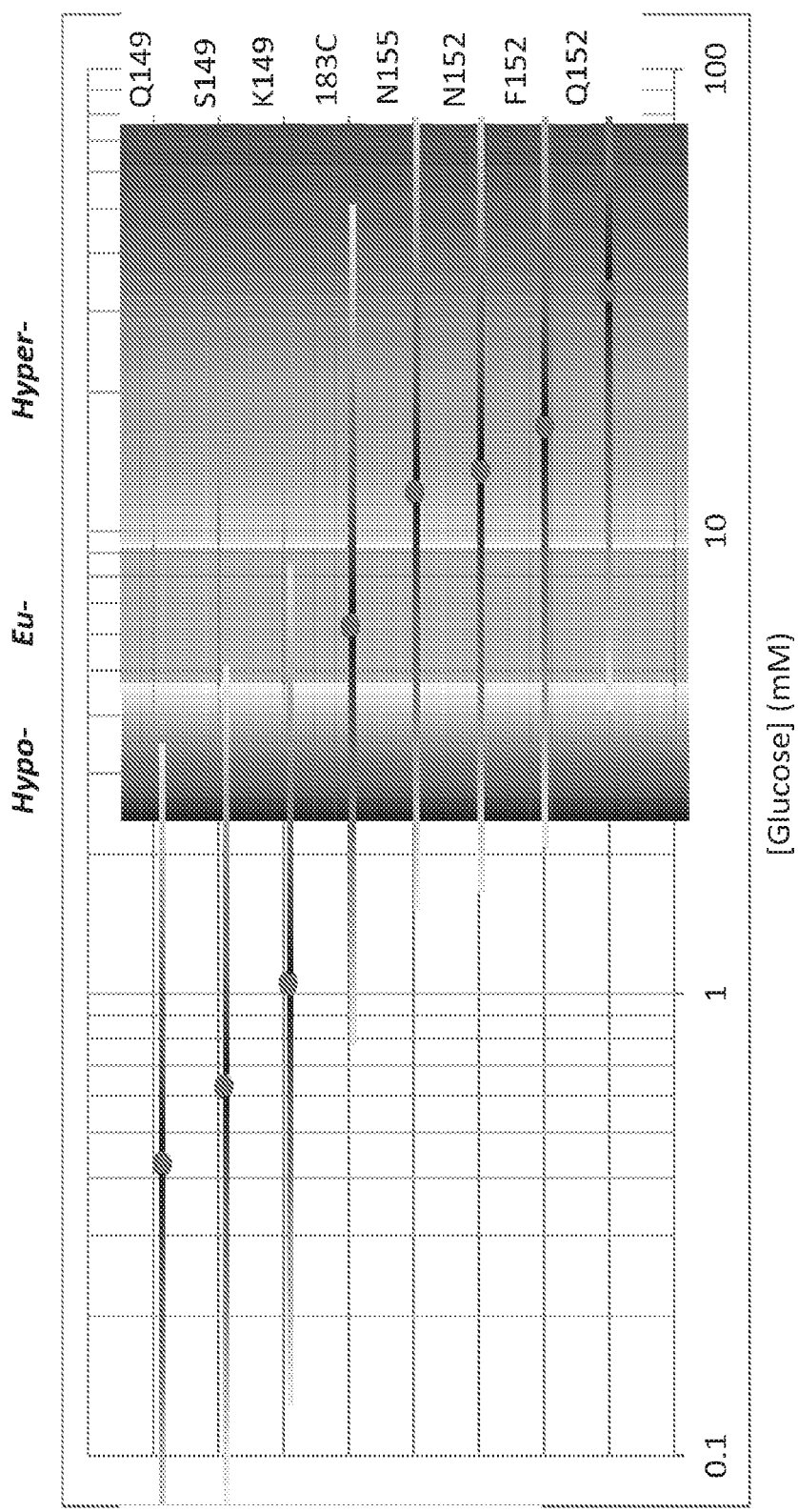
FIG. 21 is a schematic that illustrates over what glucose concentration ranges each sensor is expected to perform with high accuracy.

A minimum of three can be combined with the current sensor to construct a four-component composite sensor has a significantly extended high-accuracy detection range (FIG. 21).

Example 2

Figure 22:
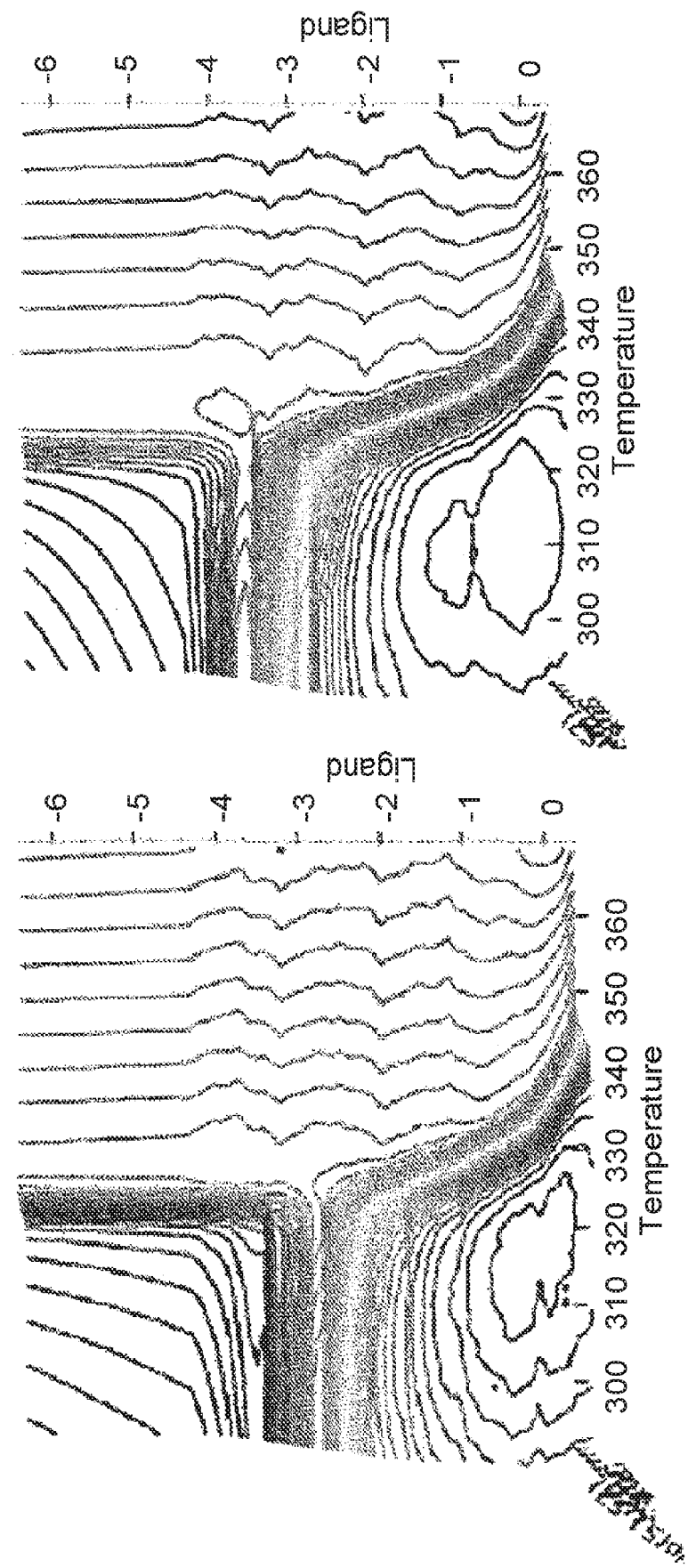
FIG. 22 is a drawing showing the ratiometric signal response with respect to temperature and glucose concentration of the 16C-acrylodan and 16C-badan conjugates.

Properties of the F16C Endosteric Mutation of E. coli Glucose-Galactose Binding Protein The acrylodan conjugate of the W183C mutant of performs well as a reagentless, fluorescently responsive sensor. This endosteric mutant replaces the tryptophan residue at position 183, which makes extensive van der Waals contacts with bound glucose or galactose. The opposite face of the sugar pyranose ring makes similarly extensive contacts with the phenylalanine residue at position 16. To test whether a similar endosteric mutant could function as an effective ratiometric sensor, the F16C mutant was constructed by total gene synthesis, and its acrylodan and badan conjugates were prepared. Both conjugates exhibited excellent ratiometric signals in response to glucose. The fluorescent landscapes of both conjugates (FIG. 22) bear a remarkable resemblance to the behavior of the GGBPI 83C-acrylodan conjugate (FIG. 5). These conjugates therefore can be used in optrodes or other sensors in the same manner as the GGBP183C-acrylodan. The glucose affinities of the GGBP16C-acrylodan and GGBP16C-badan conjugates are ~0.2 mM at 25° C. It is anticipated that the affinity of these sensors also can be tuned by mutagenesis.

Example 3

Glucose and Galactose Affinities

In addition to the Roche LightCycler, which has a limited choice of emission wavelengths, data for selected mutants also was measured at room temperature on a Nanodrop3300 (Thermo Scientific) fluorimeter, which records full emission spectra. Emission intensities at a particular wavelength were extracted by integration of the spectral emission intensities over a 20-nm interval centered on that wavelength. Results are shown in TABLE 6.

TABLE 6

Glucose and galactose affinities of ecGBP_183C mutants labeled with Acrylodan[a].

| | Response | | Emission wavelength (nm) | | Affinities (mM)[d] Glucose | | Emission wavelength (nm) | | Affinities (mM)[d] Galactose | |
|---|---|---|---|---|---|---|---|---|---|---|
| Mutation | Shape[b] | Intensity[c] | $\lambda_1$ | $\lambda_2$ | $^{app}K_d$ | $^{true}K_d$ | $\lambda_1$ | $\lambda_2$ | $^{app}K_d$ | $^{true}K_d$ |
| — | d | – | 483 | 507 | 6.0 | 4.4 | 483 | 510 | 31 | 24 |
| E149K | d | – | 483 | 507 | 1.5 | 1.2 | 483 | 510 | 34 | 27 |
| E149Q | d | – | 483 | 491 | 0.6 | 0.43 | 483 | 510 | 2.3 | 2.1 |
| E149S | d | – | 483 | 519 | 0.38 | 0.36 | 487 | 515 | 6.8[e] | 5.4[e] |

TABLE 6-continued

Glucose and galactose affinities of ecGBP_183C mutants labeled with Acrylodan[a].

| | Response | | Emission wavelength (nm) | | Affinities (mM)[d] Glucose | | Emission wavelength (nm) | | Affinities (mM)[d] Galactose | |
|---|---|---|---|---|---|---|---|---|---|---|
| Mutation | Shape[b] | Intensity[c] | $\lambda_1$ | $\lambda_2$ | $^{app}K_d$ | $^{true}K_d$ | $\lambda_1$ | $\lambda_2$ | $^{app}K_d$ | $^{true}K_d$ |
| H152F | d | − | 483 | 511 | 15 | 16 | 483 | 510 | nb | nb |
| H152N | d | − | 487 | 495 | 20 | 15 | 483 | 510 | 21[e] | 21[e] |
| H152Q | d | − | 487 | 511 | 4.6 | 5.1 | 487 | 515 | nb | nb |
| A155F | m | + | 511 | 466 | 0.06 | 0.06 | 491 | 511 | 0.82 | 0.93 |
| A155M | m | + | 507 | 466 | 0.05 | 0.05 | 491 | 520 | 6.7[e] | 8.7[e] |
| A155N | d | + | 487 | 510 | 0.14 | 0.23 | 491 | 515 | 4.5 | 6.6 |
| A155S | m? | + | 495 | 511 | 0.31 | 0.35 | 495 | 510 | nb | nb |
| N211Q | d | − | 479 | 510 | 29 | 22 | 479 | 510 | nb | nb |

[a]Signals S.
[b]m, monochromatic; d, dichromatic (i.e. spectral shape changes); 0, no change in the glucose titration.
[c]+, increases in response to ligand; −, decreases; 0, no change in the glucose titration.
[d]Blank entries, no measurements; nb, no binding.
[e]Noisy data.

Signals S (either single-wavelength emission intensities, $I_\lambda$, or ratios of intensities at two wavelengths, $R_{12}$) were fit to ligand-binding isotherms:

$$S = {^{apo}\beta}(1-\bar{y}) + {^{sat}\beta}\bar{y} \qquad 29$$

where $^{apo}\beta$ and $^{sat}\beta$ are the baselines in the ligand-free and ligand-bound states, respectively, and $\bar{y}$ is the fractional occupancy of the binding sites. Baseline functions can be constant ($^{apo}\beta$), or linearly dependent on ligand ($^{sat}\beta$). For a single ligand-binding site, the fractional saturation is given by $$\bar{y} = \frac{[L]}{[L] + K_d} \qquad 30$$

where [L] is the ligand concentration and $K_d$ the dissociation constant corresponding to $^{app}K_d$ or $^{true}K_d$ for fits to $R_{12}$ (weighted by the relative contributions of $^{sat}\beta$ at the two different wavelengths) and $I_\lambda$ respectively. For a given isothermal titration, values for $^{app}K_d$ and $^{true}K_d$ were obtained using a non-linear fitting algorithm in which these two parameters were simultaneously fit to the three experimental binding isotherms using equations 29 and 30, with the two monochromatic isotherms sharing the same $^{true}K_d$ value. Three separate pairs of $^{apo}\beta$ and $^{sat}\beta$ were fit in this procedure.

A ratiometric signal at a given point in a titration series, $R_{12}(t)$, is given by the ratio of intensities at two wavelengths, $^{obs}I(\lambda_1,t)$, $^{obs}I(\lambda_2,t)$ in the emission spectrum measured at that point:

$$R_{12}(t) = \frac{a_t^{obs} I(\lambda_1, t)}{a_t^{obs} I(\lambda_2, t)} \qquad 31$$

where $\alpha_t$ is an attenuation factor that describes the effect of variations in sample size (i.e. the amount of observable fluorophore) in the $t^{th}$ sample on the wavelength-independent intensity of the entire emission spectrum. Following a fit of the titration series using equations 29 and 30, $\alpha_t$ values can be recovered by taking the average comparison of the observed and calculated intensities at the two wavelengths:

$$a_t = \frac{1}{2}\left( \frac{^{calc}I(\lambda_1, t)}{^{obs}I(\lambda_1, t)} + \frac{^{calc}I(\lambda_2, t)}{^{obs}I(\lambda_2, t)} \right) \qquad 32$$

The $a_t$ value can then be applied to all wavelengths to obtain an emission spectrum of the $t^{th}$ titration point corrected for variations in sample size:

$$^{corr}I(\lambda) = a_t {^{obs}I(\lambda)} \qquad 33$$

where $^{corr}I(\lambda)$ and $^{obs}I(\lambda)$ are the wavelength-dependent intensities of the corrected and observed emission spectra, respectively.

Note that the $^{app}K_d$ values are dependent on the choice of the ratiometric wavelengths:

$$^{app}K_d = {^{true}K_d} \frac{^{apo}I_{\lambda 2}}{^{sat}I_{\lambda/2}} \qquad 34$$

where $^{apo}I_{\lambda,2}$ and $^{apo}I_{\lambda,2}$ are the emission intensities of the monochromatic signal at $I_2$ of the ligand-free and ligand-bound protein, respectively.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A biosensor comprising a) a polypeptide comprising a ligand binding site and (i) one or more mutations as compared to SEQ ID NO:112 (wild-type *E. coli* GGBP) that alter the ligand binding affinity of the polypeptide; and b) a reporter conjugated to the polypeptide, wherein when the polypeptide consists of a single mutation, the single mutation is F16C, wherein the ligand-bound biosensor results in a reporter-generated signal that is different from the unbound biosensor, and wherein the ligand is selected from the group consisting of glucose, galactose, and a combination thereof.

Clause 2. The biosensor of clause 1, wherein the reporter is conjugated to F16C.

Clause 3. The biosensor of clause 1, wherein the polypeptide further comprises (ii) at least one additional mutation that replaces an amino acid with a cysteine.

Clause 4. The biosensor of clause 3, wherein the reporter is conjugated to the cysteine.

Clause 5. The biosensor of any one of the preceding clauses, wherein the biosensor comprises a single reporter.

Clause 6. The biosensor of any one of the preceding clauses, wherein the reporter comprises a fluorophore and wherein the signal is a fluorescent signal.

Clause 7. The biosensor of clause 6, wherein the fluorophore is selected from the group consisting of acrylodan and badan.

Clause 8. The biosensor of clause 6, wherein the signal comprises an emission intensity of the fluorophore recorded at one or more wavelengths.

Clause 9. The biosensor of clause 6, wherein the change in signal comprises a shift in the one or more wavelengths.

Clause 10. The biosensor of clause 6, wherein the signal comprises a ratio of emission intensities recorded at two or more wavelengths.

Clause 11. The biosensor of clause 6, wherein the change in signal comprises a shift in two or more wavelengths.

Clause 12. The biosensor of any one of clauses 3-11, wherein the at least one additional mutation (ii) is W183C.

Clause 13. The biosensor of clause 12, wherein the reporter is conjugated to W183C.

Clause 14. The biosensor of any one of clauses 3-13, wherein each mutation (i) is a mutation to an amino acid selected from the group consisting of Y10, D14, F16, N91, K92, E149, H152, D154, A155, R158, M182, N211, D236, and N256, and combinations thereof.

Clause 15. The biosensor of any one of clauses 3-14, wherein each mutation (i) is selected from the group consisting of Y10A, D14A, D14Q, D14N, D14S, D14T, D14E, D14H, D14L, D14Y, D14F, F16L, F16A, N91A, K92A, E149K, E149Q, E149S, H152A, H152F, H152Q, H152N, D154A, D154N, A155S, A155H, A155L, A155F, A155Y, A155N, A155K, A155M, A155W, A155Q, R158A, R158K, M182W, N211F, N211W, N211K, N211Q, N211S, N211H, N211M, D236A, D236N, N256A, and N256D, and combinations thereof.

Clause 16. The biosensor of any one of clauses 3-15, wherein the mutation (i) affects the interaction of the polypeptide with bound glucose, wherein the interaction is with a portion of the glucose selected from the group consisting of 1-hydroxyl, 2-hydroxyl, 3-hydroxyl, 4-hydroxyl, 6-hydroxyl, pyranose ring, and combinations thereof.

Clause 17. The biosensor of any one of clauses 3-16, wherein the mutation (i) affects the interaction of the mutant polypeptide with the reporter group.

Clause 18. The biosensor of any one of clauses 3-17, wherein the mutation (i) affects the interaction of the mutant polypeptide with a water molecule.

Clause 19. The biosensor of any one of the preceding clauses, wherein the polypeptide has an affinity ($K_D$) for glucose within the concentration range of glucose in vivo for a subject.

Clause 20. The biosensor of any one of the preceding clauses, wherein the polypeptide has an affinity ($K_D$) for galactose within the concentration range of galactose in vivo for a subject.

Clause 21. The biosensor of any one of clauses 19 and 20, wherein the subject is a mammal.

Clause 22. The biosensor of any one of clauses 19 and 20, wherein the subject is a primate or non-primate.

Clause 23. The biosensor of clause 22, wherein the subject is a non-primate selected from a cow, pig, camel, llama, horse, goat, rabbit, sheep, hamsters, guinea pig, cat, dog, rat, and mouse.

Clause 24. The biosensor of clause 22, wherein the subject is a primate selected from a monkey, chimpanzee, and human.

Clause 25. The biosensor of clause 24, wherein the subject is a human.

Clause 26. The biosensor of any one of the preceding clauses, wherein the polypeptide has an affinity ($K_D$) for glucose in the range of about 0.2 mM to about 100 mM.

Clause 27. The biosensor of any one of the preceding clauses, wherein the polypeptide has an affinity ($K_D$) for galactose in the range of about 0.8 mM to about 100 mM.

Clause 28. The biosensor of any one of the preceding clauses, wherein the biosensor is capable of detecting glucose in the hypoglycemic, hyperglycemic, and hyperglycemic-hyperosmotic ranges.

Clause 29. The biosensor of any one of the preceding clauses, wherein the biosensor is capable of detecting glucose in the range of about 0.1 mmol/L to about 120 mmol/L.

Clause 30. The biosensor of any one of the preceding clauses, wherein the biosensor is capable of detecting glucose in the range of about 4 mmol/L to about 33 mmol/L.

Clause 31. The biosensor of any one of the preceding clauses, wherein the biosensor is capable of detecting galactose in the range of about 0.2 mM to about 400 mM.

Clause 32. The biosensor of any one of the preceding clauses, wherein the mutant polypeptide comprises an amino acid sequence selected from the group consisting of SEQ ID NOs: 1-54.

Clause 33. A polypeptide comprising the amino acid sequence of SEQ ID NO: 1.

Clause 34. A polypeptide comprising the amino acid sequence of SEQ ID NO: 2.

Clause 35. A polypeptide comprising the amino acid sequence of SEQ ID NO: 3.

Clause 36. A polypeptide comprising the amino acid sequence of SEQ ID NO: 4.

Clause 37. A polypeptide comprising the amino acid sequence of SEQ ID NO: 5.

Clause 38. A polypeptide comprising the amino acid sequence of SEQ ID NO: 6.

Clause 39. A polypeptide comprising the amino acid sequence of SEQ ID NO: 7.

Clause 40. A polypeptide comprising the amino acid sequence of SEQ ID NO: 8.

Clause 41. A polypeptide comprising the amino acid sequence of SEQ ID NO: 9.

Clause 42. A polypeptide comprising the amino acid sequence of SEQ ID NO: 10.

Clause 43. A polypeptide comprising the amino acid sequence of SEQ ID NO: 11.

Clause 44. A polypeptide comprising the amino acid sequence of SEQ ID NO: 12.

Clause 45. A polypeptide comprising the amino acid sequence of SEQ ID NO: 13.

Clause 46. A polypeptide comprising the amino acid sequence of SEQ ID NO: 14.

Clause 47. A polypeptide comprising the amino acid sequence of SEQ ID NO: 15.

Clause 48. A polypeptide comprising the amino acid sequence of SEQ ID NO: 16.

Clause 49. A polypeptide comprising the amino acid sequence of SEQ ID NO: 17.

Clause 50. A polypeptide comprising the amino acid sequence of SEQ ID NO: 18.

Clause 51. A polypeptide comprising the amino acid sequence of SEQ ID NO: 19.

Clause 52. A polypeptide comprising the amino acid sequence of SEQ ID NO: 20.

Clause 53. A polypeptide comprising the amino acid sequence of SEQ ID NO: 21.

Clause 54. A polypeptide comprising the amino acid sequence of SEQ ID NO: 22.

Clause 55. A polypeptide comprising the amino acid sequence of SEQ ID NO: 23.

Clause 56. A polypeptide comprising the amino acid sequence of SEQ ID NO: 24.

Clause 57. A polypeptide comprising the amino acid sequence of SEQ ID NO: 25.

Clause 58. A polypeptide comprising the amino acid sequence of SEQ ID NO: 26.

Clause 60. A polypeptide comprising the amino acid sequence of SEQ ID NO: 27.

Clause 61. A polypeptide comprising the amino acid sequence of SEQ ID NO: 28.

Clause 62. A polypeptide comprising the amino acid sequence of SEQ ID NO: 29.

Clause 63. A polypeptide comprising the amino acid sequence of SEQ ID NO: 30.

Clause 64. A polypeptide comprising the amino acid sequence of SEQ ID NO: 31.

Clause 65. A polypeptide comprising the amino acid sequence of SEQ ID NO: 32.

Clause 66. A polypeptide comprising the amino acid sequence of SEQ ID NO: 33.

Clause 67. A polypeptide comprising the amino acid sequence of SEQ ID NO: 34.

Clause 68. A polypeptide comprising the amino acid sequence of SEQ ID NO: 35.

Clause 69. A polypeptide comprising the amino acid sequence of SEQ ID NO: 36.

Clause 70. A polypeptide comprising the amino acid sequence of SEQ ID NO: 37.

Clause 71. A polypeptide comprising the amino acid sequence of SEQ ID NO: 38.

Clause 72. A polypeptide comprising the amino acid sequence of SEQ ID NO: 39.

Clause 73. A polypeptide comprising the amino acid sequence of SEQ ID NO: 40.

Clause 74. A polypeptide comprising the amino acid sequence of SEQ ID NO: 41.

Clause 75. A polypeptide comprising the amino acid sequence of SEQ ID NO: 42.

Clause 76. A polypeptide comprising the amino acid sequence of SEQ ID NO: 43.

Clause 77. A polypeptide comprising the amino acid sequence of SEQ ID NO: 44.

Clause 78. A polypeptide comprising the amino acid sequence of SEQ ID NO: 45.

Clause 79. A polypeptide comprising the amino acid sequence of SEQ ID NO: 46.

Clause 80. A polypeptide comprising the amino acid sequence of SEQ ID NO: 47.

Clause 81. A polypeptide comprising the amino acid sequence of SEQ ID NO: 48.

Clause 82. A polypeptide comprising the amino acid sequence of SEQ ID NO: 49.

Clause 83. A polypeptide comprising the amino acid sequence of SEQ ID NO: 50.

Clause 84. A polypeptide comprising the amino acid sequence of SEQ ID NO: 51.

Clause 85. A polypeptide comprising the amino acid sequence of SEQ ID NO: 52.

Clause 86. A polypeptide comprising the amino acid sequence of SEQ ID NO: 53.

Clause 87. A polypeptide comprising the amino acid sequence of SEQ ID NO: 54.

Clause 88. A polynucleotide encoding the polypeptide of any one of the preceding clauses.

Clause 89. The polynucleotide of clause 88, wherein the polynucleotide comprises at least one sequence selected from the group consisting of SEQ ID NOs: 56-109.

Clause 90. A vector comprising the polynucleotide of clause 88 or 89.

Clause 91. A panel comprising a plurality of biosensors according to any one of clauses 1-32.

Clause 92. The panel of clause 91, wherein the panel comprises a composite sensor or an array.

Clause 93. The panel of clause 92, wherein the array is selected from a multichannel array or multiplexed array.

Clause 94. The panel of any one of clauses 91-93, wherein each biosensor comprises the same reporter group.

Clause 95. The panel of any one of clauses 91-93, wherein each biosensor comprises a different reporter group.

Clause 96. The panel of clause 92, wherein the array comprises a plurality of sensor elements, each sensor element comprising a biosensor different from or the same as those of the other sensor elements.

Clause 97. The panel of clause 92, wherein the composite sensor comprises a plurality of sensor elements, each sensor element comprising a mixture of different biosensors.

Clause 98. The panel of clause 92, wherein the composite sensor comprises a single sensor element, the single sensor element comprising a mixture of different biosensors.

Clause 99. A method of determining the concentration of glucose, galactose, or a combination thereof, in a sample from a subject, the method comprising applying the sample to the panel of any one of clauses 91-97.

Clause 100. The method of clause 99, wherein the sample is from a subject.

Clause 101. The method according to clause 99 or 100, wherein the sample comprises a biological fluid.

Clause 102. The method according to clause 101, wherein the biological fluid is selected from the group consisting of blood, urine, interstitial fluid, saliva, sweat, tears, gastric lavage, fecal matter, emesis, bile, or combinations thereof.

Clause 103. The method according to clause 100, wherein the sample comprises skin.

Clause 104. A method of detecting the presence of a ligand in a sample, the method comprising a) contacting the biosensor of any one of clauses 1-32 with the sample; b) measuring a signal from the biosensor; and c) comparing the signal to a ligand-free control, wherein a difference in signal indicates the presence of ligand in the sample, and wherein the ligand is selected from the group consisting of glucose, galactose, and a combination thereof.

Clause 105. A method of determining the concentration of a ligand in a sample, the method comprising a) contacting the biosensor of any one of clauses 1-32 with the sample; b) measuring a signal from the biosensor; and c) comparing the signal to a standard hyperbolic ligand binding curve to determine the concentration of ligand in the test sample, wherein the standard hyperbolic ligand binding curve is prepared by measuring the signal transduced by the biosensor when contacted with control samples containing known concentrations of ligand, and wherein the ligand is selected from the group consisting of glucose, galactose, and a combination thereof.

Clause 106. A method of episodically or continuously monitoring the presence of a ligand in a reaction, the method comprising a) contacting the biosensor of any one of clauses 1-32 with the reaction; b) maintaining the reaction under conditions such that the polypeptide is capable of binding ligand present in the reaction; and c) episodically or continuously monitoring the signal from the biosensor in the reaction, wherein the ligand is selected from the group consisting of glucose, galactose, and a combination thereof.

Clause 107. A method of episodically or continuously monitoring the presence of a ligand in a reaction, the method comprising a) contacting the biosensor of any one of clauses 1-32 with the reaction; b) maintaining the reaction under conditions such that the polypeptide is capable of binding ligand present in the reaction; c) episodically or continuously monitoring the signal from the biosensor in the reaction; and d) comparing the signal to a standard hyperbolic ligand binding curve to determine the concentration of ligand in the test sample, wherein the standard hyperbolic ligand binding curve is prepared by measuring the signal transduced by the biosensor when contacted with control samples containing known concentrations of ligand, wherein the ligand is selected from the group consisting of glucose, galactose, and a combination thereof.

Clause 108. The method of any one of clauses 104-107, wherein the biosensor is placed in contact with a subject's skin or mucosal surface.

Clause 109. The method of any one of clauses 104-107, wherein the biosensor is implanted in a subject's body.

Clause 110. The method of any one of clauses 104-107, wherein the biosensor is implanted in a subject's blood vessel, vein, eye, natural or artificial pancreas, alimentary canal, stomach, intestine, esophagus, or skin.

Clause 111. The method of any one of clauses 104-107, wherein the biosensor is configured within or on the surface of a contact lens.

Clause 112. The method of any one of clauses 104-107, wherein the biosensor is configured to be implanted in the skin.

Clause 113. The method of any one of clauses 104-107, wherein the biosensor is implanted in a subject with an optode.

Clause 114. The method of any one of clauses 104-107, wherein the biosensor is implanted in a subject with a microbead.

Clause 115. The method of any one of clauses 104-107, wherein the biosensor generates the signal transdermally.

Clause 116. The method of clause 106, wherein the method further comprises d) comparing the signal to a ligand-free control, wherein a difference in signal indicates the presence of ligand in the reaction.

Clause 117. The method of clause 106, wherein the method further comprises d) comparing the signal to a standard hyperbolic ligand binding curve to determine the concentration of ligand in the test sample, wherein the standard hyperbolic ligand binding curve is prepared by measuring the signal transduced by the biosensor when contacted with control samples containing known concentrations of ligand.

Clause 118. The method of any one of clauses 99, 104-107, and 116-117, wherein the sample comprises a fermentation sample.

Clause 119. The method of any one of clauses 99, 104-107, and 116-117, wherein the sample comprises food or beverage.

Clause 120. The method of clause 119, wherein the sample comprises a beverage selected from soft drink, fountain beverage, water, coffee, tea, milk, dairy-based beverage, soy-based beverage, almond-based beverage, vegetable juice, fruit juice, fruit juice flavored drink, energy drink, sport drink, and alcoholic product, and combinations thereof.

Clause 121. The method of clause 120, wherein the sample comprises water selected from flavored water, mineral water, spring water, sparkling water, and tonic water, and combinations thereof.

Clause 122. The method of clause 120, wherein the sample comprises an alcoholic product selected from beer, malt beverage, liqueur, whiskey, and wine, and combinations thereof.

Clause 123. The method of clause 119, wherein the sample comprises food comprising a semi-solid or liquid form.

Clause 124. The method of clause 119 wherein the sample comprises food selected from yogurt, soup, ice cream, broth, purees, shakes, smoothies, batter, condiments, and sauce, and combinations thereof.

Clause 125. The method of any one of clauses 99, 103-106, and 115-122, wherein the sample is from food engineering.

---

SEQUENCES

SEQ ID NO: 1
GGBP183C polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGHPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EF

| SEQUENCES |
| --- |

SEQ ID NO: 2
GGBP16C polypeptide
MADTRIGVTIYKYDDNCMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGHPDAEARTTYVIKELNDKGIKTEQLQLDTAMW
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EF SEQ ID NO: 3
GGBP183C14A polypeptide
MADTRIGVTIYKYDANFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGHPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EFSKK SEQ ID NO: 4
GGBP183C152N polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGNPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWICTDNKVVRVPYVGVDKDNL
AEFSKK SEQ ID NO: 5
GGBP183C152F polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGFPDAEARTTYVIKELNDKGIKTEQLQLDTAMCD
TAQAKDKMDAWLSGPNANKIEVVIANNDAMAMGAVEALKAHNKSSIPVFGVDALPEALALV
KSGALAGTVLNDANNQAKATFDLAKNLADGKGAADGTNWKIDNKVVRVPYVGVDKDNLAE
FSKK SEQ ID NO: 6
GGBP183C152Q polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRMLDSYDKAYYVGTDSKESGIIQGDLI
AKHWAANQGWDLNKDGQIQFVLLKGEPGQPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EFSKK SEQ ID NO: 7
GGBP183C149Q polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRIZALDSYDKAYYVGTDSKESGIIQGDLI
AKHWAANQGWDLNKDGQIQFVLLKGQPGHPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EFSKK SEQ ID NO: 8
GGBP183C149S polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGSPGHPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EFSKK SEQ ID NO: 9
GGBP183C149K polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGKPGHPDAEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EFSKK SEQ ID NO: 10
GGBP183C155N polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI

| SEQUENCES |
|---|
| AKHWAANQGWDLNKDGQIQFVLLKGEPGHPDNEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EFSKK

SEQ ID NO: 11
GGBP183C155H polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGHPDHEARTTYVIKELNDKGIKTEQLQLDTAMC
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNI9VRVPYVGVDKDNLA
EFSKK SEQ ID NO: 12
A155F + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDFEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 13
A155K + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDKEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 14
A155L + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDLEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 15
A155M + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDMEARTTYVIKELNDKGIKTEQ
LQLDTAMCDTAQAKDKMDAWLSGPNANKIEVVIANNDAMAMGAVEALKAHNKSSIPVF
GVDALPEALALVKSGALAGTVLNDANNQAKATFDLAKNLADGKGAADGTNWKIDNKVV
RVPYVGVDKDNLAEF SEQ ID NO: 16
A155Q + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDQEARTTYVIKELNDKGIKTEQ
LQLDTAMCDTAQAKDKMDAWLSGPNANKIEVVIANNDAMAMGAVEALKAHNKSSIPVF
GVDALPEALALVKSGALAGTVLNDANNQAKATFDLAKNLADGKGAADGTNWKIDNKVV
RVPYVGVDKDNLAEF SEQ ID NO: 17
A155S + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDSEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 18
A155W + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDWEARTTYVIKELNDKGIKTEQ
LQLDTAMCDTAQAKDKMDAWLSGPNANKIEVVIANNDAMAMGAVEALKAHNKSSIPVF
GVDALPEALALVKSGALAGTVLNDANNQAKATFDLAKNLADGKGAADGTNWKIDNKVV
RVPYVGVDKDNLAEF |

| SEQUENCES |
| --- |
| SEQ ID NO: 19<br>A155Y + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDYEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 20<br>D14E + 183C polypeptide<br>MADTRIGVTIYKYDENFMSVVRKAIEQDAKAAPDVQLLMNDSQNDQSKQNDQIDVLLAK<br>GVKALAINLVDPAAAGTVIEKARGQNVPVVFFNKEPSRKALDSYDKAYYVGTDSKESGII<br>QGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 21<br>D14F + 183C polypeptide<br>MADTRIGVTIYKYDFNFMSVVRKAIEQDAKAAPDVQLLMNDSQNDQSKQNDQIDVLLAK<br>GVKALAINLVDPAAAGTVIEKARGQNVPVVFFNKEPSRKALDSYDKAYYVGTDSKESGII<br>QGDLIAKHWAANQGWDLNKDGQIQFVLLKGEPGHPDAEARTTYVIKELNDKGIKTEQL<br>QLDTAMCDTAQAKDKMDAWLSGPNANKJEVVIANNDAMAMGAVEALKAHNKSSIPVF<br>GVDALPEALALVKSGALAGTVLNDANNQAKATFDLAKNLADGKGAADGINWKIDNKVV<br>RVPYVGVDKDNLAEF<br><br>SEQ ID NO: 22<br>D14H + 183C polypeptide<br>MADTRIGVTIYKYDHNFMSVVRIZAIEQDAKAAPDVQLLMNDSQNDQSKQNDQIDVLLA<br>KGVKALAINLVDPAAAGTVIEIZARGQNVPVVFFNKEPSRKALDSYDIZAYYVGTDSKES<br>GIIQGDLIAKHWAANQGWDLNKDGQIQFVLLKGEPGHPDAEARTTYVIKELNDKGIKTE<br>QLQLDTAMCDTAQAKDKMDAWLSGPNANKIEVVIANNDAMAMGAVEALKAHNKSSIPV<br>FGVDALPEALALVKSGALAGTVLNDANNQAKATFDLAKNLADGKGAADGTNWIUDNKV<br>VRVPYVGVDKDNLAEF<br><br>SEQ ID NO: 23<br>D14L + 183C polypeptide<br>MADTRIGVTIYKYDLNFMSVVRKAIEQDAKAAPDVQLLMNDSQNDQSKONDQIDVLLAK<br>GVKALAINLVDPAAAGTVIEKARGQNVPVVFFNKEPSRKALDSYDKAYYVGTDSKESGII<br>QGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 24<br>D14N + 183C polypeptide<br>MADTRIGVTIYKYDNNFMSVVRKAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 25<br>D14Q + 183C polypeptide<br>MADTRIGVTIYKYDQNFMSVVRKAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 26<br>D14S + 183C polypeptide<br>MADTRIGVTIYKYDSNFMSVVRKAIEQDAKAAPDVQLLMNDSQNDQSKQNDQIDVLLAK<br>GVKALAINLVDPAAAGTVIEKARGQNVPVVFFNKEPSRKALDSYDKAYYVGTDSKESGII<br>QGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 27<br>D14T + 183C polypeptide<br>MADTRIGVTIYKYDTNFMSVVRKAIEQDAKAAPDVQLLMNDSQNDQSKQNDQIDVLLAK<br>GVKALAINLVDPAAAGTVIEKARGQNVPVVFFNKEPSRKALDSYDKAYYVGTDSKESGII<br>QGDLIAKHWAANQGWDLNKDGQIQFVLLKGEPGHPDAEARTTYVIKELNDKGIKTEQL |

| SEQUENCES |
| --- |

QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF

SEQ ID NO: 28
D14Y + 183C polypeptide
MADTRIGVTIYKYDYNFMSVVRKAIEQDAKAAPDVQLLMNDSQNDQSKQNDQIDVLLAK
GVKALAINLVDPAAAGTVIEKARGQNVPVVFFNKEPSRKALDSYDKAYYVGTDSKESGII
QGDLIAKHWAANQGWDLNKDGQIQFVLLKGEPGHPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 29
D154A + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPAAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 30
D154N + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPNAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWIGDNKVVR
VPYVGVDKDNLAEF SEQ ID NO: 31
D236A + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANIGEVVIANNDAMAMGAVEALKAHNKSSIPVF
GVAALPEALALVKSGALAGTVLNDANNQAKATFDLAKNLADGKGAADGTNWKIDNKVV
RVPYVGVDKDNLAEF SEQ ID NO: 32
D236N + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANNDAMAMGAVEALKAHNKSSIPVFG
VNALPEALALVKSGALAGTVLNDANNQAKATFDLAKNLADGKGAADGTNWKIDNKVVR
VPYVGVDKDNLAEF SEQ ID NO: 33
E149Q + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGQPGHPDAEARTTYVIKELNDKGIKTEQ
LQLDTAMCDTAQAKDKMDAWLSGPNANKIEVVIANNDAMAMGAVEALKAHNKSSIPVF
GVDALPEALALVKSGALAGTVLNDANNQAKATFDLAKNLADGKGAADGTNWKIDNKVV
RVPYVGVDKDNLAEF SEQ ID NO: 34
F16A + 183C polypeptide
MADTRIGVTIYKYDDNAMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 35
F16L + 183C polypeptide
MADTRIGVTIYKYDDNLMSVVRKAIEQDAKAAPDVQLLMNDSQNDQSKQNDQIDVLLAK
GVKALAINLVDPAAAGTVIEKARGQNVPVVFFNKEPSRKALDSYDKAYYVGTDSKESGII
QGDLIAKHWAANQGWDLNKDGQIQFVLLKGEPGHPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF

| SEQUENCES |
| --- |

SEQ ID NO: 36
H152A + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGAPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 37
H152K + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGIDSKESG
IIQGDLIAKHWAANQGWDLNKDGQIQFVLLKGEPGKPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 38
K92A + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNAEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 39
M182W + 183C polypeptide
MADTRIGVTIYKYDDNFMSVVRIZAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAWCDTAQAKDKMDAWLSGPNANKIEVVIANNDAMAMGAVEALKAHNKSSIPVF
GVDALPEALALVKSGALAGTVLNDANNQAKATFDLAKNLADGKGAADGTNWKIDNKVV
RVPYVGVDKDNLAEF SEQ ID NO: 40
N211A + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANADAMAMGAVEALKAHNKSSIPVFG
VDALPEALALVKSGALAGTVLNDANNQAIZATFDLAKNLADGKGAADGTNWKIDNKVVR
VPYVGVDKDNLAEF SEQ ID NO: 41
N211F + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANFDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 42
N211H + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANHDAMAMGAVEALKAHNKSSIPVFG
VDALPEALALVKSGALAGTVLNDANNQAKATFDLAKNLADGKGAADGINWKIDNKVVR
VPYVGVDKDNLAEF SEQ ID NO: 43
N211K + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANKDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 44
N211M + 183C polypeptide
MADTRIGVTIYKYDDNFMSVVRKAIEQDAIZAAPDVQLLMNDSQNDQSKQNDQIDVLLA
KGVKALAINLVDPAAAGTVIEKARGQNVPVVFFNKEPSRKALDSYDKAYYVGTDSKESG

| SEQUENCES |
| --- |
| IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANMDAMAMGAVEALKAHNKSSIPVF<br>GVDALPEALALVKSGALAGTVLNDANNQAKATFDLAKNLADGKGAADGTNWKIDNKVV<br>RVPYVGVDKDNLAEF<br><br>SEQ ID NO: 45<br>N211Q + 183C polypeptide<br>MADTRIGVTIYKYDDNFMSVVRIZAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANQDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 46<br>N211S + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANSDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 47<br>N211W + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFNKEPSRIZALDSYDIZAYYVGTDSKES<br>GIIQGDLIAKHWAANQGWDLNKDGQIQFVLLKGEPGHPDAEARTTYVIKELNDKGIKTE<br>QLQLDTAMCDTAQAKDKMDAWLSGPNANKIEVVIANWDAMAMGAVEALKAHNKSSIP<br>VFGVDALPEALALVKSGALAGTVLNDANNQAKATFDLAKNLADGKGAADGTNWKIDNK<br>VVRVPYVGVDKDNLAEF<br><br>SEQ ID NO: 48<br>N211Y + 183C polypeptide<br>MADTRIGVTIYKYDDNFMSVVRKAIEQDAKAAPDVQLLMNDSQNDQSKQNDQIDVLLA<br>KGVIZALAINLVDPAAAGTVIEKARGQNVPVVFFNKEPSRKALDSYDKAYYVGTDSKES<br>GIIQGDLIAKHWAANQGWDLNKDGQIQFVLLKGEPGHPDAEARTTYVIKELNDKGIKTE<br>QLQLDTAMCDTAQAKDKMDAWLSGPNANKIEVVIANYDAMAMGAVEALIZAHNKSSIP<br>VFGVDALPEALALVKSGALAGTVLNDANNQAKATFDLAKNLADGKGAADGTNWKIDNK<br>VVRVPYVGVDKDNLAEF<br><br>SEQ ID NO: 49<br>N256A + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFNKEPSRIZALDSYDKAYYVGTDSKES<br>GIIQGDLIAKHWAANQGWDLNKDGQIQFVLLKGEPGHPDAEARTTYVIKELNDKGIKTE<br>QLQLDTAMCDTAQAKDKMDAWLSGPNANKIEVVIANNDAMAMGAVEALKAHNKSSIPV<br>FGVDALPEALALVKSGALAGTVLADANNQAKATFDLAKNLADGKGAADGTNWIGDNKV<br>VRVPYVGVDKDNLAEF<br><br>SEQ ID NO: 50<br>N256D + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLDDANNQAKATFDLAKNLADGKGAADGTNWKIDNKVVR<br>VPYVGVDKDNLAEF<br><br>SEQ ID NO: 51<br>N91A + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFAKEPSRKALDSYDKAYYVGTDSKESG<br>IIQGDLIAKHWAANQGWDLNKDGQIQFVLLKGEPGHPDAEARTTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF<br><br>SEQ ID NO: 52<br>R158A + 183C polypeptide<br>MADTRIGVTIYKYDDNFMSVVRKAIEQDAKAAPDVQLLMNDSQNDQSKQNDQIDVLLA<br>KGVKALAINLVDPAAAGTVIEKARGQNVPVVFFNKEPSRKALDSYDKAYYVGTDSKESG<br>IIQGDLIAKHWAANQGWDLNKDGQIQFVLLKGEPGHPDAEAATTYVIKELNDKGIKTEQL<br>QLDTAMCDTAQAKDKMDAWLSGPNANKIEVVIANNDAMAMGAVEALKAHNKSSIPVFG<br>VDALPEALALVKSGALAGTVLNDANNQAKATFDLAKNLADGKGAADGTNWKIDNKVVR<br>VPYVGVDKDNLAEF |

-continued

SEQUENCES

SEQ ID NO: 53
R158K + 183C polypeptide
MADTRIGVTIYKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEAKTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWIGDNKVVR
VPYVGVDKDNLAEF SEQ ID NO: 54
Y10A + 183C polypeptide
MADTRIGVTIAKYDDNFMSVVRKAIEQDAKAAPDVQLLMNDSQNDQSKQNDQIDVLLA
KGVKALAINLVDPAAAGTVIEKARGQNVPVVFFNKEPSRKALDSYDKAYYVGTDSKESG
IIQGDLIAKHWAANQGWDLNKDGQIQFVLLKGEPGHPDAEARTTYVIKELNDKGIKTEQL
QLDTAMCDTAQAKDKMDAWLSGPNANKIEVVIANNDAMAMGAVEALKAHNKSSIPVFG
VDALPEALALVKSGALAGTVLNDANNQAKATFDLAKNLADGKGAADGTNWKIDNKVVR
VPYVGVDKDNLAEF SEQ ID NO: 55
Wild-type E. coli GGBP polypeptide
MADTRIGVTIYKYDDNFMSVVRKAIEQDAKAAPDVQLLMNDSQNDQSKQNDQIDVLLAKGV
KALAINLVDPAAAGTVIEKARGQNVPVVFFNKEPSRKALDSYDKAYYVGTDSKESGIIQGDLI
AKHWAANQGWDLNKDGQIQFVLLKGEPGHPDAEARTTYVIKELNDKGIKTEQLQLDTAMW
DTAQAKDKMDAWLSGPNANKIEVVIANNDAMAMGAVEALKAHNKSSIPVFGVDALPEALAL
VKSGALAGTVLNDANNQAKATFDLAKNLADGKGAADGTNWKIDNKVVRVPYVGVDKDNLA
EF SEQ ID NO: 56
183C polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GTGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 57
16C polynucleotide
ATGGCAGATACTCGTATTGGTGTAACTATTTATAAATACGATGATAATTG
TATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GGGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 58
14A polynucleotide
ATGGCAGATACTCGTATTGGTGTAACTATTTATAAATACGATGCGAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA

| SEQUENCES |
|---|
| CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 59
152N polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTAACCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 60
152F polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTTTTCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 61
152Q polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCAGCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG |

| SEQUENCES |
|---|
| CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 62
149Q polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCCAG
CCCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 63
149S polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCAGC
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 64
149K polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCAAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 65
155N polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA |

| SEQUENCES |
| --- |
| CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATAACGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 66
155H polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATCATGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 67
155F polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATTTTGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 68
155K polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATAAAGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG |

| SEQUENCES |
| --- |
| CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT<br><br>SEQ ID NO: 69<br>155L polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA<br>CCTGGTTGATCCGGCGGCGGCCGGTACCGTTATTGAAAAAGCCCGTGGCC<br>AGAACGTGCCGGTGGTGTTCTTCAACAAAGAACCGAGCCGCAAAGCGCTG<br>GATAGCTACGATAAAGCGTACTATGTGGGCACCGATAGCAAAGAAAGCGG<br>CATTATTCAGGGCGATCTGATTGCGAAACATTGGGCGGCGAACCAGGGCT<br>GGGATCTGAACAAAGATGGCCAGATTCAGTTCGTGCTGCTGAAAGGCGAA<br>CCGGGTCATCCGGATCTGGAAGCGCGTACCACCTATGTGATCAAAGAACT<br>GAACGACAAAGGCATCAAAACCGAACAGCTGCAACTGGATACCGCGATGT<br>GCGATACCGCGCAGGCGAAAGATAAAATGGATGCGTGGCTGAGCGGTCCG<br>AACGCGAACAAAATTGAAGTGGTGATTGCGAACAACGATGCGATGGCGAT<br>GGGCGCGGTGGAAGCGCTGAAAGCCCATAACAAATCCAGCATTCCGGTGT<br>TTGGCGTGGATGCCCTGCCGGAAGCGCTGGCGCTGGTTAAAAGCGGTGCG<br>CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT<br><br>SEQ ID NO: 70<br>155M polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA<br>CCTGGTTGATCCGGCGGCGGCCGGTACCGTTATTGAAAAAGCCCGTGGCC<br>AGAACGTGCCGGTGGTGTTCTTCAACAAAGAACCGAGCCGCAAAGCGCTG<br>GATAGCTACGATAAAGCGTACTATGTGGGCACCGATAGCAAAGAAAGCGG<br>CATTATTCAGGGCGATCTGATTGCGAAACATTGGGCGGCGAACCAGGGCT<br>GGGATCTGAACAAAGATGGCCAGATTCAGTTCGTGCTGCTGAAAGGCGAA<br>CCGGGTCATCCGGATATGGAAGCGCGTACCACCTATGTGATCAAAGAACT<br>GAACGACAAAGGCATCAAAACCGAACAGCTGCAACTGGATACCGCGATGT<br>GCGATACCGCGCAGGCGAAAGATAAAATGGATGCGTGGCTGAGCGGTCCG<br>AACGCGAACAAAATTGAAGTGGTGATTGCGAACAACGATGCGATGGCGAT<br>GGGCGCGGTGGAAGCGCTGAAAGCCCATAACAAATCCAGCATTCCGGTGT<br>TTGGCGTGGATGCCCTGCCGGAAGCGCTGGCGCTGGTTAAAAGCGGTGCG<br>CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT<br><br>SEQ ID NO: 71<br>155Q polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA<br>CCTGGTTGATCCGGCGGCGGCCGGTACCGTTATTGAAAAAGCCCGTGGCC<br>AGAACGTGCCGGTGGTGTTCTTCAACAAAGAACCGAGCCGCAAAGCGCTG<br>GATAGCTACGATAAAGCGTACTATGTGGGCACCGATAGCAAAGAAAGCGG<br>CATTATTCAGGGCGATCTGATTGCGAAACATTGGGCGGCGAACCAGGGCT<br>GGGATCTGAACAAAGATGGCCAGATTCAGTTCGTGCTGCTGAAAGGCGAA<br>CCGGGTCATCCGGATCAGGAAGCGCGTACCACCTATGTGATCAAAGAACT<br>GAACGACAAAGGCATCAAAACCGAACAGCTGCAACTGGATACCGCGATGT<br>GCGATACCGCGCAGGCGAAAGATAAAATGGATGCGTGGCTGAGCGGTCCG<br>AACGCGAACAAAATTGAAGTGGTGATTGCGAACAACGATGCGATGGCGAT<br>GGGCGCGGTGGAAGCGCTGAAAGCCCATAACAAATCCAGCATTCCGGTGT<br>TTGGCGTGGATGCCCTGCCGGAAGCGCTGGCGCTGGTTAAAAGCGGTGCG<br>CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT<br><br>SEQ ID NO: 72<br>155S polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA |

-continued

| SEQUENCES |
|---|
| CCTGGTTGATCCGGCGGCGGCCGGTACCGTTATTGAAAAAGCCCGTGGCC |
| AGAACGTGCCGGTGGTGTTCTTCAACAAAGAACCGAGCCGCAAAGCGCTG |
| GATAGCTACGATAAAGCGTACTATGTGGGCACCGATAGCAAAGAAAGCGG |
| CATTATTCAGGGCGATCTGATTGCGAAACATTGGGCGGCGAACCAGGGCT |
| GGGATCTGAACAAAGATGGCCAGATTCAGTTCGTGCTGCTGAAAGGCGAA |
| CCGGGTCATCCGGATAGCGAAGCGCGTACCACCTATGTGATCAAAGAACT |
| GAACGACAAAGGCATCAAAACCGAACAGCTGCAACTGGATACCGCGATGT |
| GCGATACCGCGCAGGCGAAAGATAAAATGGATGCGTGGCTGAGCGGTCCG |
| AACGCGAACAAAATTGAAGTGGTGATTGCGAACAACGATGCGATGGCGAT |
| GGGCGCGGTGGAAGCGCTGAAAGCCCATAACAAATCCAGCATTCCGGTGT |
| TTGGCGTGGATGCCCTGCCGGAAGCGCTGGCGCTGGTTAAAAGCGGTGCG |
| CTGGCGGGCACCGTTCTGAACGATGCCAACAACCAGGCGAAAGCCACCTT |
| CGATCTGGCGAAAAACCTGGCGGATGGTAAAGGCGCGGCCGATGGCACCA |
| ACTGGAAAATTGATAACAAAGTGGTGCGTGTGCCGTATGTGGGCGTGGAT |
| AAAGATAACCTGGCCGAATTT |

SEQ ID NO: 73
155W polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATTGGGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 74
155Y polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATTATGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 75
14E polynucleotide
ATGGCAGATACTCGTATTGGTGTAACTATTTATAAATACGATGAAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG

| SEQUENCES |
|---|
| CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 76
14F polynucleotide
ATGGCAGATACTCGTATTGGTGTAACTATTTATAAATACGATTTTAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 77
14H polynucleotide
ATGGCAGATACTCGTATTGGTGTAACTATTTATAAATACGATCATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 78
14L polynucleotide
ATGGCAGATACTCGTATTGGTGTAACTATTTATAAATACGATCTGAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 79
14N polynucleotide
ATGGCAGATACTCGTATTGGTGTAACTATTTATAAATACGATAACAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA |

CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 80
14Q polynucleotide
ATGGCAGATACTCGTATTGGTGTAACTATTTATAAATACGATCAGAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 81
14S polynucleotide
ATGGCAGATACTCGTATTGGTGTAACTATTTATAAATACGATAGCAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 82
14T polynucleotide
ATGGCAGATACTCGTATTGGTGTAACTATTTATAAATACGATACCAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 83
14Y polynucleotide
ATGGCAGATACTCGTATTGGTGTAACTATTTATAAATACGATTATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 84
154A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGCGGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 85
154N polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGAACGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 86
236A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA

| SEQUENCES |
|---|
| CCTGGTTGATCCGGCGGCGGCCGGTACCGTTATTGAAAAAGCCCGTGGCC |
| AGAACGTGCCGGTGGTGTTCTTCAACAAAGAACCGAGCCGCAAAGCGCTG |
| GATAGCTACGATAAAGCGTACTATGTGGGCACCGATAGCAAAGAAAGCGG |
| CATTATTCAGGGCGATCTGATTGCGAAACATTGGGCGGCGAACCAGGGCT |
| GGGATCTGAACAAAGATGGCCAGATTCAGTTCGTGCTGCTGAAAGGCGAA |
| CCGGGTCATCCGGATGCCGAAGCGCGTACCACCTATGTGATCAAAGAACT |
| GAACGACAAAGGCATCAAAACCGAACAGCTGCAACTGGATACCGCGATGT |
| GCGATACCGCGCAGGCGAAAGATAAAATGGATGCGTGGCTGAGCGGTCCG |
| AACGCGAACAAAATTGAAGTGGTGATTGCGAACAACGATGCGATGGCGAT |
| GGGCGCGGTGGAAGCGCTGAAAGCCCATAACAAATCCAGCATTCCGGTGT |
| TTGGCGTGGCGGCCCTGCCGGAAGCGCTGGCGCTGGTTAAAAGCGGTGCG |
| CTGGCGGGCACCGTTCTGAACGATGCCAACAACCAGGCGAAAGCCACCTT |
| CGATCTGGCGAAAAACCTGGCGGATGGTAAAGGCGCGGCCGATGGCACCA |
| ACTGGAAAATTGATAACAAAGTGGTGCGTGTGCCGTATGTGGGCGTGGAT |
| AAAGATAACCTGGCCGAATTT |

SEQ ID NO: 87
236N polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGAACGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 88
149Q polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCCAG
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 89
16A polynucleotide
ATGGCAGATACTCGTATTGGTGTAACTATTTATAAATACGATGATAATGC
GATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG

SEQUENCES

CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 90
16L polynucleotide
ATGGCAGATACTCGTATTGGTGTAACTATTTATAAATACGATGATAATCT
GATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 91
152A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTGCGCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 92
152K polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTAAACCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 93
92A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA CCTGGTTGATCCGGCGGCGGCCGGTACCGTTATTGAAAAAGCCCGTGGCC
AGAACGTGCCGGTGGTGTTCTTCAACGCGGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 94
182W polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGTGGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 95
211A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACGCGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 96
211F polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACTTTGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG

| SEQUENCES |
|---|
| CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT |
| SEQ ID NO: 97<br>211H polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA<br>CCTGGTTGATCCGGCGGCGGCCGGTACCGTTATTGAAAAAGCCCGTGGCC<br>AGAACGTGCCGGTGGTGTTCTTCAACAAAGAACCGAGCCGCAAAGCGCTG<br>GATAGCTACGATAAAGCGTACTATGTGGGCACCGATAGCAAAGAAAGCGG<br>CATTATTCAGGGCGATCTGATTGCGAAACATTGGGCGGCGAACCAGGGCT<br>GGGATCTGAACAAAGATGGCCAGATTCAGTTCGTGCTGCTGAAAGGCGAA<br>CCGGGTCATCCGGATGCCGAAGCGCGTACCACCTATGTGATCAAAGAACT<br>GAACGACAAAGGCATCAAAACCGAACAGCTGCAACTGGATACCGCGATGT<br>GCGATACCGCGCAGGCGAAAGATAAAATGGATGCGTGGCTGAGCGGTCCG<br>AACGCGAACAAAATTGAAGTGGTGATTGCGAACCATGATGCGATGGCGAT<br>GGGCGCGGTGGAAGCGCTGAAAGCCCATAACAAATCCAGCATTCCGGTGT<br>TTGGCGTGGATGCCCTGCCGGAAGCGCTGGCGCTGGTTAAAAGCGGTGCG<br>CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT |
| SEQ ID NO: 98<br>211K polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA<br>CCTGGTTGATCCGGCGGCGGCCGGTACCGTTATTGAAAAAGCCCGTGGCC<br>AGAACGTGCCGGTGGTGTTCTTCAACAAAGAACCGAGCCGCAAAGCGCTG<br>GATAGCTACGATAAAGCGTACTATGTGGGCACCGATAGCAAAGAAAGCGG<br>CATTATTCAGGGCGATCTGATTGCGAAACATTGGGCGGCGAACCAGGGCT<br>GGGATCTGAACAAAGATGGCCAGATTCAGTTCGTGCTGCTGAAAGGCGAA<br>CCGGGTCATCCGGATGCCGAAGCGCGTACCACCTATGTGATCAAAGAACT<br>GAACGACAAAGGCATCAAAACCGAACAGCTGCAACTGGATACCGCGATGT<br>GCGATACCGCGCAGGCGAAAGATAAAATGGATGCGTGGCTGAGCGGTCCG<br>AACGCGAACAAAATTGAAGTGGTGATTGCGAACAAAGATGCGATGGCGAT<br>GGGCGCGGTGGAAGCGCTGAAAGCCCATAACAAATCCAGCATTCCGGTGT<br>TTGGCGTGGATGCCCTGCCGGAAGCGCTGGCGCTGGTTAAAAGCGGTGCG<br>CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT |
| SEQ ID NO: 99<br>211M polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA<br>CCTGGTTGATCCGGCGGCGGCCGGTACCGTTATTGAAAAAGCCCGTGGCC<br>AGAACGTGCCGGTGGTGTTCTTCAACAAAGAACCGAGCCGCAAAGCGCTG<br>GATAGCTACGATAAAGCGTACTATGTGGGCACCGATAGCAAAGAAAGCGG<br>CATTATTCAGGGCGATCTGATTGCGAAACATTGGGCGGCGAACCAGGGCT<br>GGGATCTGAACAAAGATGGCCAGATTCAGTTCGTGCTGCTGAAAGGCGAA<br>CCGGGTCATCCGGATGCCGAAGCGCGTACCACCTATGTGATCAAAGAACT<br>GAACGACAAAGGCATCAAAACCGAACAGCTGCAACTGGATACCGCGATGT<br>GCGATACCGCGCAGGCGAAAGATAAAATGGATGCGTGGCTGAGCGGTCCG<br>AACGCGAACAAAATTGAAGTGGTGATTGCGAACATGGATGCGATGGCGAT<br>GGGCGCGGTGGAAGCGCTGAAAGCCCATAACAAATCCAGCATTCCGGTGT<br>TTGGCGTGGATGCCCTGCCGGAAGCGCTGGCGCTGGTTAAAAGCGGTGCG<br>CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT |
| SEQ ID NO: 100<br>211Q polynucleotide<br>ATGGCAGATACTCGTATTGGTGTAACTATTTATAAATACGATGATAATTT<br>CATGAGCGTAGTACGTAAAGCAATTGAACAAGATGCGAAAGCGGCCCCGG<br>ATGTTCAGCTGCTGATGAACGATAGCCAGAACGATCAGAGCAAACAGAAC<br>GATCAGATTGATGTGCTGCTGGCCAAAGGCGTGAAAGCCCTGGCCATTAA |

| SEQUENCES |
|---|
| CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACCAGGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 101
211S polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAGCGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 102
211W polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACTGGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 103
211Y polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACTATGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG |

| SEQUENCES |
|---|
| CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 104
256A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGGCGGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 105
256D polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGGATGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 106
92A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACGCGGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 107
158A polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA |

CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGGCGACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT

SEQ ID NO: 108
158K polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGAAAACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 109
10A polynucleotide
ATGGCAGATACTCGTATTGGTGTAACTATTGCGAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GCGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG
CTGGCGGGCACCGTTCTGAACGATGCCAACAACCAGGCGAAAGCCACCTT
CGATCTGGCGAAAAACCTGGCGGATGGTAAAGGCGCGGCCGATGGCACCA
ACTGGAAAATTGATAACAAAGTGGTGCGTGTGCCGTATGTGGGCGTGGAT
AAAGATAACCTGGCCGAATTT SEQ ID NO: 110
Wild-type E. coli GGBP polynucleotide
ATGGCAGATACTCGTATTGGTGTAACTATTTATAAATACGATGATAATTT
CATGAGCGTAGTACGTAAAGCAATTGAACAAGATGCGAAAGCGGCCCCGG
ATGTTCAGCTGCTGATGAACGATAGCCAGAACGATCAGAGCAAACAGAAC
GATCAGATTGATGTGCTGCTGGCCAAAGGCGTGAAAGCCCTGGCCATTAA
CCTGGTTGATCCGGCGGCGGCCGGTACCGTTATTGAAAAAGCCCGTGGCC
AGAACGTGCCGGTGGTGTTCTTCAACAAAGAACCGAGCCGCAAAGCGCTG
GATAGCTACGATAAAGCGTACTATGTGGGCACCGATAGCAAAGAAAGCGG
CATTATTCAGGGCGATCTGATTGCGAAACATTGGGCGGCGAACCAGGGCT
GGGATCTGAACAAAGATGGCCAGATTCAGTTCGTGCTGCTGAAAGGCGAA
CCGGGTCATCCGGATGCCGAAGCGCGTACCACCTATGTGATCAAAGAACT
GAACGACAAAGGCATCAAAACCGAACAGCTGCAACTGGATACCGCGATGT
GGGATACCGCGCAGGCGAAAGATAAAATGGATGCGTGGCTGAGCGGTCCG
AACGCGAACAAAATTGAAGTGGTGATTGCGAACAACGATGCGATGGCGAT
GGGCGCGGTGGAAGCGCTGAAAGCCCATAACAAATCCAGCATTCCGGTGT
TTGGCGTGGATGCCCTGCCGGAAGCGCTGGCGCTGGTTAAAAGCGGTGCG

| SEQUENCES |
|---|
| CTGGCGGGCACCGTTCTGAACGATGCCAACAACCAGGCGAAAGCCACCTT<br>CGATCTGGCGAAAAACCTGGCGGATGGTAAAGGCGCGGCCGATGGCACCA<br>ACTGGAAAATTGATAACAAAGTGGTGCGTGTGCCGTATGTGGGCGTGGAT<br>AAAGATAACCTGGCCGAATTT<br><br>SEQ ID NO: 111<br>Histine tag, polypeptide<br>GGSHHHHHH<br><br>SEQ ID NO: 112<br>Wild-type E. coli GGBP polypeptide<br>ADTRIGVTIYKYDDNFMSVVRKAIEQDAKAAPDVQLLMNDSQNDQSKQNDQIDVLLAKGVK<br>ALAINLVDPAAAGTVIEKARGQNVPVVFFNKEPSRKALDSYDKAYYVGTDSKESGIIQGDLIA<br>KHWAANQGWDLNKDGQIQFVLLKGEPGHPDAEARTTYVIKELNDKGIKTEQLQLDTAMWD<br>TAQAKDKMDAWLSGPNANKIEVVIANNDAMAMGAVEALKAHNKSSIPVFGVDALPEALALV<br>KSGALAGTVLNDANNQAKATFDLAKNLADGKGAADGTNWKIDNKVVRVPYVGVDKDNLAE<br>F |

We claim:

1. A biosensor comprising:
a) a polypeptide comprising a ligand binding site, wherein the polypeptide comprises the amino acid sequence corresponding to SEQ ID NO:112 (wild-type *E. coli* glucose-galactose binding protein (GGBP)) with a ligand binding affinity-altering single mutation, wherein the single mutation is F16C at the position corresponding to position 16 of SEQ ID NO: 112, wherein the polypeptide comprises the amino acid sequence of SEQ ID NO: 2; and
b) a single reporter conjugated to the polypeptide at the position corresponding to the position 16 of SEQ ID NO: 112, wherein the single reporter comprises a fluorophore comprising acrylodan or badan, and wherein the single reporter exhibits changes in spectral parameters in response to ligand binding, wherein the ligand-bound biosensor results in a reporter-generated signal that is different from the unbound biosensor, and wherein the ligand is selected from the group consisting of glucose, galactose, and a combination thereof.

2. The biosensor of claim 1, wherein
(a) the signal is a fluorescent signal, wherein the signal comprises an emission intensity of the fluorophore recorded at one or more wavelengths;
(b) the signal is a fluorescent signal, wherein a change in the signal comprises a shift in one or more wavelengths;
(c) the signal is a fluorescent signal, wherein the signal comprises a ratio of emission intensities recorded at two or more wavelengths;
(d) the signal is a fluorescent signal, wherein a change in the signal comprises a shift in two or more wavelengths;
(e) the polypeptide has an affinity ($K_D$) for glucose within the concentration range of glucose in vivo for a human subject;
(f) the polypeptide has an affinity ($K_D$) for galactose within the concentration range of galactose in vivo for a human subject;
(g) the the polypeptide has an affinity ($K_D$) for glucose in the range of about [0.2] 0.1 mM to about 100 mM;
(h) the polypeptide has an affinity ($K_D$) for galactose in the range of about 0.8 mM to about 100 mM;
(i) the biosensor is capable of detecting glucose in the range of about 0.1 mmol/L to about 120 mmol/L;
(j) the biosensor is capable of detecting glucose in the range of about 4 mmol/L to about 33 mmol/L; or
(k) the biosensor is capable of detecting galactose in the range of about 0.2 mM to about 400 mM.

3. The biosensor of claim 1, wherein
(a) the ligand comprises glucose, wherein the polypeptide interacts with a portion of the glucose selected from the group consisting of 1-hydroxyl, 2-hydroxyl, 3-hydroxyl, 4-hydroxyl, 6-hydroxyl, pyranose ring, and combinations thereof; or
(b) the ligand comprises a water molecule.

4. The biosensor of claim 1, wherein the biosensor detects glucose in the hypoglycemic, hyperglycemic, and hyperglycemic-hyperosmotic ranges of a human subject.

5. A polypeptide comprising the amino acid sequence of SEQ ID NO: 2.

6. A panel comprising the biosensor according to claim 1.

7. The panel of claim 6, wherein the panel comprises a composite sensor or an array.

8. The panel of claim 7, wherein
(a) the array is selected from a multichannel array or multiplexed array;
(b) the array comprises a plurality of sensor elements, each sensor element comprising a biosensor different from or the same as those of the other sensor elements;
(c) the composite sensor comprises a plurality of sensor elements, each sensor element comprising a mixture of different biosensors; or
(d) the composite sensor comprises a single sensor element, the single sensor element comprising a mixture of different biosensors.

9. The panel of claim 1, wherein the reporter in the biosensor comprises a fluorophore that has acrylodan.

10. The panel of claim 1, wherein the reporter in the biosensor comprises a fluorophore that has badan.

11. A method of determining the concentration of glucose, galactose, or a combination thereof, in a sample from a subject, the method comprising applying the sample to the panel of claim 6, and measuring said concentration.

12. The method according to claim 11, wherein the sample comprises a biological fluid or skin.

13. The method according to claim 12, wherein the biological fluid comprises blood, urine, interstitial fluid, saliva, sweat, tears, gastric lavage, fecal matter, emesis, bile, or combinations thereof.

14. A method of detecting the presence of a ligand in a sample, the method comprising:
  a) contacting the biosensor of claim 1 with the sample;
  b) measuring a signal from the biosensor; and
  c) comparing the signal of b) to the signal obtained by contacting a ligand-free control with the biosensor of claim 1, wherein a difference in signal indicates the presence of ligand in the sample, and
  wherein the ligand is selected from the group consisting of glucose, galactose, and a combination thereof.

15. A method of determining the concentration of a ligand in a sample, the method comprising:
  a) contacting the biosensor of claim 1 with the sample;
  b) measuring a signal from the biosensor; and
  c) comparing the signal to a standard hyperbolic ligand binding curve to determine the concentration of ligand in the sample, wherein the standard hyperbolic ligand binding curve is prepared by measuring the signal transduced by the biosensor of claim 1 when contacted with control samples containing known concentrations of ligand, and
  wherein the ligand is selected from the group consisting of glucose, galactose, and a combination thereof.

16. A method of episodically or continuously monitoring the presence of a ligand in a reaction, the method comprising:
  a) contacting the biosensor of claim 1 with the reaction;
  b) maintaining the reaction under conditions such that the polypeptide is capable of binding ligand present in the reaction; and
  c) episodically or continuously monitoring the signal from the biosensor in the reaction,
  wherein the ligand is selected from the group consisting of glucose, galactose, and a combination thereof.

17. A method of episodically or continuously monitoring the presence of a ligand in a reaction, the method comprising:
  a) contacting the biosensor of claim 1 with the reaction;
  b) maintaining the reaction under conditions such that the polypeptide is capable of binding ligand present in the reaction;
  c) episodically or continuously monitoring the signal from the biosensor in the reaction; and
  d) comparing the signal to a standard hyperbolic ligand binding curve to determine the concentration of ligand in the reaction, wherein the standard hyperbolic ligand binding curve is prepared by measuring the signal transduced by the biosensor of claim 1 when contacted with control samples containing known concentrations of ligand,
  wherein the ligand is selected from the group consisting of glucose, galactose, and a combination thereof.

18. The method of claim 14, wherein the biosensor is implanted in a subject with an optode, or the biosensor is implanted in a subject with a microbead.

19. The method of claim 16, wherein the method further comprises:
  comparing the signal to the signal obtained by contacting a ligand-free control with the biosensor of claim 1, wherein a difference in signal indicates the presence of ligand in the reaction; or
  comparing the signal to a standard hyperbolic ligand binding curve to determine the concentration of ligand in the reaction, wherein the standard hyperbolic ligand binding curve is prepared by measuring the signal transduced by the biosensor of claim 1 when contacted with control samples containing known concentrations of ligand.

20. A method of determining the concentration of glucose, galactose, or a combination thereof, in a sample that comprises a food, a beverage, or a fermentation product, the method comprising applying the sample to the panel of claim 6, and measuring said concentration.

21. The method of claim 20, wherein the sample comprises a beverage selected from soft drink, fountain beverage, water, coffee, tea, milk, dairy-based beverage, soy-based beverage, almond-based beverage, vegetable juice, fruit juice, fruit juice flavored drink, energy drink, sport drink, alcoholic product, and combinations thereof; wherein the sample comprises food in a semisolid or liquid form; or wherein the sample comprises food selected from yogurt, soup, ice cream, broth, purees, shakes, smoothies, batter, condiments, sauce, and combinations thereof.

22. The method of claim 21, wherein the sample comprises water selected from flavored water, mineral water, spring water, sparkling water, tonic water, and combinations thereof, or wherein the sample comprises an alcoholic product selected from beer, malt beverage, liqueur, whiskey, wine, and combinations thereof.

23. A method of determining the concentration of glucose, galactose, or a combination thereof, in a sample that comprises a food, a beverage, or a fermentation product, the method comprising applying the sample to the biosensor of claim 1, and measuring said concentration.

24. The method of claim 23, wherein the sample comprises a beverage selected from soft drink, fountain beverage, water, coffee, tea, milk, dairy-based beverage, soy-based beverage, almond-based beverage, vegetable juice, fruit juice, fruit juice flavored drink, energy drink, sport drink, alcoholic product, and combinations thereof; wherein the sample comprises food in a semisolid or liquid form; or wherein the sample comprises food selected from yogurt, soup, ice cream, broth, purees, shakes, smoothies, batter, condiments, sauce, and combinations thereof.

25. The method of claim 24, wherein the sample comprises a beverage selected from soft drink, fountain beverage, water, coffee, tea, milk, dairy-based beverage, soy-based beverage, almond-based beverage, vegetable juice, fruit juice, fruit juice flavored drink, energy drink, sport drink, alcoholic product, and combinations thereof; wherein the sample comprises food in a semisolid or liquid form; or wherein the sample comprises food selected from yogurt, soup, ice cream, broth, purees, shakes, smoothies, batter, condiments, sauce, and combinations thereof.

\* \* \* \* \*

SEQUENCE LISTING

<160> NUMBER OF SEQ ID NOS: 112

<210> SEQ ID NO 1
<211> LENGTH: 307
<212> TYPE: PRT
<213> ORGANISM: Artificial Sequence
<220> FEATURE:
<223> OTHER INFORMATION: Synthetic

<400> SEQUENCE: 1

```
Met Ala Asp Thr Arg Ile Gly Val Thr Ile Tyr Lys Tyr Asp Asp Asn
1               5                  10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220
```

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 2
<211> LENGTH: 307
<212> TYPE: PRT
<213> ORGANISM: Artificial Sequence
<220> FEATURE:
<223> OTHER INFORMATION: Synthetic

<400> SEQUENCE: 2

Met Ala Asp Thr Arg Ile Gly Val Thr Ile Tyr Lys Tyr Asp Asp Asn
1               5                   10                  15

Cys Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Trp Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

```
Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
290                 295                 300

Ala Glu Phe
305

<210> SEQ ID NO 3
<211> LENGTH: 307
<212> TYPE: PRT
<213> ORGANISM: Artificial Sequence
<220> FEATURE:
<223> OTHER INFORMATION: Synthetic

<400> SEQUENCE: 3

Met Ala Asp Thr Arg Ile Gly Val Thr Ile Tyr Lys Tyr Asp Ala Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
290                 295                 300

Ala Glu Phe
305
```

<210> SEQ ID NO 4
<211> LENGTH: 307
<212> TYPE: PRT
<213> ORGANISM: Artificial Sequence
<220> FEATURE:
<223> OTHER INFORMATION: Synthetic

<400> SEQUENCE: 4

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly Asn Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 5
<211> LENGTH: 307
<212> TYPE: PRT
<213> ORGANISM: Artificial Sequence
<220> FEATURE:
<223> OTHER INFORMATION: Synthetic

<400> SEQUENCE: 5

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
130                 135                 140

Val Leu Leu Lys Gly Glu Pro Gly Phe Pro Asp Ala Glu Ala Arg Thr
145                 150                 155                 160

Thr Tyr Val Ile Lys Glu Leu Asn Asp Lys Gly Ile Lys Thr Glu Gln
            165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
            210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
            245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 6
<211> LENGTH: 307
<212> TYPE: PRT
<213> ORGANISM: Artificial Sequence
<220> FEATURE:
<223> OTHER INFORMATION: Synthetic

<400> SEQUENCE: 6

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
            35                  40                  45

```
Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Asn Lys Glu Pro Ser
                85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140

Val Leu Leu Lys Gly Glu Pro Gly Gln Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
        210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
        290                 295                 300

Ala Glu Phe
305

<210> SEQ ID NO 7
<211> LENGTH: 307
<212> TYPE: PRT
<213> ORGANISM: Artificial Sequence
<220> FEATURE:
<223> OTHER INFORMATION: Synthetic

<400> SEQUENCE: 7

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Asn Lys Glu Pro Ser
                85                  90                  95
```

```
Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Gln Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 8
<211> LENGTH: 307
<212> TYPE: PRT
<213> ORGANISM: Artificial Sequence
<220> FEATURE:
<223> OTHER INFORMATION: Synthetic

<400> SEQUENCE: 8

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140
```

Val Leu Leu Lys Gly Ser Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 9
<211> LENGTH: 307
<212> TYPE: PRT
<213> ORGANISM: Artificial Sequence
<220> FEATURE:
<223> OTHER INFORMATION: Synthetic

<400> SEQUENCE: 9

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Lys Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

```
Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 10
<211> LENGTH: 307
<212> TYPE: PRT
<213> ORGANISM: Artificial Sequence
<220> FEATURE:
<223> OTHER INFORMATION: Synthetic

<400> SEQUENCE: 10

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Asn Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240
```

Glu Ala Leu Ala Leu Val Lys Ser Gly Ala Leu Ala Gly Thr Val Leu
            245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 11
<211> LENGTH: 307
<212> TYPE: PRT
<213> ORGANISM: Artificial Sequence
<220> FEATURE:
<223> OTHER INFORMATION: Synthetic

<400> SEQUENCE: 11

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp His Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
        210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 12
<211> LENGTH: 307
<212> TYPE: PRT
<213> ORGANISM: Artificial Sequence
<220> FEATURE:
<223> OTHER INFORMATION: Synthetic

<400> SEQUENCE: 12

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Phe Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 13

<211> LENGTH: 307
<212> TYPE: PRT
<213> ORGANISM: Artificial Sequence
<220> FEATURE:
<223> OTHER INFORMATION: Synthetic

<400> SEQUENCE: 13

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Lys Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 14
<211> LENGTH: 307
<212> TYPE: PRT
<213> ORGANISM: Artificial Sequence
<220> FEATURE:
<223> OTHER INFORMATION: Synthetic

<400> SEQUENCE: 14

```
Met Ala Asp Thr Arg Ile Gly Val Thr Ile Tyr Lys Tyr Asp Asp Asn
```

```
1               5                   10                  15
Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
                35                  40                  45

Gln Asn Asp Gln Ile Asp Val Leu Leu Ala Lys Gly Val Lys Ala Leu
             50                  55                  60

Ala Ile Asn Leu Val Asp Pro Ala Ala Gly Thr Val Ile Glu Lys
 65                  70                  75                  80

Ala Arg Gly Gln Asn Val Pro Val Val Phe Phe Asn Lys Glu Pro Ser
                    85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
                115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Leu Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
                195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
                275                 280                 285

Asn Lys Val Val Arg Val Pro Tyr Val Gly Val Asp Lys Asp Asn Leu
                290                 295                 300

Ala Glu Phe
305
```

<210> SEQ ID NO 15
<211> LENGTH: 307
<212> TYPE: PRT
<213> ORGANISM: Artificial Sequence
<220> FEATURE:
<223> OTHER INFORMATION: Synthetic

<400> SEQUENCE: 15

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
                35                  40                  45

Gln Asn Asp Gln Ile Asp Val Leu Leu Ala Lys Gly Val Lys Ala Leu
```

```
                 50                  55                  60
Ala Ile Asn Leu Val Asp Pro Ala Ala Gly Thr Val Ile Glu Lys
 65                  70                  75                  80

Ala Arg Gly Gln Asn Val Pro Val Val Phe Phe Asn Lys Glu Pro Ser
                     85                  90                  95

Arg Lys Ala Leu Asp Ser Tyr Asp Lys Ala Tyr Tyr Val Gly Thr Asp
                    100                 105                 110

Ser Lys Glu Ser Gly Ile Ile Gln Gly Asp Leu Ile Ala Lys His Trp
                115                 120                 125

Ala Ala Asn Gln Gly Trp Asp Leu Asn Lys Asp Gly Gln Ile Gln Phe
                130                 135                 140

Val Leu Leu Lys Gly Glu Pro Gly His Pro Asp Met Glu Ala Arg Thr
145                 150                 155                 160

Thr Tyr Val Ile Lys Glu Leu Asn Asp Lys Gly Ile Lys Thr Glu Gln
                    165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
                195                 200                 205

Ile Ala Asn Asn Asp Ala Met Ala Met Gly Ala Val Glu Ala Leu Lys
                210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                    245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
                275                 280                 285

Asn Lys Val Val Arg Val Pro Tyr Val Gly Val Asp Lys Asp Asn Leu
                290                 295                 300

Ala Glu Phe
305

<210> SEQ ID NO 16
<211> LENGTH: 307
<212> TYPE: PRT
<213> ORGANISM: Artificial Sequence
<220> FEATURE:
<223> OTHER INFORMATION: Synthetic

<400> SEQUENCE: 16

Met Ala Asp Thr Arg Ile Gly Val Thr Ile Tyr Lys Tyr Asp Asp Asn
  1               5                  10                  15

Phe Met Ser Val Val Arg Lys Ala Ile Glu Gln Asp Ala Lys Ala Ala
                 20                  25                  30

Pro Asp Val Gln Leu Leu Met Asn Asp Ser Gln Asn Asp Gln Ser Lys
                 35                  40                  45

Gln Asn Asp Gln Ile Asp Val Leu Leu Ala Lys Gly Val Lys Ala Leu
             50                  55                  60

Ala Ile Asn Leu Val Asp Pro Ala Ala Gly Thr Val Ile Glu Lys
 65                  70                  75                  80

Ala Arg Gly Gln Asn Val Pro Val Val Phe Phe Asn Lys Glu Pro Ser
                     85                  90                  95

Arg Lys Ala Leu Asp Ser Tyr Asp Lys Ala Tyr Tyr Val Gly Thr Asp
```

```
            100                 105                 110
Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp Gln Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
        210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
        290                 295                 300

Ala Glu Phe
305

<210> SEQ ID NO 17
<211> LENGTH: 307
<212> TYPE: PRT
<213> ORGANISM: Artificial Sequence
<220> FEATURE:
<223> OTHER INFORMATION: Synthetic

<400> SEQUENCE: 17

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp Ser Glu Ala Arg Thr
```

```
145                 150                 155                 160
Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
                195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
                275                 280                 285

Asn Lys Val Val Arg Val Pro Tyr Val Gly Val Asp Lys Asp Asn Leu
290                 295                 300

Ala Glu Phe
305

<210> SEQ ID NO 18
<211> LENGTH: 307
<212> TYPE: PRT
<213> ORGANISM: Artificial Sequence
<220> FEATURE:
<223> OTHER INFORMATION: Synthetic

<400> SEQUENCE: 18

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
                35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp Trp Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
```

195                 200                 205
Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
                275                 280                 285

Asn Lys Val Val Arg Val Pro Tyr Val Gly Val Asp Lys Asp Asn Leu
290                 295                 300

Ala Glu Phe
305

<210> SEQ ID NO 19
<211> LENGTH: 307
<212> TYPE: PRT
<213> ORGANISM: Artificial Sequence
<220> FEATURE:
<223> OTHER INFORMATION: Synthetic

<400> SEQUENCE: 19

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp Tyr Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu

```
                    245                 250                 255
Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
290                 295                 300

Ala Glu Phe
305

<210> SEQ ID NO 20
<211> LENGTH: 307
<212> TYPE: PRT
<213> ORGANISM: Artificial Sequence
<220> FEATURE:
<223> OTHER INFORMATION: Synthetic

<400> SEQUENCE: 20

Met Ala Asp Thr Arg Ile Gly Val Thr Ile Tyr Lys Tyr Asp Glu Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
```

```
                290                 295                 300

Ala Glu Phe
305

<210> SEQ ID NO 21
<211> LENGTH: 307
<212> TYPE: PRT
<213> ORGANISM: Artificial Sequence
<220> FEATURE:
<223> OTHER INFORMATION: Synthetic

<400> SEQUENCE: 21

Met Ala Asp Thr Arg Ile Gly Val Thr Ile Tyr Lys Tyr Asp Phe Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 22
<211> LENGTH: 307
<212> TYPE: PRT
```

<213> ORGANISM: Artificial Sequence
<220> FEATURE:
<223> OTHER INFORMATION: Synthetic

<400> SEQUENCE: 22

Met Ala Asp Thr Arg Ile Gly Val Thr Ile Tyr Lys Tyr Asp His Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 23
<211> LENGTH: 307
<212> TYPE: PRT
<213> ORGANISM: Artificial Sequence
<220> FEATURE:
<223> OTHER INFORMATION: Synthetic

<400> SEQUENCE: 23

Met Ala Asp Thr Arg Ile Gly Val Thr Ile Tyr Lys Tyr Asp Leu Asn
1               5                   10                  15

```
Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 24
<211> LENGTH: 307
<212> TYPE: PRT
<213> ORGANISM: Artificial Sequence
<220> FEATURE:
<223> OTHER INFORMATION: Synthetic

<400> SEQUENCE: 24

```
Met Ala Asp Thr Arg Ile Gly Val Thr Ile Tyr Lys Tyr Asp Asn Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60
```

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 25
<211> LENGTH: 307
<212> TYPE: PRT
<213> ORGANISM: Artificial Sequence
<220> FEATURE:
<223> OTHER INFORMATION: Synthetic

<400> SEQUENCE: 25

Met Ala Asp Thr Arg Ile Gly Val Thr Ile Tyr Lys Tyr Asp Gln Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

```
Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
            210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 26
<211> LENGTH: 307
<212> TYPE: PRT
<213> ORGANISM: Artificial Sequence
<220> FEATURE:
<223> OTHER INFORMATION: Synthetic

<400> SEQUENCE: 26

Met Ala Asp Thr Arg Ile Gly Val Thr Ile Tyr Lys Tyr Asp Ser Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160
```

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 27
<211> LENGTH: 307
<212> TYPE: PRT
<213> ORGANISM: Artificial Sequence
<220> FEATURE:
<223> OTHER INFORMATION: Synthetic

<400> SEQUENCE: 27

Met Ala Asp Thr Arg Ile Gly Val Thr Ile Tyr Lys Tyr Asp Thr Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
            245                 250                 255

Asn Asp Ala Asn Asn Gln Ala Lys Ala Thr Phe Asp Leu Ala Lys Asn
        260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
290                 295                 300

Ala Glu Phe
305

<210> SEQ ID NO 28
<211> LENGTH: 307
<212> TYPE: PRT
<213> ORGANISM: Artificial Sequence
<220> FEATURE:
<223> OTHER INFORMATION: Synthetic

<400> SEQUENCE: 28

Met Ala Asp Thr Arg Ile Gly Val Thr Ile Tyr Lys Tyr Asp Tyr Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

```
Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 29
<211> LENGTH: 307
<212> TYPE: PRT
<213> ORGANISM: Artificial Sequence
<220> FEATURE:
<223> OTHER INFORMATION: Synthetic

<400> SEQUENCE: 29

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Ala Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300
```

-continued

Ala Glu Phe
305

<210> SEQ ID NO 30
<211> LENGTH: 307
<212> TYPE: PRT
<213> ORGANISM: Artificial Sequence
<220> FEATURE:
<223> OTHER INFORMATION: Synthetic

<400> SEQUENCE: 30

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asn Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 31
<211> LENGTH: 307
<212> TYPE: PRT
<213> ORGANISM: Artificial Sequence
<220> FEATURE:

<223> OTHER INFORMATION: Synthetic

<400> SEQUENCE: 31

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Ala Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 32
<211> LENGTH: 307
<212> TYPE: PRT
<213> ORGANISM: Artificial Sequence
<220> FEATURE:
<223> OTHER INFORMATION: Synthetic

<400> SEQUENCE: 32

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30
```

Pro Asp Val Gln Leu Leu Met Asn Asp Ser Gln Asn Asp Gln Ser Lys
           35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
               100                 105                 110

Ser Lys Glu Ser Gly Ile Ile Gln Gly Asp Leu Ile Ala Lys His Trp
               115                 120                 125

Ala Ala Asn Gln Gly Trp Asp Leu Asn Lys Asp Gly Gln Ile Gln Phe
           130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
           180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asn Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
           260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 33
<211> LENGTH: 307
<212> TYPE: PRT
<213> ORGANISM: Artificial Sequence
<220> FEATURE:
<223> OTHER INFORMATION: Synthetic

<400> SEQUENCE: 33

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
           35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Phe Phe Asn Lys Glu Pro Ser
            85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
130                 135                 140

Val Leu Leu Lys Gly Gln Pro Gly His Pro Asp Ala Glu Ala Arg Thr
145                 150                 155                 160

Thr Tyr Val Ile Lys Glu Leu Asn Asp Lys Gly Ile Lys Thr Glu Gln
            165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
            210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
            245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 34
<211> LENGTH: 307
<212> TYPE: PRT
<213> ORGANISM: Artificial Sequence
<220> FEATURE:
<223> OTHER INFORMATION: Synthetic

<400> SEQUENCE: 34

Met Ala Asp Thr Arg Ile Gly Val Thr Ile Tyr Lys Tyr Asp Asp Asn
1               5                   10                  15

Ala Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
            50                  55                  60

Ala Ile Asn Leu Val Asp Pro Ala Ala Gly Thr Val Ile Glu Lys
65                  70                  75                  80

Ala Arg Gly Gln Asn Val Pro Val Phe Phe Asn Lys Glu Pro Ser
            85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

```
Ala Ala Asn Gln Gly Trp Asp Leu Asn Lys Asp Gly Gln Ile Gln Phe
            130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 35
<211> LENGTH: 307
<212> TYPE: PRT
<213> ORGANISM: Artificial Sequence
<220> FEATURE:
<223> OTHER INFORMATION: Synthetic

<400> SEQUENCE: 35

Met Ala Asp Thr Arg Ile Gly Val Thr Ile Tyr Lys Tyr Asp Asp Asn
1               5                   10                  15

Leu Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175
```

```
Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 36
<211> LENGTH: 307
<212> TYPE: PRT
<213> ORGANISM: Artificial Sequence
<220> FEATURE:
<223> OTHER INFORMATION: Synthetic

<400> SEQUENCE: 36

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly Ala Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220
```

```
Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
        290                 295                 300

Ala Glu Phe
305

<210> SEQ ID NO 37
<211> LENGTH: 307
<212> TYPE: PRT
<213> ORGANISM: Artificial Sequence
<220> FEATURE:
<223> OTHER INFORMATION: Synthetic

<400> SEQUENCE: 37

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly Lys Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270
```

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 38
<211> LENGTH: 307
<212> TYPE: PRT
<213> ORGANISM: Artificial Sequence
<220> FEATURE:
<223> OTHER INFORMATION: Synthetic

<400> SEQUENCE: 38

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Ala Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 39
<211> LENGTH: 307
<212> TYPE: PRT
<213> ORGANISM: Artificial Sequence
<220> FEATURE:
<223> OTHER INFORMATION: Synthetic

<400> SEQUENCE: 39

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Trp Cys Asp Thr Ala Gln Ala Lys Asp Lys
            180                 185                 190

Met Asp Ala Trp Leu Ser Gly Pro Asn Ala Asn Lys Ile Glu Val Val
    195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 40
<211> LENGTH: 307
<212> TYPE: PRT
<213> ORGANISM: Artificial Sequence
<220> FEATURE:
<223> OTHER INFORMATION: Synthetic

<400> SEQUENCE: 40

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Ala Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

<210> SEQ ID NO 41
<211> LENGTH: 307
<212> TYPE: PRT
<213> ORGANISM: Artificial Sequence
<220> FEATURE:
<223> OTHER INFORMATION: Synthetic

<400> SEQUENCE: 41

```
Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
```

```
            35                  40                  45
Gln Asn Asp Gln Ile Asp Val Leu Leu Ala Lys Gly Val Lys Ala Leu
    50                  55                  60
Ala Ile Asn Leu Val Asp Pro Ala Ala Ala Gly Thr Val Ile Glu Lys
65                  70                  75                  80
Ala Arg Gly Gln Asn Val Pro Val Val Phe Phe Asn Lys Glu Pro Ser
                85                  90                  95
Arg Lys Ala Leu Asp Ser Tyr Asp Lys Ala Tyr Tyr Val Gly Thr Asp
            100                 105                 110
Ser Lys Glu Ser Gly Ile Ile Gln Gly Asp Leu Ile Ala Lys His Trp
        115                 120                 125
Ala Ala Asn Gln Gly Trp Asp Leu Asn Lys Asp Gly Gln Ile Gln Phe
    130                 135                 140
Val Leu Leu Lys Gly Glu Pro Gly His Pro Asp Ala Glu Ala Arg Thr
145                 150                 155                 160
Thr Tyr Val Ile Lys Glu Leu Asn Asp Lys Gly Ile Lys Thr Glu Gln
                165                 170                 175
Leu Gln Leu Asp Thr Ala Met Cys Asp Thr Ala Gln Ala Lys Asp Lys
            180                 185                 190
Met Asp Ala Trp Leu Ser Gly Pro Asn Ala Asn Lys Ile Glu Val Val
        195                 200                 205
Ile Ala Asn Phe Asp Ala Met Ala Met Gly Ala Val Glu Ala Leu Lys
    210                 215                 220
Ala His Asn Lys Ser Ser Ile Pro Val Phe Gly Val Asp Ala Leu Pro
225                 230                 235                 240
Glu Ala Leu Ala Leu Val Lys Ser Gly Ala Leu Ala Gly Thr Val Leu
                245                 250                 255
Asn Asp Ala Asn Asn Gln Ala Lys Ala Thr Phe Asp Leu Ala Lys Asn
            260                 265                 270
Leu Ala Asp Gly Lys Gly Ala Ala Asp Gly Thr Asn Trp Lys Ile Asp
        275                 280                 285
Asn Lys Val Val Arg Val Pro Tyr Val Gly Val Asp Lys Asp Asn Leu
    290                 295                 300
Ala Glu Phe
305

<210> SEQ ID NO 42
<211> LENGTH: 307
<212> TYPE: PRT
<213> ORGANISM: Artificial Sequence
<220> FEATURE:
<223> OTHER INFORMATION: Synthetic

<400> SEQUENCE: 42

Met Ala Asp Thr Arg Ile Gly Val Thr Ile Tyr Lys Tyr Asp Asp Asn
1               5                   10                  15
Phe Met Ser Val Val Arg Lys Ala Ile Glu Gln Asp Ala Lys Ala Ala
            20                  25                  30
Pro Asp Val Gln Leu Leu Met Asn Asp Ser Gln Asn Asp Gln Ser Lys
        35                  40                  45
Gln Asn Asp Gln Ile Asp Val Leu Leu Ala Lys Gly Val Lys Ala Leu
    50                  55                  60
Ala Ile Asn Leu Val Asp Pro Ala Ala Ala Gly Thr Val Ile Glu Lys
65                  70                  75                  80
Ala Arg Gly Gln Asn Val Pro Val Val Phe Phe Asn Lys Glu Pro Ser
```

```
                85                  90                  95
Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn His Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 43
<211> LENGTH: 307
<212> TYPE: PRT
<213> ORGANISM: Artificial Sequence
<220> FEATURE:
<223> OTHER INFORMATION: Synthetic

<400> SEQUENCE: 43

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
```

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Lys Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 44
<211> LENGTH: 307
<212> TYPE: PRT
<213> ORGANISM: Artificial Sequence
<220> FEATURE:
<223> OTHER INFORMATION: Synthetic

<400> SEQUENCE: 44

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys

```
            180                 185                 190
Met Asp Ala Trp Leu Ser Gly Pro Asn Ala Asn Lys Ile Glu Val Val
            195                 200                 205

Ile Ala Asn Met Asp Ala Met Ala Met Gly Ala Val Glu Ala Leu Lys
            210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 45
<211> LENGTH: 307
<212> TYPE: PRT
<213> ORGANISM: Artificial Sequence
<220> FEATURE:
<223> OTHER INFORMATION: Synthetic

<400> SEQUENCE: 45

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
            85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
            165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
            195                 200                 205

Ile Ala Asn Gln Asp Ala Met Ala Met Gly Ala Val Glu Ala Leu Lys
            210                 215                 220

Ala His Asn Lys Ser Ser Ile Pro Val Phe Gly Val Asp Ala Leu Pro
```

```
                225                 230                 235                 240
Glu Ala Leu Ala Leu Val Lys Ser Gly Ala Leu Ala Gly Thr Val Leu
                        245                 250                 255

Asn Asp Ala Asn Asn Gln Ala Lys Ala Thr Phe Asp Leu Ala Lys Asn
                        260                 265                 270

Leu Ala Asp Gly Lys Gly Ala Ala Asp Gly Thr Asn Trp Lys Ile Asp
                        275                 280                 285

Asn Lys Val Val Arg Val Pro Tyr Val Gly Val Asp Lys Asp Asn Leu
                        290                 295                 300

Ala Glu Phe
305

<210> SEQ ID NO 46
<211> LENGTH: 307
<212> TYPE: PRT
<213> ORGANISM: Artificial Sequence
<220> FEATURE:
<223> OTHER INFORMATION: Synthetic

<400> SEQUENCE: 46

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
                35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
                115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
                195                 200                 205

Ile Ala Asn Ser Asp Ala Met Ala Met Gly Ala Val Glu Ala Leu Lys
        210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                        245                 250                 255

Asn Asp Ala Asn Asn Gln Ala Lys Ala Thr Phe Asp Leu Ala Lys Asn
                        260                 265                 270

Leu Ala Asp Gly Lys Gly Ala Ala Asp Gly Thr Asn Trp Lys Ile Asp
```

```
                275                 280                 285
Asn Lys Val Val Arg Val Pro Tyr Val Gly Val Asp Lys Asp Asn Leu
            290                 295                 300

Ala Glu Phe
305

<210> SEQ ID NO 47
<211> LENGTH: 307
<212> TYPE: PRT
<213> ORGANISM: Artificial Sequence
<220> FEATURE:
<223> OTHER INFORMATION: Synthetic

<400> SEQUENCE: 47

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Trp Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305
```

```
<210> SEQ ID NO 48
<211> LENGTH: 307
<212> TYPE: PRT
<213> ORGANISM: Artificial Sequence
<220> FEATURE:
<223> OTHER INFORMATION: Synthetic

<400> SEQUENCE: 48

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Gly Thr Val Ile Glu Lys
65                  70                  75                  80

Ala Arg Gly Gln Asn Val Pro Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Tyr Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
    290                 295                 300

Ala Glu Phe
305

<210> SEQ ID NO 49
<211> LENGTH: 307
<212> TYPE: PRT
<213> ORGANISM: Artificial Sequence
<220> FEATURE:
<223> OTHER INFORMATION: Synthetic

<400> SEQUENCE: 49
```

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
            130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
            210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Ala Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
            290                 295                 300

Ala Glu Phe
305

<210> SEQ ID NO 50
<211> LENGTH: 307
<212> TYPE: PRT
<213> ORGANISM: Artificial Sequence
<220> FEATURE:
<223> OTHER INFORMATION: Synthetic

<400> SEQUENCE: 50

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
 50                  55                  60

Ala Ile Asn Leu Val Asp Pro Ala Ala Gly Thr Val Ile Glu Lys
 65                  70                  75                  80

Ala Arg Gly Gln Asn Val Pro Val Val Phe Phe Asn Lys Glu Pro Ser
                 85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
                180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asp Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
        290                 295                 300

Ala Glu Phe
305

<210> SEQ ID NO 51
<211> LENGTH: 307
<212> TYPE: PRT
<213> ORGANISM: Artificial Sequence
<220> FEATURE:
<223> OTHER INFORMATION: Synthetic

<400> SEQUENCE: 51

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
 50                  55                  60

Ala Ile Asn Leu Val Asp Pro Ala Ala Gly Thr Val Ile Glu Lys
 65                  70                  75                  80

Ala Arg Gly Gln Asn Val Pro Val Val Phe Phe Ala Lys Glu Pro Ser
                 85                  90                  95

```
Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
        275                 280                 285

Asn Lys Val Val Arg Val Pro Tyr Val Gly Val Asp Lys Asp Asn Leu
290                 295                 300

Ala Glu Phe
305

<210> SEQ ID NO 52
<211> LENGTH: 307
<212> TYPE: PRT
<213> ORGANISM: Artificial Sequence
<220> FEATURE:
<223> OTHER INFORMATION: Synthetic

<400> SEQUENCE: 52

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
        35                  40                  45

Gln Asn Asp Gln Ile Asp Val Leu Leu Ala Lys Gly Val Lys Ala Leu
    50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
                100                 105                 110

Ser Lys Glu Ser Gly Ile Ile Gln Gly Asp Leu Ile Ala Lys His Trp
            115                 120                 125

Ala Ala Asn Gln Gly Trp Asp Leu Asn Lys Asp Gly Gln Ile Gln Phe
        130                 135                 140
```

```
Val Leu Leu Lys Gly Glu Pro Gly His Pro Asp Ala Glu Ala Ala Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
290                 295                 300

Ala Glu Phe
305

<210> SEQ ID NO 53
<211> LENGTH: 307
<212> TYPE: PRT
<213> ORGANISM: Artificial Sequence
<220> FEATURE:
<223> OTHER INFORMATION: Synthetic

<400> SEQUENCE: 53

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Lys Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190
```

```
Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
                260                 265                 270

Leu Ala Asp Gly Lys Gly Ala Ala Asp Gly Thr Asn Trp Lys Ile Asp
                275                 280                 285

Asn Lys Val Val Arg Val Pro Tyr Val Gly Val Asp Lys Asp Asn Leu
290                 295                 300

Ala Glu Phe
305

<210> SEQ ID NO 54
<211> LENGTH: 307
<212> TYPE: PRT
<213> ORGANISM: Artificial Sequence
<220> FEATURE:
<223> OTHER INFORMATION: Synthetic

<400> SEQUENCE: 54

Met Ala Asp Thr Arg Ile Gly Val Thr Ile Ala Lys Tyr Asp Asp Asn
1               5                   10                  15

Phe Met Ser Val Val Arg Lys Ala Ile Glu Gln Asp Ala Lys Ala Ala
                20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Cys Asp Thr Ala Gln Ala Lys Asp Lys
            180                 185                 190

Met Asp Ala Trp Leu Ser Gly Pro Asn Ala Asn Lys Ile Glu Val Val
            195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240
```

```
Glu Ala Leu Ala Leu Val Lys Ser Gly Ala Leu Ala Gly Thr Val Leu
            245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285

Asn Lys Val Val Arg Val Pro Tyr Val Gly Val Asp Lys Asp Asn Leu
            290                 295                 300

Ala Glu Phe
305

<210> SEQ ID NO 55
<211> LENGTH: 307
<212> TYPE: PRT
<213> ORGANISM: Artificial Sequence
<220> FEATURE:
<223> OTHER INFORMATION: Synthetic

<400> SEQUENCE: 55

Met Ala Asp Thr Arg Ile Gly Val Thr Ile Tyr Lys Tyr Asp Asp Asn
1               5                   10                  15

Phe Met Ser Val Val Arg Lys Ala Ile Glu Gln Asp Ala Lys Ala Ala
            20                  25                  30

Pro Asp Val Gln Leu Leu Met Asn Asp Ser Gln Asn Asp Gln Ser Lys
            35                  40                  45

Gln Asn Asp Gln Ile Asp Val Leu Leu Ala Lys Gly Val Lys Ala Leu
        50                  55                  60

Ala Ile Asn Leu Val Asp Pro Ala Ala Gly Thr Val Ile Glu Lys
65                  70                  75                  80

Ala Arg Gly Gln Asn Val Pro Val Val Phe Phe Asn Lys Glu Pro Ser
                85                  90                  95

Arg Lys Ala Leu Asp Ser Tyr Asp Lys Ala Tyr Tyr Val Gly Thr Asp
            100                 105                 110

Ser Lys Glu Ser Gly Ile Ile Gln Gly Asp Leu Ile Ala Lys His Trp
        115                 120                 125

Ala Ala Asn Gln Gly Trp Asp Leu Asn Lys Asp Gly Gln Ile Gln Phe
    130                 135                 140

Val Leu Leu Lys Gly Glu Pro Gly His Pro Asp Ala Glu Ala Arg Thr
145                 150                 155                 160

Thr Tyr Val Ile Lys Glu Leu Asn Asp Lys Gly Ile Lys Thr Glu Gln
                165                 170                 175

Leu Gln Leu Asp Thr Ala Met Trp Asp Thr Ala Gln Ala Lys Asp Lys
            180                 185                 190

Met Asp Ala Trp Leu Ser Gly Pro Asn Ala Asn Lys Ile Glu Val Val
        195                 200                 205

Ile Ala Asn Asn Asp Ala Met Ala Met Gly Ala Val Glu Ala Leu Lys
    210                 215                 220

Ala His Asn Lys Ser Ser Ile Pro Val Phe Gly Val Asp Ala Leu Pro
225                 230                 235                 240

Glu Ala Leu Ala Leu Val Lys Ser Gly Ala Leu Ala Gly Thr Val Leu
                245                 250                 255

Asn Asp Ala Asn Asn Gln Ala Lys Ala Thr Phe Asp Leu Ala Lys Asn
            260                 265                 270

Leu Ala Asp Gly Lys Gly Ala Ala Asp Gly Thr Asn Trp Lys Ile Asp
            275                 280                 285
```

```
Asn Lys Val Val Arg Val Pro Tyr Val Gly Val Asp Lys Asp Asn Leu
    290                 295                 300

Ala Glu Phe
305
```

<210> SEQ ID NO 56
<211> LENGTH: 921
<212> TYPE: DNA
<213> ORGANISM: Artificial Sequence
<220> FEATURE:
<223> OTHER INFORMATION: Synthetic

<400> SEQUENCE: 56

| | | | | | |
|---|---|---|---|---|---|
| atggcagata | ctcgtattgg | tgtaactatt | tataaatacg | atgataattt | catgagcgta | 60 |
| gtacgtaaag | caattgaaca | agatgcgaaa | gcggccccgg | atgttcagct | gctgatgaac | 120 |
| gatagccaga | acgatcagag | caaacagaac | gatcagattg | atgtgctgct | ggccaaaggc | 180 |
| gtgaaagccc | tggccattaa | cctggttgat | ccggcggcgg | ccggtaccgt | tattgaaaaa | 240 |
| gcccgtggcc | agaacgtgcc | ggtggtgttc | ttcaacaaag | aaccgagccg | caaagcgctg | 300 |
| gatagctacg | ataaagcgta | ctatgtgggc | accgatagca | agaaagcgg | cattattcag | 360 |
| ggcgatctga | ttgcgaaaca | ttgggcggcg | aaccagggct | gggatctgaa | caaagatggc | 420 |
| cagattcagt | tcgtgctgct | gaaaggcgaa | ccgggtcatc | cggatgccga | agcgcgtacc | 480 |
| acctatgtga | tcaaagaact | gaacgacaaa | ggcatcaaaa | ccgaacagct | gcaactggat | 540 |
| accgcgatgt | gtgataccgc | gcaggcgaaa | gataaaatgg | atgcgtggct | gagcggtccg | 600 |
| aacgcgaaca | aaattgaagt | ggtgattgcg | aacaacgatg | cgatggcgat | gggcgcggtg | 660 |
| gaagcgctga | agcccataa | caaatccagc | attccggtgt | ttggcgtgga | tgccctgccg | 720 |
| gaagcgctgg | cgctggttaa | agcggtgcg | ctggcgggca | ccgttctgaa | cgatgccaac | 780 |
| aaccaggcga | agccaccctt | cgatctggcg | aaaaacctgg | cggatggtaa | aggcgcggcc | 840 |
| gatggcacca | actggaaaat | tgataacaaa | gtggtgcgtg | tgccgtatgt | gggcgtggat | 900 |
| aaagataacc | tggccgaatt | t | | | | 921 |

<210> SEQ ID NO 57
<211> LENGTH: 921
<212> TYPE: DNA
<213> ORGANISM: Artificial Sequence
<220> FEATURE:
<223> OTHER INFORMATION: Synthetic

<400> SEQUENCE: 57

| | | | | | |
|---|---|---|---|---|---|
| atggcagata | ctcgtattgg | tgtaactatt | tataaatacg | atgataattg | tatgagcgta | 60 |
| gtacgtaaag | caattgaaca | agatgcgaaa | gcggccccgg | atgttcagct | gctgatgaac | 120 |
| gatagccaga | acgatcagag | caaacagaac | gatcagattg | atgtgctgct | ggccaaaggc | 180 |
| gtgaaagccc | tggccattaa | cctggttgat | ccggcggcgg | ccggtaccgt | tattgaaaaa | 240 |
| gcccgtggcc | agaacgtgcc | ggtggtgttc | ttcaacaaag | aaccgagccg | caaagcgctg | 300 |
| gatagctacg | ataaagcgta | ctatgtgggc | accgatagca | agaaagcgg | cattattcag | 360 |
| ggcgatctga | ttgcgaaaca | ttgggcggcg | aaccagggct | gggatctgaa | caaagatggc | 420 |
| cagattcagt | tcgtgctgct | gaaaggcgaa | ccgggtcatc | cggatgccga | agcgcgtacc | 480 |
| acctatgtga | tcaaagaact | gaacgacaaa | ggcatcaaaa | ccgaacagct | gcaactggat | 540 |
| accgcgatgt | gggataccgc | gcaggcgaaa | gataaaatgg | atgcgtggct | gagcggtccg | 600 |
| aacgcgaaca | aaattgaagt | ggtgattgcg | aacaacgatg | cgatggcgat | gggcgcggtg | 660 |

```
gaagcgctga aagcccataa caaatccagc attccggtgt ttggcgtgga tgccctgccg    720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 58
<211> LENGTH: 921
<212> TYPE: DNA
<213> ORGANISM: Artificial Sequence
<220> FEATURE:
<223> OTHER INFORMATION: Synthetic

<400> SEQUENCE: 58

```
atggcagata ctcgtattgg tgtaactatt tataaatacg atgcgaattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggcgaa ccgggtcatc cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg    720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 59
<211> LENGTH: 921
<212> TYPE: DNA
<213> ORGANISM: Artificial Sequence
<220> FEATURE:
<223> OTHER INFORMATION: Synthetic

<400> SEQUENCE: 59

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggcgaa ccgggtaacc cggatgccga agcgcgtacc    480
```

| | |
|---|---|
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa aagcggtgcg ctggcgggca ccgttctgaa cgatgccaac | 780 |
| aaccaggcga agccaccctt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 60
<211> LENGTH: 921
<212> TYPE: DNA
<213> ORGANISM: Artificial Sequence
<220> FEATURE:
<223> OTHER INFORMATION: Synthetic

<400> SEQUENCE: 60

| | |
|---|---|
| atggcagata ctcgtattgg tgtaactatt tataaatacg atgataattt catgagcgta | 60 |
| gtacgtaaag caattgaaca agatgcgaaa gcggccccgg atgttcagct gctgatgaac | 120 |
| gatagccaga cgatcagag caaacagaac gatcagattg atgtgctgct ggccaaaggc | 180 |
| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcgaa ccgggttttc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa aagcggtgcg ctggcgggca ccgttctgaa cgatgccaac | 780 |
| aaccaggcga agccaccctt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 61
<211> LENGTH: 921
<212> TYPE: DNA
<213> ORGANISM: Artificial Sequence
<220> FEATURE:
<223> OTHER INFORMATION: Synthetic

<400> SEQUENCE: 61

| | |
|---|---|
| atggcagata ctcgtattgg tgtaactatt tataaatacg atgataattt catgagcgta | 60 |
| gtacgtaaag caattgaaca agatgcgaaa gcggccccgg atgttcagct gctgatgaac | 120 |
| gatagccaga cgatcagag caaacagaac gatcagattg atgtgctgct ggccaaaggc | 180 |
| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |

```
ggcgatctga ttgcgaaaca ttgggcggcg aaccagggct gggatctgaa caaagatggc    420
cagattcagt tcgtgctgct gaaaggcgaa ccgggtcagc cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga aagcccataa caaatccagc attccggtgt ttggcgtgga tgccctgccg    720
gaagcgctgg cgctggttaa agcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 62
<211> LENGTH: 921
<212> TYPE: DNA
<213> ORGANISM: Artificial Sequence
<220> FEATURE:
<223> OTHER INFORMATION: Synthetic

<400> SEQUENCE: 62

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga cgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggccag ccgggtcatc cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga aagcccataa caaatccagc attccggtgt ttggcgtgga tgccctgccg    720
gaagcgctgg cgctggttaa agcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 63
<211> LENGTH: 921
<212> TYPE: DNA
<213> ORGANISM: Artificial Sequence
<220> FEATURE:
<223> OTHER INFORMATION: Synthetic

<400> SEQUENCE: 63

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga cgatcagag caaacagaac gatcagattg atgtgctgct ggccaaaggc    180
```

| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcagc ccgggtcatc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa agcggtgcg ctggcgggca ccgttctgaa cgatgccaac | 780 |
| aaccaggcga agccaccttt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 64
<211> LENGTH: 921
<212> TYPE: DNA
<213> ORGANISM: Artificial Sequence
<220> FEATURE:
<223> OTHER INFORMATION: Synthetic

<400> SEQUENCE: 64

| atggcagata ctcgtattgg tgtaactatt tataaatacg atgataattt catgagcgta | 60 |
| gtacgtaaag caattgaaca agatgcgaaa gcggcccccgg atgttcagct gctgatgaac | 120 |
| gatagccaga acgatcagag caaacagaac gatcagattg atgtgctgct ggccaaaggc | 180 |
| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcaaa ccgggtcatc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa agcggtgcg ctggcgggca ccgttctgaa cgatgccaac | 780 |
| aaccaggcga agccaccttt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 65
<211> LENGTH: 921
<212> TYPE: DNA
<213> ORGANISM: Artificial Sequence
<220> FEATURE:
<223> OTHER INFORMATION: Synthetic

<400> SEQUENCE: 65

| atggcagata ctcgtattgg tgtaactatt tataaatacg atgataattt catgagcgta | 60 |

```
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcgcg aaccagggct gggatctgaa caaagatggc       420
cagattcagt tcgtgctgct gaaaggcgaa ccgggtcatc cggataacga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg       720
gaagcgctgg cgctggttaa aagcggtgcg ctggcgggca ccgttctgaa cgatgccaac      780
aaccaggcga aagccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921

<210> SEQ ID NO 66
<211> LENGTH: 921
<212> TYPE: DNA
<213> ORGANISM: Artificial Sequence
<220> FEATURE:
<223> OTHER INFORMATION: Synthetic

<400> SEQUENCE: 66
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcgcg aaccagggct gggatctgaa caaagatggc       420
cagattcagt tcgtgctgct gaaaggcgaa ccgggtcatc cggatcatga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg       720
gaagcgctgg cgctggttaa aagcggtgcg ctggcgggca ccgttctgaa cgatgccaac      780
aaccaggcga aagccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921

<210> SEQ ID NO 67
<211> LENGTH: 921
<212> TYPE: DNA
<213> ORGANISM: Artificial Sequence
<220> FEATURE:
```

<223> OTHER INFORMATION: Synthetic

<400> SEQUENCE: 67

```
atggcagata ctcgtattgg tgtaactatt tataaatacg atgataattt catgagcgta    60
gtacgtaaag caattgaaca agatgcgaaa gcggccccgg atgttcagct gctgatgaac   120
gatagccaga acgatcagag caaacagaac gatcagattg atgtgctgct ggccaaaggc   180
gtgaaagccc tggccattaa cctggttgat ccggcggcgg ccggtaccgt tattgaaaaa   240
gcccgtggcc agaacgtgcc ggtggtgttc ttcaacaaag aaccgagccg caaagcgctg   300
gatagctacg ataaagcgta ctatgtgggc accgatagca agaaagcgg cattattcag    360
ggcgatctga ttgcgaaaca ttgggcggcg aaccagggct gggatctgaa caaagatggc   420
cagattcagt tcgtgctgct gaaaggcgaa ccgggtcatc cggattttga agcgcgtacc   480
acctatgtga tcaaagaact gaacgacaaa ggcatcaaaa ccgaacagct gcaactggat   540
accgcgatgt gcgataccgc gcaggcgaaa gataaaatgg atgcgtggct gagcggtccg   600
aacgcgaaca aaattgaagt ggtgattgcg aacaacgatg cgatggcgat gggcgcggtg   660
gaagcgctga agcccataa caaatccagc attccggtgt ttggcgtgga tgccctgccg    720
gaagcgctgg cgctggttaa agcggtgcg ctggcgggca ccgttctgaa cgatgccaac   780
aaccaggcga agccaccttc gatctggcg aaaaacctgg cggatggtaa aggcgcggcc    840
gatggcacca actggaaaat tgataacaaa gtggtgcgtg tgccgtatgt gggcgtggat   900
aaagataacc tggccgaatt t                                              921
```

<210> SEQ ID NO 68
<211> LENGTH: 921
<212> TYPE: DNA
<213> ORGANISM: Artificial Sequence
<220> FEATURE:
<223> OTHER INFORMATION: Synthetic

<400> SEQUENCE: 68

```
atggcagata ctcgtattgg tgtaactatt tataaatacg atgataattt catgagcgta    60
gtacgtaaag caattgaaca agatgcgaaa gcggccccgg atgttcagct gctgatgaac   120
gatagccaga acgatcagag caaacagaac gatcagattg atgtgctgct ggccaaaggc   180
gtgaaagccc tggccattaa cctggttgat ccggcggcgg ccggtaccgt tattgaaaaa   240
gcccgtggcc agaacgtgcc ggtggtgttc ttcaacaaag aaccgagccg caaagcgctg   300
gatagctacg ataaagcgta ctatgtgggc accgatagca agaaagcgg cattattcag    360
ggcgatctga ttgcgaaaca ttgggcggcg aaccagggct gggatctgaa caaagatggc   420
cagattcagt tcgtgctgct gaaaggcgaa ccgggtcatc cggataaaga agcgcgtacc   480
acctatgtga tcaaagaact gaacgacaaa ggcatcaaaa ccgaacagct gcaactggat   540
accgcgatgt gcgataccgc gcaggcgaaa gataaaatgg atgcgtggct gagcggtccg   600
aacgcgaaca aaattgaagt ggtgattgcg aacaacgatg cgatggcgat gggcgcggtg   660
gaagcgctga agcccataa caaatccagc attccggtgt ttggcgtgga tgccctgccg    720
gaagcgctgg cgctggttaa agcggtgcg ctggcgggca ccgttctgaa cgatgccaac   780
aaccaggcga agccaccttc gatctggcg aaaaacctgg cggatggtaa aggcgcggcc    840
gatggcacca actggaaaat tgataacaaa gtggtgcgtg tgccgtatgt gggcgtggat   900
aaagataacc tggccgaatt t                                              921
```

<210> SEQ ID NO 69
<211> LENGTH: 921
<212> TYPE: DNA
<213> ORGANISM: Artificial Sequence
<220> FEATURE:
<223> OTHER INFORMATION: Synthetic

<400> SEQUENCE: 69

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatctgga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacaacgatg cgatggcgat gggcgcggtg     660
gaagcgctga agcccataa caaatccagc attccggtgt ttggcgtgga tgccctgccg     720
gaagcgctgg cgctggttaa aagcggtgcg ctggcgggca ccgttctgaa cgatgccaac     780
aaccaggcga agccacctt cgatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                               921
```

<210> SEQ ID NO 70
<211> LENGTH: 921
<212> TYPE: DNA
<213> ORGANISM: Artificial Sequence
<220> FEATURE:
<223> OTHER INFORMATION: Synthetic

<400> SEQUENCE: 70

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatatgga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacaacgatg cgatggcgat gggcgcggtg     660
gaagcgctga agcccataa caaatccagc attccggtgt ttggcgtgga tgccctgccg     720
gaagcgctgg cgctggttaa aagcggtgcg ctggcgggca ccgttctgaa cgatgccaac     780
aaccaggcga agccacctt cgatctggcg aaaaacctgg cggatggtaa aggcgcggcc     840
```

```
gatggcacca actggaaaat tgataacaaa gtggtgcgtg tgccgtatgt gggcgtggat      900
aaagataacc tggccgaatt t                                                921
```

<210> SEQ ID NO 71
<211> LENGTH: 921
<212> TYPE: DNA
<213> ORGANISM: Artificial Sequence
<220> FEATURE:
<223> OTHER INFORMATION: Synthetic

<400> SEQUENCE: 71

```
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatcagga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg      720
gaagcgctgg cgctggttaa aagcggtgcg ctggcgggca ccgttctgaa cgatgccaac      780
aaccaggcga aagccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921
```

<210> SEQ ID NO 72
<211> LENGTH: 921
<212> TYPE: DNA
<213> ORGANISM: Artificial Sequence
<220> FEATURE:
<223> OTHER INFORMATION: Synthetic

<400> SEQUENCE: 72

```
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatagcga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg      720
```

```
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 73
<211> LENGTH: 921
<212> TYPE: DNA
<213> ORGANISM: Artificial Sequence
<220> FEATURE:
<223> OTHER INFORMATION: Synthetic

<400> SEQUENCE: 73

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga cgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggcgaa ccgggtcatc cggattggga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg    720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 74
<211> LENGTH: 921
<212> TYPE: DNA
<213> ORGANISM: Artificial Sequence
<220> FEATURE:
<223> OTHER INFORMATION: Synthetic

<400> SEQUENCE: 74

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga cgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggcgaa ccgggtcatc cggattatga agcgcgtacc    480
acctatgtga tcaaagaact gaacgacaaa ggcatcaaaa ccgaacagct gcaactggat    540
```

| | |
|---|---|
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa aagcggtgcg ctggcgggca ccgttctgaa cgatgccaac | 780 |
| aaccaggcga agccaccctt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 75
<211> LENGTH: 921
<212> TYPE: DNA
<213> ORGANISM: Artificial Sequence
<220> FEATURE:
<223> OTHER INFORMATION: Synthetic

<400> SEQUENCE: 75

| | |
|---|---|
| atggcagata ctcgtattgg tgtaactatt tataaatacg atgaaaattt catgagcgta | 60 |
| gtacgtaaag caattgaaca agatgcgaaa gcggccccgg atgttcagct gctgatgaac | 120 |
| gatagccaga acgatcagag caaacagaac gatcagattg atgtgctgct ggccaaaggc | 180 |
| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcgaa ccgggtcatc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa aagcggtgcg ctggcgggca ccgttctgaa cgatgccaac | 780 |
| aaccaggcga agccaccctt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 76
<211> LENGTH: 921
<212> TYPE: DNA
<213> ORGANISM: Artificial Sequence
<220> FEATURE:
<223> OTHER INFORMATION: Synthetic

<400> SEQUENCE: 76

| | |
|---|---|
| atggcagata ctcgtattgg tgtaactatt tataaatacg attttaattt catgagcgta | 60 |
| gtacgtaaag caattgaaca agatgcgaaa gcggccccgg atgttcagct gctgatgaac | 120 |
| gatagccaga acgatcagag caaacagaac gatcagattg atgtgctgct ggccaaaggc | 180 |
| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |

```
cagattcagt tcgtgctgct gaaaggcgaa ccgggtcatc cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921

<210> SEQ ID NO 77
<211> LENGTH: 921
<212> TYPE: DNA
<213> ORGANISM: Artificial Sequence
<220> FEATURE:
<223> OTHER INFORMATION: Synthetic

<400> SEQUENCE: 77
atggcagata ctcgtattgg tgtaactatt tataaatacg atcataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag     360 ggcgatctga ttgcgaaaca ttgggcggcg aaccagggct gggatctgaa caaagatggc    420
cagattcagt tcgtgctgct gaaaggcgaa ccgggtcatc cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921

<210> SEQ ID NO 78
<211> LENGTH: 921
<212> TYPE: DNA
<213> ORGANISM: Artificial Sequence
<220> FEATURE:
<223> OTHER INFORMATION: Synthetic

<400> SEQUENCE: 78
atggcagata ctcgtattgg tgtaactatt tataaatacg atctgaattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
```

| | |
|---|---|
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcgaa ccgggtcatc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa agcggtgcg ctggcgggca ccgttctgaa cgatgccaac | 780 |
| aaccaggcga aagccacctt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 79
<211> LENGTH: 921
<212> TYPE: DNA
<213> ORGANISM: Artificial Sequence
<220> FEATURE:
<223> OTHER INFORMATION: Synthetic

<400> SEQUENCE: 79

| | |
|---|---|
| atggcagata ctcgtattgg tgtaactatt tataaatacg ataacaattt catgagcgta | 60 |
| gtacgtaaag caattgaaca agatgcgaaa gcggccccgg atgttcagct gctgatgaac | 120 |
| gatagccaga acgatcagag caaacagaac gatcagattg atgtgctgct ggccaaaggc | 180 |
| gtgaaagccc tggccattaa cctggttgat ccggcggcgg ccgtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcgaa ccgggtcatc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa agcggtgcg ctggcgggca ccgttctgaa cgatgccaac | 780 |
| aaccaggcga aagccacctt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 80
<211> LENGTH: 921
<212> TYPE: DNA
<213> ORGANISM: Artificial Sequence
<220> FEATURE:
<223> OTHER INFORMATION: Synthetic

<400> SEQUENCE: 80

| | |
|---|---|
| atggcagata ctcgtattgg tgtaactatt tataaatacg atcagaattt catgagcgta | 60 |
| gtacgtaaag caattgaaca agatgcgaaa gcggccccgg atgttcagct gctgatgaac | 120 |

```
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg       720
gaagcgctgg cgctggttaa agcggtgcg ctggcgggca ccgttctgaa cgatgccaac       780
aaccaggcga agccaccctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                 921
```

<210> SEQ ID NO 81
<211> LENGTH: 921
<212> TYPE: DNA
<213> ORGANISM: Artificial Sequence
<220> FEATURE:
<223> OTHER INFORMATION: Synthetic

<400> SEQUENCE: 81

```
atggcagata ctcgtattgg tgtaactatt tataaatacg atagcaattt catgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg       720
gaagcgctgg cgctggttaa agcggtgcg ctggcgggca ccgttctgaa cgatgccaac       780
aaccaggcga agccaccctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                 921
```

<210> SEQ ID NO 82
<211> LENGTH: 921
<212> TYPE: DNA
<213> ORGANISM: Artificial Sequence
<220> FEATURE:
<223> OTHER INFORMATION: Synthetic

<400> SEQUENCE: 82

```
atggcagata ctcgtattgg tgtaactatt tataaatacg ataccaattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacaacgatg cgatggcgat gggcgcggtg     660
gaagcgctga agcccataa caaatccagc attccggtgt ttggcgtgga tgccctgccg     720
gaagcgctgg cgctggttaa aagcggtgcg ctggcgggca ccgttctgaa cgatgccaac     780
aaccaggcga agccaccttc gatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                               921
```

<210> SEQ ID NO 83
<211> LENGTH: 921
<212> TYPE: DNA
<213> ORGANISM: Artificial Sequence
<220> FEATURE:
<223> OTHER INFORMATION: Synthetic

<400> SEQUENCE: 83

```
atggcagata ctcgtattgg tgtaactatt tataaatacg attataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacaacgatg cgatggcgat gggcgcggtg     660
gaagcgctga agcccataa caaatccagc attccggtgt ttggcgtgga tgccctgccg     720
gaagcgctgg cgctggttaa aagcggtgcg ctggcgggca ccgttctgaa cgatgccaac     780
aaccaggcga agccaccttc gatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                               921
```

<210> SEQ ID NO 84
<211> LENGTH: 921

```
<212> TYPE: DNA
<213> ORGANISM: Artificial Sequence
<220> FEATURE:
<223> OTHER INFORMATION: Synthetic

<400> SEQUENCE: 84
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag     360
ggcgatctga ttgcgaaaca ttgggcggcg aaccagggct gggatctgaa caaagatggc    420
cagattcagt tcgtgctgct gaaaggcgaa ccgggtcatc cggcggccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga agccacctt cgatctggcg aaaaacctgg cggatggtaa aggcgcggcc     840
gatggcacca actggaaaat tgataacaaa gtggtgcgtg tgccgtatgt gggcgtggat    900
aaagataacc tggccgaatt t                                               921

<210> SEQ ID NO 85
<211> LENGTH: 921
<212> TYPE: DNA
<213> ORGANISM: Artificial Sequence
<220> FEATURE:
<223> OTHER INFORMATION: Synthetic

<400> SEQUENCE: 85
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag     360
ggcgatctga ttgcgaaaca ttgggcggcg aaccagggct gggatctgaa caaagatggc    420
cagattcagt tcgtgctgct gaaaggcgaa ccgggtcatc cgaacgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga agccacctt cgatctggcg aaaaacctgg cggatggtaa aggcgcggcc     840
gatggcacca actggaaaat tgataacaaa gtggtgcgtg tgccgtatgt gggcgtggat    900
```

```
aaagataacc tggccgaatt t                                         921
```

<210> SEQ ID NO 86
<211> LENGTH: 921
<212> TYPE: DNA
<213> ORGANISM: Artificial Sequence
<220> FEATURE:
<223> OTHER INFORMATION: Synthetic

<400> SEQUENCE: 86

```
atggcagata ctcgtattgg tgtaactatt tataaatacg atgataattt catgagcgta    60
gtacgtaaag caattgaaca agatgcgaaa gcggccccgg atgttcagct gctgatgaac   120
gatagccaga acgatcagag caaacagaac gatcagattg atgtgctgct ggccaaaggc   180
gtgaaagccc tggccattaa cctggttgat ccggcggcgg ccgtaccgt tattgaaaaa    240
gcccgtggcc agaacgtgcc ggtggtgttc ttcaacaaag aaccgagccg caaagcgctg   300
gatagctacg ataaagcgta ctatgtgggc accgatagca agaaagcgg cattattcag    360
ggcgatctga ttgcgaaaca ttgggcggcg aaccagggct gggatctgaa caaagatggc   420
cagattcagt tcgtgctgct gaaaggcgaa ccgggtcatc cggatgccga agcgcgtacc   480
acctatgtga tcaaagaact gaacgacaaa ggcatcaaaa ccgaacagct gcaactggat   540
accgcgatgt gcgataccgc gcaggcgaaa gataaaatgg atgcgtggct gagcggtccg   600
aacgcgaaca aaattgaagt ggtgattgcg aacaacgatg cgatggcgat gggcgcggtg   660
gaagcgctga agcccataa caaatccagc attccggtgt ttggcgtggc ggccctgccg   720
gaagcgctgg cgctggttaa aagcggtgcg ctggcgggca ccgttctgaa cgatgccaac   780
aaccaggcga agccaccctt cgatctggcg aaaaacctgg cggatggtaa aggcgcggcc   840
gatggcacca actggaaaat tgataacaaa gtggtgcgtg tgccgtatgt gggcgtggat   900
aaagataacc tggccgaatt t                                             921
```

<210> SEQ ID NO 87
<211> LENGTH: 921
<212> TYPE: DNA
<213> ORGANISM: Artificial Sequence
<220> FEATURE:
<223> OTHER INFORMATION: Synthetic

<400> SEQUENCE: 87

```
atggcagata ctcgtattgg tgtaactatt tataaatacg atgataattt catgagcgta    60
gtacgtaaag caattgaaca agatgcgaaa gcggccccgg atgttcagct gctgatgaac   120
gatagccaga acgatcagag caaacagaac gatcagattg atgtgctgct ggccaaaggc   180
gtgaaagccc tggccattaa cctggttgat ccggcggcgg ccgtaccgt tattgaaaaa    240
gcccgtggcc agaacgtgcc ggtggtgttc ttcaacaaag aaccgagccg caaagcgctg   300
gatagctacg ataaagcgta ctatgtgggc accgatagca agaaagcgg cattattcag    360
ggcgatctga ttgcgaaaca ttgggcggcg aaccagggct gggatctgaa caaagatggc   420
cagattcagt tcgtgctgct gaaaggcgaa ccgggtcatc cggatgccga agcgcgtacc   480
acctatgtga tcaaagaact gaacgacaaa ggcatcaaaa ccgaacagct gcaactggat   540
accgcgatgt gcgataccgc gcaggcgaaa gataaaatgg atgcgtggct gagcggtccg   600
aacgcgaaca aaattgaagt ggtgattgcg aacaacgatg cgatggcgat gggcgcggtg   660
gaagcgctga agcccataa caaatccagc attccggtgt ttggcgtgaa cgccctgccg   720
gaagcgctgg cgctggttaa aagcggtgcg ctggcgggca ccgttctgaa cgatgccaac   780
```

```
aaccaggcga agccaccttt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921
```

<210> SEQ ID NO 88
<211> LENGTH: 921
<212> TYPE: DNA
<213> ORGANISM: Artificial Sequence
<220> FEATURE:
<223> OTHER INFORMATION: Synthetic

<400> SEQUENCE: 88

```
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggccag ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg      720
gaagcgctgg cgctggttaa aagcggtgcg ctggcgggca ccgttctgaa cgatgccaac      780
aaccaggcga agccaccttt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921
```

<210> SEQ ID NO 89
<211> LENGTH: 921
<212> TYPE: DNA
<213> ORGANISM: Artificial Sequence
<220> FEATURE:
<223> OTHER INFORMATION: Synthetic

<400> SEQUENCE: 89

```
atggcagata ctcgtattgg tgtaactatt tataaatacg atgataatgc gatgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
```

```
aacgcgaaca aaattgaagt ggtgattgcg aacaacgatg cgatggcgat gggcgcggtg      660
gaagcgctga agcccataa caaatccagc attccggtgt ttggcgtgga tgccctgccg       720
gaagcgctgg cgctggttaa agcggtgcg ctggcgggca ccgttctgaa cgatgccaac       780
aaccaggcga agccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                 921

<210> SEQ ID NO 90
<211> LENGTH: 921
<212> TYPE: DNA
<213> ORGANISM: Artificial Sequence
<220> FEATURE:
<223> OTHER INFORMATION: Synthetic

<400> SEQUENCE: 90
atggcagata ctcgtattgg tgtaactatt tataaatacg atgataatct gatgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg       720
gaagcgctgg cgctggttaa agcggtgcg ctggcgggca ccgttctgaa cgatgccaac       780
aaccaggcga agccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                 921

<210> SEQ ID NO 91
<211> LENGTH: 921
<212> TYPE: DNA
<213> ORGANISM: Artificial Sequence
<220> FEATURE:
<223> OTHER INFORMATION: Synthetic

<400> SEQUENCE: 91
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga acgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtgcgc cggatgccga agcgcgtacc      480
```

```
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 92
<211> LENGTH: 921
<212> TYPE: DNA
<213> ORGANISM: Artificial Sequence
<220> FEATURE:
<223> OTHER INFORMATION: Synthetic

<400> SEQUENCE: 92

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag     360 ggcgatctga ttgcgaaaca ttgggcggcg aaccagggct gggatctgaa caaagatggc    420
cagattcagt tcgtgctgct gaaaggcgaa ccgggtaaac cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga aagccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 93
<211> LENGTH: 921
<212> TYPE: DNA
<213> ORGANISM: Artificial Sequence
<220> FEATURE:
<223> OTHER INFORMATION: Synthetic

<400> SEQUENCE: 93

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacgcgg aaccgagccg caaagcgctg    300
```

| | |
|---|---|
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcgaa ccgggtcatc cggatgccga agcgcgtacc | 480 |
| acctatgtga tcaaagaact gaacgacaaa ggcatcaaaa ccgaacagct gcaactggat | 540 |
| accgcgatgt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa aagcggtgcg ctggcgggca ccgttctgaa cgatgccaac | 780 |
| aaccaggcga agccaccttt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 94
<211> LENGTH: 921
<212> TYPE: DNA
<213> ORGANISM: Artificial Sequence
<220> FEATURE:
<223> OTHER INFORMATION: Synthetic

<400> SEQUENCE: 94

| | |
|---|---|
| atggcagata ctcgtattgg tgtaactatt tataaatacg atgataattt catgagcgta | 60 |
| gtacgtaaag caattgaaca agatgcgaaa gcggccccgg atgttcagct gctgatgaac | 120 |
| gatagccaga cgatcagag caaacagaac gatcagattg atgtgctgct ggccaaaggc | 180 |
| gtgaaagccc tggccattaa cctggttgat ccggcggcgg ccggtaccgt tattgaaaaa | 240 |
| gcccgtggcc agaacgtgcc ggtggtgttc ttcaacaaag aaccgagccg caaagcgctg | 300 |
| gatagctacg ataaagcgta ctatgtgggc accgatagca agaaagcgg cattattcag | 360 |
| ggcgatctga ttgcgaaaca ttgggcggcg aaccagggct gggatctgaa caaagatggc | 420 |
| cagattcagt tcgtgctgct gaaaggcgaa ccgggtcatc cggatgccga agcgcgtacc | 480 |
| acctatgtga tcaaagaact gaacgacaaa ggcatcaaaa ccgaacagct gcaactggat | 540 |
| accgcgtggt gcgataccgc gcaggcgaaa gataaaatgg atgcgtggct gagcggtccg | 600 |
| aacgcgaaca aaattgaagt ggtgattgcg aacaacgatg cgatggcgat gggcgcggtg | 660 |
| gaagcgctga agcccataa caaatccagc attccggtgt ttggcgtgga tgccctgccg | 720 |
| gaagcgctgg cgctggttaa aagcggtgcg ctggcgggca ccgttctgaa cgatgccaac | 780 |
| aaccaggcga agccaccttt cgatctggcg aaaaacctgg cggatggtaa aggcgcggcc | 840 |
| gatggcacca actggaaaat tgataacaaa gtggtgcgtg tgccgtatgt gggcgtggat | 900 |
| aaagataacc tggccgaatt t | 921 |

<210> SEQ ID NO 95
<211> LENGTH: 921
<212> TYPE: DNA
<213> ORGANISM: Artificial Sequence
<220> FEATURE:
<223> OTHER INFORMATION: Synthetic

<400> SEQUENCE: 95

| | |
|---|---|
| atggcagata ctcgtattgg tgtaactatt tataaatacg atgataattt catgagcgta | 60 |
| gtacgtaaag caattgaaca agatgcgaaa gcggccccgg atgttcagct gctgatgaac | 120 |
| gatagccaga cgatcagag caaacagaac gatcagattg atgtgctgct ggccaaaggc | 180 |

```
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360 ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacgcgatg cgatggcgat gggcgcggtg      660
gaagcgctga agcccataa caaatccagc attccggtgt ttggcgtgga tgccctgccg     720
gaagcgctgg cgctggttaa agcggtgcg ctggcgggca ccgttctgaa cgatgccaac      780
aaccaggcga agccaccctt cgatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                              921
```

<210> SEQ ID NO 96
<211> LENGTH: 921
<212> TYPE: DNA
<213> ORGANISM: Artificial Sequence
<220> FEATURE:
<223> OTHER INFORMATION: Synthetic

<400> SEQUENCE: 96

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360 ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aactttgatg cgatggcgat gggcgcggtg     660
gaagcgctga agcccataa caaatccagc attccggtgt ttggcgtgga tgccctgccg     720
gaagcgctgg cgctggttaa agcggtgcg ctggcgggca ccgttctgaa cgatgccaac      780
aaccaggcga agccaccctt cgatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                              921
```

<210> SEQ ID NO 97
<211> LENGTH: 921
<212> TYPE: DNA
<213> ORGANISM: Artificial Sequence
<220> FEATURE:
<223> OTHER INFORMATION: Synthetic

<400> SEQUENCE: 97

```
atggcagata ctcgtattgg tgtaactatt tataaatacg atgataattt catgagcgta    60
gtacgtaaag caattgaaca agatgcgaaa gcggccccgg atgttcagct gctgatgaac   120
gatagccaga acgatcagag caaacagaac gatcagattg atgtgctgct ggccaaaggc   180
gtgaaagccc tggccattaa cctggttgat ccggcggcgg ccgqtaccgt tattgaaaaa   240
gcccgtggcc agaacgtgcc ggtggtgttc ttcaacaaag aaccgagccg caaagcgctg   300
gatagctacg ataaagcgta ctatgtgggc accgatagca agaaagcgg cattattcag    360
ggcgatctga ttgcgaaaca ttgggcggcg aaccagggct gggatctgaa caaagatggc   420
cagattcagt tcgtgctgct gaaaggcgaa ccgggtcatc cggatgccga agcgcgtacc   480
acctatgtga tcaaagaact gaacgacaaa ggcatcaaaa ccgaacagct gcaactggat   540
accgcgatgt gcgataccgc gcaggcgaaa gataaaatgg atgcgtggct gagcggtccg   600
aacgcgaaca aaattgaagt ggtgattgcg aaccatgatg cgatggcgat gggcgcggtg   660
gaagcgctga agcccataa caaatccagc attccggtgt ttggcgtgga tgccctgccg    720
gaagcgctgg cgctggttaa agcggtgcg ctggcgggca ccgttctgaa cgatgccaac   780
aaccaggcga agccaccttt cgatctggcg aaaaacctgg cggatggtaa aggcgcggcc   840
gatggcacca actggaaaat tgataacaaa gtggtgcgtg tgccgtatgt gggcgtggat   900
aaagataacc tggccgaatt t                                             921

<210> SEQ ID NO 98
<211> LENGTH: 921
<212> TYPE: DNA
<213> ORGANISM: Artificial Sequence
<220> FEATURE:
<223> OTHER INFORMATION: Synthetic

<400> SEQUENCE: 98
atggcagata ctcgtattgg tgtaactatt tataaatacg atgataattt catgagcgta    60
gtacgtaaag caattgaaca agatgcgaaa gcggccccgg atgttcagct gctgatgaac   120
gatagccaga acgatcagag caaacagaac gatcagattg atgtgctgct ggccaaaggc   180
gtgaaagccc tggccattaa cctggttgat ccggcggcgg ccgqtaccgt tattgaaaaa   240
gcccgtggcc agaacgtgcc ggtggtgttc ttcaacaaag aaccgagccg caaagcgctg   300
gatagctacg ataaagcgta ctatgtgggc accgatagca agaaagcgg cattattcag    360
ggcgatctga ttgcgaaaca ttgggcggcg aaccagggct gggatctgaa caaagatggc   420
cagattcagt tcgtgctgct gaaaggcgaa ccgggtcatc cggatgccga agcgcgtacc   480
acctatgtga tcaaagaact gaacgacaaa ggcatcaaaa ccgaacagct gcaactggat   540
accgcgatgt gcgataccgc gcaggcgaaa gataaaatgg atgcgtggct gagcggtccg   600
aacgcgaaca aaattgaagt ggtgattgcg aacaaagatg cgatggcgat gggcgcggtg   660
gaagcgctga agcccataa caaatccagc attccggtgt ttggcgtgga tgccctgccg    720
gaagcgctgg cgctggttaa agcggtgcg ctggcgggca ccgttctgaa cgatgccaac   780
aaccaggcga agccaccttt cgatctggcg aaaaacctgg cggatggtaa aggcgcggcc   840
gatggcacca actggaaaat tgataacaaa gtggtgcgtg tgccgtatgt gggcgtggat   900
aaagataacc tggccgaatt t                                             921

<210> SEQ ID NO 99
<211> LENGTH: 921
<212> TYPE: DNA
<213> ORGANISM: Artificial Sequence
```

<220> FEATURE:
<223> OTHER INFORMATION: Synthetic

<400> SEQUENCE: 99

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccgtaccgt tattgaaaaa      240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacatggatg cgatggcgat gggcgcggtg     660
gaagcgctga agcccataa caaatccagc attccggtgt ttggcgtgga tgccctgccg      720
gaagcgctgg cgctggttaa agcggtgcg ctggcggca ccgttctgaa cgatgccaac       780
aaccaggcga agccaccctt cgatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                                921
```

<210> SEQ ID NO 100
<211> LENGTH: 921
<212> TYPE: DNA
<213> ORGANISM: Artificial Sequence
<220> FEATURE:
<223> OTHER INFORMATION: Synthetic

<400> SEQUENCE: 100

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccgtaccgt tattgaaaaa      240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aaccaggatg cgatggcgat gggcgcggtg     660
gaagcgctga agcccataa caaatccagc attccggtgt ttggcgtgga tgccctgccg      720
gaagcgctgg cgctggttaa agcggtgcg ctggcggca ccgttctgaa cgatgccaac       780
aaccaggcga agccaccctt cgatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                                921
```

<210> SEQ ID NO 101
<211> LENGTH: 921
<212> TYPE: DNA
<213> ORGANISM: Artificial Sequence
<220> FEATURE:
<223> OTHER INFORMATION: Synthetic

<400> SEQUENCE: 101

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aacagcgatg cgatggcgat gggcgcggtg     660
gaagcgctga agcccataa caaatccagc attccggtgt ttggcgtgga tgccctgccg     720
gaagcgctgg cgctggttaa aagcggtgcg ctggcgggca ccgttctgaa cgatgccaac     780
aaccaggcga agccaccctt cgatctggcg aaaaacctgg cggatggtaa aggcgcggcc     840
gatggcacca actggaaaat tgataacaaa gtggtgcgtg tgccgtatgt gggcgtggat     900
aaagataacc tggccgaatt t                                               921
```

<210> SEQ ID NO 102
<211> LENGTH: 921
<212> TYPE: DNA
<213> ORGANISM: Artificial Sequence
<220> FEATURE:
<223> OTHER INFORMATION: Synthetic

<400> SEQUENCE: 102

```
atggcagata ctcgtattgg tgtaactatt tataaatacg atgataattt catgagcgta      60
gtacgtaaag caattgaaca agatgcgaaa gcggccccgg atgttcagct gctgatgaac     120
gatagccaga acgatcagag caaacagaac gatcagattg atgtgctgct ggccaaaggc     180
gtgaaagccc tggccattaa cctggttgat ccggcggcgg ccggtaccgt tattgaaaaa     240
gcccgtggcc agaacgtgcc ggtggtgttc ttcaacaaag aaccgagccg caaagcgctg     300
gatagctacg ataaagcgta ctatgtgggc accgatagca agaaagcgg cattattcag      360
ggcgatctga ttgcgaaaca ttgggcggcg aaccagggct gggatctgaa caaagatggc     420
cagattcagt tcgtgctgct gaaaggcgaa ccgggtcatc cggatgccga agcgcgtacc     480
acctatgtga tcaaagaact gaacgacaaa ggcatcaaaa ccgaacagct gcaactggat     540
accgcgatgt gcgataccgc gcaggcgaaa gataaaatgg atgcgtggct gagcggtccg     600
aacgcgaaca aaattgaagt ggtgattgcg aactgggatg cgatggcgat gggcgcggtg     660
gaagcgctga agcccataa caaatccagc attccggtgt ttggcgtgga tgccctgccg     720
gaagcgctgg cgctggttaa aagcggtgcg ctggcgggca ccgttctgaa cgatgccaac     780
aaccaggcga agccaccctt cgatctggcg aaaaacctgg cggatggtaa aggcgcggcc     840
```
gatggcacca actggaaaat tgataacaaa gtggtgcgtg tgccgtatgt gggcgtggat      900
aaagataacc tggccgaatt t                                                921

<210> SEQ ID NO 103
<211> LENGTH: 921
<212> TYPE: DNA
<213> ORGANISM: Artificial Sequence
<220> FEATURE:
<223> OTHER INFORMATION: Synthetic

<400> SEQUENCE: 103
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga cgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aactatgatg cgatggcgat gggcgcggtg      660
gaagcgctga agcccataa caaatccagc attccggtgt ttggcgtgga tgccctgccg      720
gaagcgctgg cgctggttaa aagcggtgcg ctggcgggca ccgttctgaa cgatgccaac      780
aaccaggcga agccaccttt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921

<210> SEQ ID NO 104
<211> LENGTH: 921
<212> TYPE: DNA
<213> ORGANISM: Artificial Sequence
<220> FEATURE:
<223> OTHER INFORMATION: Synthetic

<400> SEQUENCE: 104
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga cgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660

```
gaagcgctga aagcccataa caaatccagc attccggtgt ttggcgtgga tgccctgccg      720
gaagcgctgg cgctggttaa aagcggtgcg ctggcgggca ccgttctggc ggatgccaac      780
aaccaggcga aagccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921
```

<210> SEQ ID NO 105
<211> LENGTH: 921
<212> TYPE: DNA
<213> ORGANISM: Artificial Sequence
<220> FEATURE:
<223> OTHER INFORMATION: Synthetic

<400> SEQUENCE: 105

```
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga cgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacaaag aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
accgcgatgt gcgataccgc gcaggcgaaa gataaaatgg atgcgtggct gagcggtccg      600
aacgcgaaca aaattgaagt ggtgattgcg aacaacgatg cgatggcgat gggcgcggtg      660
gaagcgctga agcccataa caaatccagc attccggtgt ttggcgtgga tgccctgccg      720
gaagcgctgg cgctggttaa aagcggtgcg ctggcgggca ccgttctgga tgatgccaac      780
aaccaggcga aagccacctt cgatctggcg aaaaacctgg cggatggtaa aggcgcggcc      840
gatggcacca actggaaaat tgataacaaa gtggtgcgtg tgccgtatgt gggcgtggat      900
aaagataacc tggccgaatt t                                                921
```

<210> SEQ ID NO 106
<211> LENGTH: 921
<212> TYPE: DNA
<213> ORGANISM: Artificial Sequence
<220> FEATURE:
<223> OTHER INFORMATION: Synthetic

<400> SEQUENCE: 106

```
atggcagata ctcgtattgg tgtaactatt tataaatacg atgataattt catgagcgta       60
gtacgtaaag caattgaaca agatgcgaaa gcggccccgg atgttcagct gctgatgaac      120
gatagccaga cgatcagag caaacagaac gatcagattg atgtgctgct ggccaaaggc      180
gtgaaagccc tggccattaa cctggttgat ccggcggcgg ccggtaccgt tattgaaaaa      240
gcccgtggcc agaacgtgcc ggtggtgttc ttcaacgcgg aaccgagccg caaagcgctg      300
gatagctacg ataaagcgta ctatgtgggc accgatagca agaaagcgg cattattcag       360 ggcgatctga ttgcgaaaca ttgggcggcg aaccagggct gggatctgaa caaagatggc      420
cagattcagt tcgtgctgct gaaaggcgaa ccgggtcatc cggatgccga agcgcgtacc      480
acctatgtga tcaaagaact gaacgacaaa ggcatcaaaa ccgaacagct gcaactggat      540
```

```
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga agccaccttc gatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921

<210> SEQ ID NO 107
<211> LENGTH: 921
<212> TYPE: DNA
<213> ORGANISM: Artificial Sequence
<220> FEATURE:
<223> OTHER INFORMATION: Synthetic

<400> SEQUENCE: 107
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggcgaa ccgggtcatc cggatgccga agcggcgacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg     720
gaagcgctgg cgctggttaa aagcggtgcg ctggcgggca ccgttctgaa cgatgccaac    780
aaccaggcga agccaccttc gatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921

<210> SEQ ID NO 108
<211> LENGTH: 921
<212> TYPE: DNA
<213> ORGANISM: Artificial Sequence
<220> FEATURE:
<223> OTHER INFORMATION: Synthetic

<400> SEQUENCE: 108
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360
```

```
ggcgatctga ttgcgaaaca ttgggcggcg aaccagggct gggatctgaa caaagatggc    420
cagattcagt tcgtgctgct gaaaggcgaa ccgggtcatc cggatgccga agcgaaaacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg    720
gaagcgctgg cgctggttaa agcggtgcg ctggcgggca ccgttctgaa cgatgccaac    780
aaccaggcga agccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 109
<211> LENGTH: 921
<212> TYPE: DNA
<213> ORGANISM: Artificial Sequence
<220> FEATURE:
<223> OTHER INFORMATION: Synthetic

<400> SEQUENCE: 109

```
atggcagata ctcgtattgg tgtaactatt gcgaaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
gcccgtggcc agaacgtgcc ggtggtgttc ttcaacaaag aaccgagccg caaagcgctg    300
gatagctacg ataaagcgta ctatgtgggc accgatagca agaaagcgg cattattcag    360 ggcgatctga ttgcgaaaca ttgggcggcg aaccagggct gggatctgaa caaagatggc    420
cagattcagt tcgtgctgct gaaaggcgaa ccgggtcatc cggatgccga agcgcgtacc    480
acctatgtga tcaaagaact gaacgacaaa ggcatcaaaa ccgaacagct gcaactggat    540
accgcgatgt gcgataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa caaatccagc attccggtgt ttggcgtgga tgccctgccg    720
gaagcgctgg cgctggttaa agcggtgcg ctggcgggca ccgttctgaa cgatgccaac    780
aaccaggcga agccacctt cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 110
<211> LENGTH: 921
<212> TYPE: DNA
<213> ORGANISM: Artificial Sequence
<220> FEATURE:
<223> OTHER INFORMATION: Synthetic

<400> SEQUENCE: 110

```
atggcagata ctcgtattgg tgtaactatt tataaatacg atgataattt catgagcgta     60
gtacgtaaag caattgaaca agatgcgaaa gcggccccgg atgttcagct gctgatgaac    120
gatagccaga acgatcagag caaacagaac gatcagattg atgtgctgct ggccaaaggc    180
gtgaaagccc tggccattaa cctggttgat ccggcggcgg ccggtaccgt tattgaaaaa    240
```

-continued

```
gcccgtggcc agaacgtgcc ggtggtgttc ttcaacaaag aaccgagccg caaagcgctg    300
gatagctacg ataaagcgta ctatgtgggc accgatagca agaaagcgg  cattattcag    360 ggcgatctga ttgcgaaaca ttgggcggcg aaccagggct gggatctgaa caaagatggc    420
cagattcagt tcgtgctgct gaaaggcgaa ccgggtcatc cggatgccga agcgcgtacc    480
acctatgtga tcaaagaact gaacgacaaa ggcatcaaaa ccgaacagct gcaactggat    540
accgcgatgt gggataccgc gcaggcgaaa gataaaatgg atgcgtggct gagcggtccg    600
aacgcgaaca aaattgaagt ggtgattgcg aacaacgatg cgatggcgat gggcgcggtg    660
gaagcgctga agcccataa  caaatccagc attccggtgt ttggcgtgga tgccctgccg    720
gaagcgctgg cgctggttaa aagcggtgcg ctggcgggca ccgttctgaa cgatgccaac    780
aaccaggcga agccacctt  cgatctggcg aaaaacctgg cggatggtaa aggcgcggcc    840
gatggcacca actggaaaat tgataacaaa gtggtgcgtg tgccgtatgt gggcgtggat    900
aaagataacc tggccgaatt t                                              921
```

<210> SEQ ID NO 111
<211> LENGTH: 9
<212> TYPE: PRT
<213> ORGANISM: Artificial Sequence
<220> FEATURE:
<223> OTHER INFORMATION: Synthetic

<400> SEQUENCE: 111

Gly Gly Ser His His His His His His
1               5

<210> SEQ ID NO 112
<211> LENGTH: 306
<212> TYPE: PRT
<213> ORGANISM: Escherichia coli

<400> SEQUENCE: 112

Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

-continued

```
Gln Leu Asp Thr Ala Met Trp Asp Thr Ala Gln Ala Lys Asp Lys Met
            180             185             190

Asp Ala Trp Leu Ser Gly Pro Asn Ala Asn Lys Ile Glu Val Val Ile
        195             200             205

Ala Asn Asn Asp Ala Met Ala Met Gly Ala Val Glu Ala Leu Lys Ala
    210             215             220

His Asn Lys Ser Ser Ile Pro Val Phe Gly Val Asp Ala Leu Pro Glu
225             230             235             240

Ala Leu Ala Leu Val Lys Ser Gly Ala Leu Ala Gly Thr Val Leu Asn
                245             250             255

Asp Ala Asn Asn Gln Ala Lys Ala Thr Phe Asp Leu Ala Lys Asn Leu
            260             265             270

Ala Asp Gly Lys Gly Ala Ala Asp Gly Thr Asn Trp Lys Ile Asp Asn
        275             280             285

Lys Val Val Arg Val Pro Tyr Val Gly Val Asp Lys Asp Asn Leu Ala
    290             295             300

Glu Phe
305
```